US008669247B2

(12) United States Patent
Ly et al.

(10) Patent No.: US 8,669,247 B2
(45) Date of Patent: Mar. 11, 2014

(54) 2,5-DISUBSTITUTED ARYLSULFONAMIDE CCR3 ANTAGONISTS

(71) Applicants: Tai Wei Ly, San Diego, CA (US); Marie Chantal Siu-Ying Tran, Arcadia, CA (US); Erik Dean Raaum, Teton Village, WY (US)

(72) Inventors: Tai Wei Ly, San Diego, CA (US); Marie Chantal Siu-Ying Tran, Arcadia, CA (US); Erik Dean Raaum, Teton Village, WY (US)

(73) Assignee: Axikin Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 13/846,222

(22) Filed: Mar. 18, 2013

(65) Prior Publication Data

US 2013/0225565 A1 Aug. 29, 2013

Related U.S. Application Data

(62) Division of application No. 12/764,900, filed on Apr. 21, 2010, now Pat. No. 8,399,456.

(60) Provisional application No. 61/171,775, filed on Apr. 22, 2009.

(51) Int. Cl.
*A61K 31/551* (2006.01)
*A61K 31/445* (2006.01)
*A61K 31/497* (2006.01)
*A61K 31/4965* (2006.01)

(52) U.S. Cl.
USPC . 514/218; 514/329; 514/252.12; 514/255.03; 514/322

(58) Field of Classification Search
USPC ......... 514/218, 252.12, 238.8, 329, 331, 326, 514/524, 227.5, 255.03, 322
See application file for complete search history.

(56) References Cited

U.S. PATENT DOCUMENTS

| 7,071,180 B2 | 7/2006 | Nilsson et al. |
| 7,674,797 B2 | 3/2010 | Li et al. |
| 7,700,586 B2 | 4/2010 | Li et al. |
| 7,759,339 B2 | 7/2010 | Aertgeerts et al. |
| 2009/0286771 A1 | 11/2009 | Li et al. |

FOREIGN PATENT DOCUMENTS

| WO | WO 03/022277 | 3/2003 |
| WO | WO 2004/084898 | 10/2004 |

OTHER PUBLICATIONS

Abonyo et al., "Modulation of eotaxin-3 (CCL26) in alveolar type II epithelial cells," *Cytokine*, 36:237-244 (2006).

Akashi et al., "A novel small-moleucle compound targeting CCR5 and CXCR3 prevents acute and chronic allograft rejection," *Transplantation*, 80:378-384 (2005).
Alaaeddine et al., "Production of the chemokine RANTES by articular chondrocytes and role in cartilage degradation," *Arthritis & Rheumatism*, 44(7):1633-1643 (2001).
Bischoff et al., "Immunnohistological assessment of intestinal eosinophil activation in patients with eosinophilic gastroenteritis and inflammatory bowel disease," *Am. J. Gastroenterol.*, 94:3521-3529 (1999).
Combadiere et al., "Cloning and functional expression of a human eosinophil CC chemokine receptor," *J. Biol. Chem.*, 270:16491-16494 (1995).
Durham and Kay, "Eosinophils, bronchial hyperreactivity and late-phase asthmatic reactions," *Clin. Allerg*, 15:411-418 (1985).
Durham, "Mechanisms of mucosal inflammation in the nose and lungs," *Clin. Exp. Allergy*, 28(Suppl. 2):11-16 (1998).
Evans et al., "Pretreatment with antibody to eosinophil major basic protein prevents hyperresponsiveness by protecting neuronal M2 muscarinic receptors in antigen-challenged guinea pigs," *J. Clin. Invest.*, 100:2254-2262 (1997).
Fullkerson et al., "A central regulatory role for eosinophils and the eotaxin/CCR3 axis in chronic experimental allergic airway inflammation," *Proc. Natl. Acad. Sci. USA*, 103:16418-16423 (2006).
Grimaldi et al., "Depletion of eosinophils in mice through the use of antibodies specific for C-C chemokine receptor 3 (CCR3)," *J. Leukocyte Biol.*, 65:846-853 (1999).
Heath et al., "Chemokine receptor usage by human eosinophils. The importance of CCR3 demonstrated using an antagonistic monoclonal antibody," *J. Clin. Invest.*, 99:178-184 (1997).
Humbles et al., "The murine CCR3 receptor regulates both the role of eosinophils and mast cells in allergen-induced airway inflammation and hyperresponsiveness," *Proc. Natl. Acad. Sci. USA*, 99:1479-1484 (2002).
Justice et al.," Ablation of eosinophils leads to a reduction of allergen-induced pulmonary pathology," *Am. J. Physiol. Lung Cell. Mol. Physiol.*, 284:L169-L178 (2003).
Katschke et al., "Differential expression of chemokine receptors on peripheral blood, synovial fluid, and synovial tissue monocytes/macrophages in rheumatoid arthritis," *Arthritis & Rheumatism*, 44(5):1022-1032 (2001).
Kroegel et al., "Blood and bronchoalveolar eosinophils in allergic subjects after segmental antigen challenge: surface phenotype, density heterogeneity, and prostanoid production," *J. Allergy Clin. Immunol.*, 93:725-734 (1994).
Leung, "Pathogenesis of atopic dermatitis," *J. Allergy Clin. Immunol.*, 104:S99-108 (1999).
Ma et al., "CCR3 is essential for skin eosinophilia and airway hyperresponsiveness in a murine model of allergic skin inflammation," *J. Clin. Invest.*, 109:621-628 (2002).

(Continued)

*Primary Examiner* — Kristin Vajda
(74) *Attorney, Agent, or Firm* — Jones Day

(57) ABSTRACT

Provided herein are 2,5-disubstituted arylsulfonamides that are useful for modulating CCR3 activity, and pharmaceutical compositions thereof. Also provided herein are methods of their use for treating, preventing, or ameliorating one or more symptoms of a CCR3-mediated disorder, disease, or condition.

40 Claims, No Drawings

(56) References Cited

OTHER PUBLICATIONS

Nakamura et al., "A specific CCR3 chemokine receptor antagonist inhibits both early and late phase allergic inflammation in the conjunctiva," *Immunological Res.*, 33(3):213-221 (2005).

Pope et al., "The eotaxin chemokines and CCR3 are fundamental regulators of allergen-induced pulmonary eosinophilia," *J. Immunol.*, 175:5341-5350 (2005).

Post et al., "Molecular characterization of two murine eosinophil beta chemokine receptors," *J. Immunol.*, 155:5299-5305 (1995).

Sabroe et al., "A small molecule antagonist of chemokine receptors CCR1 and CCR3" *J. Biol. Chem.* 275(34):25985-25992 (2000).

Stellato et al., "Cutting edge: expression of the C-C chemokine receptor CCR3 in human airway epithelial cells," *J. Immunology*, 166(3):1457-1461 (2001).

Vippagunta et al., "Crystal line solids," *Advanced Drug Delivery Reviews*, 43:3-26 (2001).

White et al., "Identification of potent, selective non-peptide CC chemokine receptor-3 antagonist that inhibits eotaxin-, eotaxin-2-, and monocyte chemotactic protein-4-induced eosinophil migration," *J. Biol. Chem.*, 275(47):36626-36631 (2000).

Ying et al., "Eosinophil chemotactic chemokines (eotaxin, eotaxin-2, RANTES, monocyte chemoattractant protein-3 (MCP-3), and MCP-4), and C-C chemokine receptor 3 expression in bronchial biopsies from atopic and nonatopic (Intrinsic) asthmatics," *J. Immunol.*, 163:6321-6329 (1999).

2,5-DISUBSTITUTED ARYLSULFONAMIDE CCR3 ANTAGONISTS

CROSS REFERENCE TO RELATED APPLICATIONS

This application is a divisional of U.S. application Ser. No. 12/764,900, filed Apr. 21, 2010, and claims priority to U.S. Provisional Application No. 61/171,775, filed Apr. 22, 2009, the disclosure of each of which is incorporated herein by reference in its entirety.

FIELD

Provided herein are 2,5-disubstituted arylsulfonamides that are useful for modulating CCR3 activity, and pharmaceutical compositions thereof. Also provided herein are methods of their use for treating, preventing, or ameliorating one or more symptoms of a CCR3-mediated disorder, disease, or condition.

BACKGROUND

CC chemokine receptor 3 (CCR3) is a seven-transmembrane G protein-coupled receptor, which binds to a variety of C—C chemokines, including eotaxin (CCL11), eotaxin-3 (CCL26), MCP-3 (CCL7), MCP-4 (CCL13), and RANTES (CCL5). CCR3 is known to be a major chemokine receptor expressed on allergic inflammatory cells, including eosinophils, basophils, mast cells, and T helper 2-type $CD4^+$ cells (Combadiere et al. *J. Biol. Chem.* 1995, 270, 16491-16494; Post et al., *J. Immunol.* 1995, 155, 5299-5305). Eosinophils have been implicated in the pathogenesis of a number of allergic diseases, such as bronchial asthma (Durham and Kay, *Clin. Allergy* 1985, 15, 411-418; Kroegel et al, *J. Allergy Clin. Immunol* 1994, 93, 725-734), allergic rhinitis (Durham, *Clin. Exp. Allergy* 1998, 28 Suppl. 2, 11-16), atopic dermatitis (Leung, *J. Allergy Clin. Immunol.* 1999, 104, S99-108), and eosinophilic gastroenteritis (Bischoff et al., *Am. J. Gastro.* 1999, 94, 3521-3529). It has been demonstrated that activated eosinophils release major basic protein (MBP), which blocks inhibitory M2 muscarinic receptors (M2Rs) on nerves, increasing acetylcholine release, and potentiating vagally mediated bronchoconstriction (Evans et al., *J. Clin. Invest.* 1997, 100, 2254-2262).

Numerous reports indicate that CCR3 plays important roles in allergic conditions. For example, it has been reported that, in both atopic and nonatopic asthma patients, there are increases in both mRNA and protein levels of CCR3 and its ligands, eotaxin, eotaxin-2. RANTES, and MCP-4 (Ying et al., *J. Immunol.* 1999, 99, 6321-6329). It has also been demonstrated that CCR3 gene deletion impairs eosinophil recruitment in an acute model of experimental asthma (Humbles et al., *Proc. Natl. Acad. Sci. USA* 2002, 99, 1479-1484; Ma et al., *J. Clin. Invest.* 2002, 109, 621-628; Pope et al., *J. Immunol.* 2005, 175, 5341-5350; Fulkerson et al., *Proc. Natl. Acad. Sci. USA* 2006, 103, 16418-16423). Furthermore, studies have shown that CCR3 antagonists, such as anti-CCR3 monoclonal antibodies, block binding of CCR3-ligands to either CCR3 transfectants or eosinophils, thus blocking chemotaxis of eosinophils induced by C—C chemokines, such as eotaxin, RANTES, or MCP-3 (Heath et al., *J. Clin. Invest.* 1997, 99, 178-184; Grimaldi et al., *J. Leukocyte Biol.* 1999, 65, 846-853; Justice et al., *Am. J. Physiol.* 2003, 284, L168-L178). Therefore, CCR3 antagonists are potentially useful for the treatment of inflammatory diseases, such as allergic rhinitis and allergic asthma. In addition, CCR3 antagonists are also potentially useful blocking infection of CCR3 expressing cells by some microorganisms, such as HIV, as CCR3 is known to be an entry co-receptor for some microorganisms.

SUMMARY OF THE DISCLOSURE

Provided herein is a 2,5-disubstituted arylsulfonamide of Formula I:

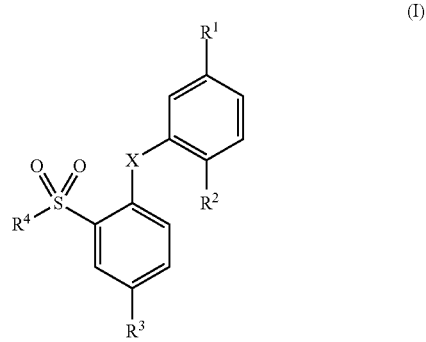

(I)

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof;

wherein:

$R^1$ and $R^2$ are each independently (a) halo, cyano, nitro, hydroxyl, or guanidine; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, phenyl, benzyl, phenoxy, benzoxy, or heterocyclyl; or (d) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;

$R^3$ is (a) hydrogen, halo, cyano, nitro, or hydroxyl; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, or tetrazolyl; or (d) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)$R^{1d}$, —N$R^{1a}$S(O)$_2R^{1d}$, —S(O)$R^{1a}$, —S(O)$_2R^{1a}$, —S(O)N$R^{1b}R^{1c}$, or S(O)$_2$N$R^{1b}R^{1c}$;

$R^4$ is

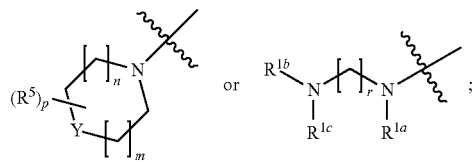

$R^5$ is (a) halo, cyano, nitro, hydroxyl, oxo, or guanidine; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, phenyl, benzyl, phenoxy, benzoxy, or heterocyclyl; or (d) —C(O)R$^{1a}$, —C(O)OR$^{1a}$, —C(O)NR$^{1b}$R$^{1c}$, —C(NR$^{1a}$)NR$^{1b}$R$^{1c}$, —OC(O)R$^{1a}$, —OC(O)OR$^{1a}$, —OC(O)NR$^{1b}$R$^{1c}$, —OC(=NR$^{1a}$)NR$^{1b}$R$^{1c}$, —OS(O)R$^{1a}$, —OS(O)$_2$R$^{1a}$, —OS(O)NR$^{1b}$R$^{1c}$, —OS(O)$_2$NR$^{1b}$R$^{1c}$, —NR$^{1b}$R$^{1c}$, —NR$^{1a}$C(O)R$^{1d}$, —NR$^{1a}$C(O)OR$^{1d}$, —NR$^{1a}$C(O)NR$^{1b}$R$^{1c}$, —NR$^{1a}$C(=NR$^{1d}$)NR$^{1b}$R$^{1c}$, —NR$^{1a}$S(O)R$^{1d}$, —NR$^{1a}$S(O)$_2$R$^{1d}$, —NR$^{1a}$S(O)R$^{1d}$, —NR$^{1a}$S(O)$_2$R$^{1d}$, —S(O)R$^{1a}$, —S(O)$_2$R$^{1a}$, —S(O)NR$^{1b}$R$^{1c}$, or —S(O)$_2$NR$^{1b}$R$^{1c}$;

X is O or S:

Y is —O—, —S—, —S(O)—, —S(O)$_2$—, —N(R$^{1a}$)—, —C(R$^{1a}$)(R$^{1d}$)—, or —C(R$^{1a}$)(NR$^{1b}$R$^{1c}$)—;

m is an integer from 0 to 3;

n is an integer from 1 to 3;

p is an integer from 0 to 4;

r is an integer from 1 to 6; and each R$^{1a}$, R$^{1b}$, R$^{1c}$, and R$^{1d}$ is independently (a) hydrogen, phenyl, or benzyl; (b) $C_{3-7}$ cycloalkyl, heteroaryl, or heterocyclyl, each optionally substituted; or (c) $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; or each pair of R$^{1b}$ and R$^{1c}$ together with the N atom to which they are attached independently form heteroaryl or heterocyclyl;

with the proviso that when X is O; Y is —N(R$^{1a}$)—; m and n are 1; R$^1$ and R$^2$ are each independently chloro, nitro, methyl, or isopropyl; R$^3$ is nitro; and p is 0; then R$^{1a}$ is not hydrogen.

Also provided herein are pharmaceutical compositions comprising a compound disclosed herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; in combination with one or more pharmaceutically acceptable carriers.

Further provided herein is a method for modulating CCR3 activity, comprising contacting a CCR3 with a therapeutically effective amount of a compound disclosed herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

Additionally provided herein is a method for treating, preventing, or ameliorating one or more symptoms of a CCR3-mediated disorder, disease, or condition in a subject, comprising administering to the subject a therapeutically effective amount of a compound disclosed herein, e.g., a compound of Formula I, an enantiomer, a mixture of enantiomers, a mixture of two or more diastereomers, a tautomer, or a mixture of two or more tautomers thereof; or a pharmaceutically acceptable salt, solvate, hydrate, or prodrug thereof.

DETAILED DESCRIPTION

To facilitate understanding of the disclosure set forth herein, a number of terms are defined below.

Generally, the nomenclature used herein and the laboratory procedures in organic chemistry, medicinal chemistry, and pharmacology described herein are those well known and commonly employed in the art. Unless defined otherwise, all technical and scientific terms used herein generally have the same meaning as commonly understood by one of ordinary skill in the art to which this disclosure belongs. In the event that there is a plurality of definitions for a term used herein, those in this section prevail unless stated otherwise.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject, in one embodiment, a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The term "therapeutically effective amount" are meant to include the amount of a compound that, when administered, is sufficient to prevent development of, or alleviate to some extent, one or more of the symptoms of the disorder, disease, or condition being treated. The term "therapeutically effective amount" also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically-acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of humans and animals without excessive toxicity, irritation, allergic response, immunogenicity, or other problems or complications, commensurate with a reasonable benefit/risk ratio. See, *Remington: The Science and Practice of Pharmacy,* 21st Edition, Lippincott Williams & Wilkins: Philadelphia, Pa., 2005; *Handbook of Pharmaceutical Excipients,* 5th Edition, Rowe et al., Eds., The Pharmaceutical Press and the American Pharmaceutical Association: 2005; and *Handbook of Pharmaceutical Additives,* 3rd Edition, Ash and Ash Eds., Gower Publishing Company: 2007; *Pharmaceutical Preformulation and Formulation,* Gibson Ed., CRC Press LLC: Boca Raton, Fla., 2004.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

The terms "active ingredient" and "active substance" refer to a compound, which is administered, alone or in combination with one or more pharmaceutically acceptable excipients, to a subject for treating, preventing, or ameliorating one or more symptoms of a condition, disorder, or disease. As used herein, "active ingredient" and "active substance" may be an optically active isomer of a compound described herein.

The terms "drug," "therapeutic agent," and "chemotherapeutic agent" refer to a compound, or a pharmaceutical composition thereof, which is administered to a subject for treating, preventing, or ameliorating one or more symptoms of a condition, disorder, or disease.

The term "alkyl" refers to a linear or branched saturated monovalent hydrocarbon radical, wherein the alkyl may optionally be substituted as described herein. In certain embodiments, the alkyl is a linear saturated monovalent hydrocarbon radical that has 1 to 20 ($C_{1-20}$), 1 to 15 ($C_{1-15}$), 1 to 10 ($C_{1-10}$), or 1 to 6 ($C_{1-6}$) carbon atoms, or branched saturated monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. As used herein, linear $C_{1-6}$ and branched $C_{3-6}$ alkyl groups are also referred as "lower alkyl." Examples of alkyl groups include, but are not limited to, methyl, ethyl, propyl (including all isomeric forms), n-propyl, isopropyl, butyl (including all isomeric forms), n-butyl, isobutyl, sec-butyl, t-butyl, pentyl (including all isomeric forms), and hexyl (including all isomeric forms). For example, $C_{1-6}$ alkyl refers to a linear saturated monovalent hydrocarbon radical of 1 to 6 carbon atoms or a branched saturated monovalent hydrocarbon radical of 3 to 6 carbon atoms.

The term "alkenyl" refers to a linear or branched monovalent hydrocarbon radical, which contains one or more, in one embodiment, one to five, in another embodiment, one, carbon-carbon double bond(s). The alkenyl may be optionally substituted as described herein. The term "alkenyl" also embraces radicals having "cis" and "trans" configurations, or alternatively, "Z" and "E" configurations, as appreciated by those of ordinary skill in the art. As used herein, the term "alkenyl" encompasses both linear and branched alkenyl, unless otherwise specified. For example, $C_{2-6}$ alkenyl refers to a linear unsaturated monovalent hydrocarbon radical of 2 to 6 carbon atoms or a branched unsaturated monovalent hydrocarbon radical of 3 to 6 carbon atoms. In certain embodiments, the alkenyl is a linear monovalent hydrocarbon radical of 2 to 20 ($C_{2-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkenyl groups include, but are not limited to, ethenyl, propen-1-yl, propen-2-yl, allyl, butenyl, and 4-methylbutenyl.

The term "alkynyl" refers to a linear or branched monovalent hydrocarbon radical, which contains one or more, in one embodiment, one to five, in another embodiment, one, carbon-carbon triple bond(s). The alkynyl may be optionally substituted as described herein. The term "alkynyl" also encompasses both linear and branched alkynyl, unless otherwise specified. In certain embodiments, the alkynyl is a linear monovalent hydrocarbon radical of 2 to 20 ($C_{7-20}$), 2 to 15 ($C_{2-15}$), 2 to 10 ($C_{2-10}$), or 2 to 6 ($C_{2-6}$) carbon atoms, or a branched monovalent hydrocarbon radical of 3 to 20 ($C_{3-20}$), 3 to 15 ($C_{3-15}$), 3 to 10 ($C_{3-10}$), or 3 to 6 ($C_{3-6}$) carbon atoms. Examples of alkynyl groups include, but are not limited to, ethynyl (—C≡CH) and propargyl (—CH$_2$C≡CH). For example, $C_{2-6}$ alkynyl refers to a linear unsaturated monovalent hydrocarbon radical of 2 to 6 carbon atoms or a branched unsaturated monovalent hydrocarbon radical of 3 to 6 carbon atoms.

The term "cycloalkyl" refers to a cyclic monovalent hydrocarbon radical, which may be optionally substituted as described herein. In one embodiment, cycloalkyl groups may be saturated, and/or bridged, and/or non-bridged, and/or fused bicyclic groups. In certain embodiments, the cycloalkyl has from 3 to 20 ($C_{3-20}$), from 3 to 15 ($C_{3-15}$), from 3 to 10 ($C_{3-10}$), or from 3 to 7 ($C_{3-7}$) carbon atoms. Examples of cycloalkyl groups include, but are not limited to, cyclopropyl, cyclobutyl, cyclopentyl, cyclohexyl, cycloheptyl, bicyclo[2.1.1]hexyl, bicyclo[2.2.1]heptyl, decalinyl, and adamantyl.

The term "aryl" refers to a monovalent monocyclic aromatic group and/or monovalent multicyclic aromatic group that contain at least one aromatic carbon ring. In certain embodiments, the aryl has from 6 to 20 ($C_{6-20}$), from 6 to 15 ($C_{6-15}$), or from 6 to 10 ($C_{6-10}$) ring atoms. Examples of aryl groups include, but are not limited to, phenyl, naphthyl, fluorenyl, azulenyl, anthryl, phenanthryl, pyrenyl, biphenyl, and terphenyl. Aryl also refers to bicyclic or tricyclic carbon rings, where one of the rings is aromatic and the others of which may be saturated, partially unsaturated, or aromatic, for example, dihydronaphthyl, indenyl, indanyl, or tetrahydronaphthyl (tetralinyl). In certain embodiments, aryl may be optionally substituted as described herein.

The term "heteroaryl" refers to a monovalent monocyclic aromatic group and/or multicyclic aromatic group that contain at least one aromatic ring, wherein at least one aromatic ring contains one or more heteroatoms independently selected from O, S, and N in the ring. Heteroaryl groups are bonded to the rest of the molecule through the aromatic ring. Each ring of a heteroaryl group can contain one or two O atoms, one or two S atoms, and/or one to four N atoms, provided that the total number of heteroatoms in each ring is four or less and each ring contains at least one carbon atom. In certain embodiments, the heteroaryl has from 5 to 20, from 5 to 15, or from 5 to 10 ring atoms. Examples of monocyclic heteroaryl groups include, but are not limited to, furanyl, imidazolyl, isothiazolyl, isoxazolyl, oxadiazolyl, oxadiazolyl, oxazolyl, pyrazinyl, pyrazolyl, pyridazinyl, pyridyl, pyrimidinyl, pyrrolyl, thiadiazolyl, thiazolyl, thienyl, tetrazolyl, triazinyl, and triazolyl. Examples of bicyclic heteroaryl groups include, but are not limited to, benzofuranyl, benzimidazolyl, benzoisoxazolyl, benzopyranyl, benzothiadiazolyl, benzothiazolyl, benzothienyl, benzotriazolyl, benzoxazolyl, furopyridyl, imidazopyridinyl, imidazothiazolyl, indolizinyl, indolyl, indazolyl, isobenzofuranyl, isobenzothienyl, isoindolyl, isoquinolinyl, isothiazolyl, naphthyridinyl, oxazolopyridinyl, phthalazinyl, pteridinyl, purinyl, pyridopyridyl, pyrrolopyridyl, quinolinyl, quinoxalinyl, quinazolinyl, thiadiazolopyrimidyl, and thienopyridyl. Examples of tricyclic heteroaryl groups include, but are not limited to, acridinyl, benzindolyl, carbazolyl, dibenzofuranyl, perimidinyl, phenanthrolinyl, phenanthridinyl, phenarsazinyl, phenazinyl, phenothiazinyl, phenoxazinyl, and xanthenyl. In certain embodiments, heteroaryl may also be optionally substituted as described herein.

The term "heterocyclyl" or "heterocyclic" refers to a monovalent monocyclic non-aromatic ring system and/or multicyclic ring system that contains at least one non-aromatic ring, wherein one or more of the non-aromatic ring atoms are heteroatoms independently selected from O, S, or N; and the remaining ring atoms are carbon atoms. In certain embodiments, the heterocyclyl or heterocyclic group has from 3 to 20, from 3 to 15, from 3 to 10, from 3 to 8, from 4 to 7, or from 5 to 6 ring atoms. Heterocyclyl groups are bonded to the rest of the molecule through the non-aromatic ring. In certain embodiments, the heterocyclyl is a monocyclic, bicyclic, tricyclic, or tetracyclic ring system, which may include a fused or bridged ring system, and in which the nitrogen or sulfur atoms may be optionally oxidized, the nitrogen atoms may be optionally quaternized, and some rings may be partially or fully saturated, or aromatic. The heterocyclyl may be attached to the main structure at any heteroatom or carbon atom which results in the creation of a stable compound. Examples of such heterocyclic radicals include, but are not limited to, azepinyl, benzodioxanyl, benzodioxolyl, benzofuranonyl, benzopyranonyl, benzopyranyl, benzotetrahydrofuranyl, benzotetrahydrothienyl, benzothiopyranyl, benzoxazinyl, p-carbolinyl, chromanyl, chromonyl, cinnolinyl, coumarinyl, decahydroisoquinolinyl, dihydrobenzisothiazinyl, dihydrobenzisoxazinyl, dihydrofuryl, dihydroisoindolyl, dihydropyranyl, dihydropyrazolyl, dihydropyrazinyl, dihydropyridinyl, dihydropyrimidinyl, dihydropyrrolyl, dioxolanyl, 1,4-dithianyl, furanonyl, imidazolidinyl, imidazolinyl, indolinyl, isobenzotetrahydrofuranyl, isobenzotetrahydrothienyl, isochromanyl, isocoumarinyl, isoindolinyl, isothiazolidinyl, isoxazolidinyl, morpholinyl, octahydroindolyl, octahydroisoindolyl, oxazolidinonyl, oxazolidinyl, oxiranyl, piperazinyl, piperidinyl, 4-piperidonyl, pyrazolidinyl, pyrazolinyl, pyrrolidinyl, pyrrolinyl, quinuclidinyl, tetrahydrofuryl, tetrahydroisoquinolinyl, tetrahydropyranyl, tetrahydrothienyl, thiamorpholinyl, thiazolidinyl, tetrahydroquinolinyl, and 1,3,5-trithianyl. In certain embodiments, heterocyclic may also be optionally substituted as described herein.

The term "alkoxy" refers to an —OR radical, wherein R is, for example, alkyl, alkenyl, alkynyl, cycloalkyl, aryl, heteroaryl, or heterocyclyl, each as defined herein. Examples of alkoxy groups include, but are not limited to, methoxy, ethoxy, propoxy, n-propoxy, 2-propoxy, n-butoxy, isobutoxy, tert-butoxy, cyclohexyloxy, phenoxy, benzoxy, and 2-naphthyloxy. In certain embodiments, alkoxy may be optionally substituted as described herein. In certain embodiments, alkoxy is $C_{1-6}$ alkyl-oxy.

The term "halogen", "halide" or "halo" refers to fluorine, chlorine, bromine, and/or iodine.

The term "optionally substituted" is intended to mean that a group, such as an alkyl, alkenyl, alkynyl, cycloalkyl, aryl, heteroaryl, heterocyclyl, or alkoxy group, may be substituted with one or more substituents independently selected from, e.g., (a) alkyl, alkenyl, alkynyl, cycloalkyl, aryl, heteroaryl, and heterocyclyl, each optionally substituted with one or more, in one embodiment, one, two, three, or four, substituents Q; and (b) halo, cyano (—CN), nitro (—NO$_2$), —C(O)R$^a$, —C(O)OR$^a$, —C(O)NR$^b$R$^c$, —C(NR$^a$)NR$^b$R$^c$, —OR$^a$, —OC(O)R$^a$, —OC(O)OR$^a$, —OC(O)NR$^b$R$^c$, —OC(=NR$^a$)NR$^b$R$^c$, —OS(O)R$^a$, —OS(O)$_2$R$^a$, —OS(O)NR$^b$R$^c$, —OS(O)$_2$NR$^b$R$^c$, —NR$^b$R$^c$, —NR$^a$C(O)R$^d$, —NR$^a$C(O)OR$^d$, —NR$^a$C(O)NR$^b$R$^c$, —NR$^a$C(=NR$^d$)NR$^b$R$^c$, —NR$^a$S(O)R$^d$, —NR$^a$S(O)$_2$R$^d$, —NR$^a$S(O)NR$^b$R$^c$, —NR$^a$S(O)$_2$NR$^b$R$^c$, —SR$^a$, —S(O)R$^a$, —S(O)$_2$R$^a$, —S(O)NR$^b$R$^c$, and —S(O)$_2$NR$^b$R$^c$, wherein each R$^a$, R$^b$, R$^c$, and R$^d$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl, each optionally substituted with one or more, in one embodiment, one, two, three, or four, substituents Q; or (iii) R$^b$ and R$^c$ together with the N atom to which they are attached form heterocyclyl, optionally substituted with one or more, in one embodiment, one, two, three, or four, substituents Q. As used herein, all groups that can be substituted are "optionally substituted," unless otherwise specified.

In one embodiment, each Q is independently selected from the group consisting of (a) cyano, halo, and nitro; and (b) $C_{1-6}$ alkyl, $C_{2-6}$ alkenyl, $C_{2-6}$ alkynyl, $C_{3-7}$ cycloalkyl, $C_{6-14}$ aryl, heteroaryl, and heterocyclyl; and —C(O)R$^e$, —C(O)OR$^e$, —C(O)NR$^f$R$^g$, —C(NR$^e$)NR$^f$R$^g$, —OC(O)R$^e$, —OC(O)OR$^e$, —OC(O)NR$^f$R$^g$, —OC(=NR$^e$)NR$^f$R$^g$, —OS(O)R$^e$, —OS(O)$_2$R$^e$, —OS(O)NR$^f$R$^g$, —OS(O)$_2$NR$^f$R$^g$, —NR$^f$R$^g$, —NR$^e$C(O)R$^h$, —NR$^e$C(O)OR$^h$, —NR$^e$C(O)NR$^f$R$^g$, —NR$^e$C(=NR$^h$)NR$^f$R$^g$, —NR$^e$S(O)R$^h$, —NR$^e$S(O)$_2$R$^h$, —NR$^e$S(O)NR$^f$R$^g$, —NR$^e$S(O)$_2$NR$^f$R$^g$, —S(O)R$^e$, —S(O)$_2$R$^e$, —S(O)NR$^f$R$^g$, and —S(O)$_2$NR$^f$R$^g$; wherein each R$^e$, R$^f$, R$^g$, and R$^h$ is independently (i) hydrogen; (ii) $C_{1-6}$ alkyl, $C_{2-6}$ alkenyl, $C_{2-6}$ alkynyl, $C_{3-7}$ cycloalkyl, $C_{6-14}$ aryl, heteroaryl, or heterocyclyl; or (iii) R$^f$ and R$^g$ together with the N atom to which they are attached form heterocyclyl.

In certain embodiments, "optically active" and "enantiomerically active" refer to a collection of molecules, which has an enantiomeric excess of no less than about 50%, no less than about 70%, no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, the compound comprises about 95% or more of one enantiomer and about 5% or less of the other enantiomer based on the total weight of the racemate in question.

In describing an optically active compound, the prefixes R and S are used to denote the absolute configuration of the molecule about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the molecule, R and S.

The term "solvate" refers to a compound provided herein or a salt thereof, which further includes a stoichiometric or non-stoichiometric amount of solvent bound by non-covalent intermolecular forces. Where the solvent is water, the solvate is a hydrate.

The term "naturally occurring" or "native" when used in connection with biological materials such as nucleic acid molecules, polypeptides, host cells, and the like, refers to materials which are found in nature and are not manipulated by man. Similarly, "non-naturally occurring" or "non-native" refers to a material that is not found in nature or that has been structurally modified or synthesized by man.

The term "CCR3" refers to CC chemokine receptor 3 or a variant thereof, which is capable of mediating a cellular response to a variety of chemokines, including, but not limited to, eotaxin (CCL11), eotaxin-3 (CCL26), MCP-3 (CCL7), MCP-4 (CCL13), and RANTES (CCL5). CCR3 variants include proteins substantially homologous to a native CCR3, i.e., proteins having one or more naturally or non-naturally occurring amino acid deletions, insertions or substitutions (e.g., CCR3 derivatives, homologs and fragments), as compared to the amino acid sequence of a native CCR3. The amino acid sequence of a CCR3 variant is at least about 80% identical, at least about 90% identical, or at least about 95% identical to a native CCR3.

The term "CCR3 antagonist" refers to a compound that, e.g., partially or totally blocks, decreases, prevents, inhibits, or downregulates CCR3 activity. The term "CCR3 antagonist" also refers to a compound that binds to, delays the activation of, inactivates, or desensitizes a CCR3 receptor. A CCR3 antagonist may act by interfering with the interaction of a CCR3 receptor and its chemokine ligand, including, but not limited to, eotaxin (CCL11), eotaxin-3 (CCL26), MCP-3 (CCL7), MCP-4 (CCL13), and/or RANTES (CCL5).

The terms "CCR3-mediated disorder or disease" and "a condition, disorder or disease mediated by CCR3" refer to a condition, disorder, or disease characterized by inappropriate, e.g., less than or greater than normal, CCR3 activity. Inappropriate CCR3 functional activity might arise as the result of CCR3 expression in cells which normally do not express CCR3, increased CCR3 expression or degree of intracellular activation, leading to, e.g., inflammatory and immune-related disorders or diseases; or decreased CCR3 expression. A CCR3-mediated condition, disorder or disease may be completely or partially mediated by inappropriate CCR3 activity. In particular, a CCR3-mediated condition, disorder or disease is one in which modulation of a CCR3 receptor results in some effect on the underlying condition or disorder, e.g., a CCR3 antagonist or agonist results in some improvement in at least some of patients being treated.

Compounds

Provided herein are 2,5-disubstituted arylsulfonamides which are useful for modulating CCR3 activity. Also provided herein are pharmaceutical compositions which comprise the compounds and methods of use of the compounds and compositions for the treatment of a CCR3-mediated disorder, disease, or condition.

In one embodiment, provided herein is a 2,5-disubstituted arylsulfonamide of Formula I:

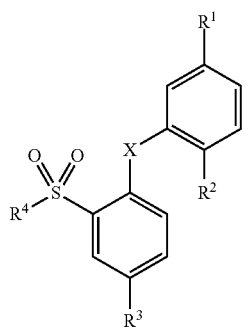

(I)

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof;

wherein:

$R^1$ and $R^2$ are each independently (a) halo, cyano, nitro, hydroxyl, or guanidine; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, phenyl, benzyl, phenoxy, benzoxy, or heterocyclyl; or (d) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;

$R^3$ is (a) hydrogen, halo, cyano, nitro, or hydroxyl; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, or tetrazolyl; or (d) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;

$R^4$ is

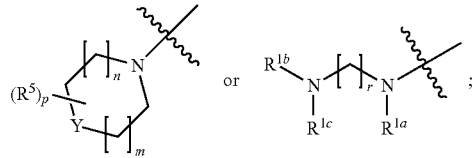

$R^5$ is (a) halo, cyano, nitro, hydroxyl, oxo, or guanidine; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, phenyl, benzyl, phenoxy, benzoxy, or heterocyclyl; or (d) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)$R^{1d}$, —N$R^{1a}$S(O)$_2R^{1d}$, —S(O)$R^{1a}$, —S(O)$_2R^{1a}$, —S(O)N$R^{1b}R^{1c}$, or —S(O)$_2$N$R^{1b}R^{1c}$;

X is O or S;

Y is —O—, —S—, —S(O)—, —S(O)$_2$—, —N($R^{1a}$)—, —C($R^{1a}$)($R^{1d}$)—, or —C($R^{1a}$)(N$R^{1b}R^{1c}$)—;

m is an integer from 0 to 3;

n is an integer from 1 to 3;

p is an integer from 0 to 4;

r is an integer from 1 to 6; and each $R^{1a}$, $R^{1b}$, $R^{1c}$, and $R^{1d}$ is independently (a) hydrogen, phenyl, or benzyl; (b) $C_{3-7}$ cycloalkyl, heteroaryl, or heterocyclyl, each optionally substituted; or (c) $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; or each pair of $R^{1b}$ and $R^{1c}$ together with the N atom to which they are attached independently form heteroaryl or heterocyclyl;

with the proviso that when X is O; Y is —N($R^{1a}$)—; m and n are 1; $R^1$ and $R^2$ are each independently chloro, nitro, methyl, or isopropyl; $R^3$ is nitro; and p is 0; then $R^{1a}$ is not hydrogen.

In one embodiment, in Formula I, $R^1$ and $R^2$ are each independently (a) halo, cyano, nitro, hydroxyl, or guanidine; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, phenyl, benzyl, phenoxy, benzoxy, or heterocyclyl; or (d) —C(O)$R^{1a}$, —C(O)O$R^{1a}$, —C(O)N$R^{1b}R^{1c}$, —OC(O)N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$S(O)$_2R^{1d}$, —S(O)$_2R^{1a}$, or —S(O)$_2$N$R^{1b}R^{1c}$;

$R^3$ is (a) hydrogen, halo, cyano, nitro, or hydroxyl; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, or tetrazolyl; or (d) —C(O)$R^{1a}$, —C(O)O$R^{1a}$, —C(O)NR$^{1b}$R$^{1c}$, —OC(O)NR$^{1b}$R$^{1c}$, —NR$^{1b}$R$^{1c}$, —NR$^{1a}$C(O)R$^{1d}$, or —NR$^{1a}$C(O)OR$^{1d}$;

R$^4$ is

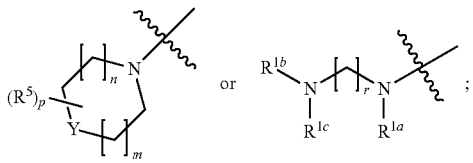

R$^5$ is (a) halo, cyano, nitro, hydroxyl, oxo, or guanidine; (b) C$_{1-6}$ alkyl, C$_{1-6}$ alkoxy, or C$_{1-6}$ alkylthio, wherein the alkyl, alkoxy, and alkylthio are each independently and optionally substituted with one, two, or three halo; (c) alkenyl. C$_{2-6}$ alkynyl, phenyl, benzyl, phenoxy, benzoxy, or heterocyclyl; or (d) —C(O)R$^{1a}$, —C(O)OR$^{1a}$, —C(O)NR$^{1b}$R$^{1c}$, —OC(O)NR$^{1b}$NR$^{1c}$, —NR$^{1b}$R$^{1c}$, —NR$^{1a}$C(O)R$^{1d}$, —NR$^{1a}$C(O)OR$^{1d}$, —NR$^{1a}$S(O)$_2$R$^{1d}$, —S(O)$_2$R$^{1a}$, or —S(O)$_2$NR$^{1b}$R$^{1c}$;

X is O or S;
Y is —O—, —S—, —S(O)—, —S(O)$_2$—, N(R$^{1a}$)—, C(R$^{1a}$)(R$^{1d}$)—, or —C(R$^{1a}$)(NR$^{1b}$R$^{1c}$)—;
m is an integer from 0 to 3;
n is an integer from 1 to 3;
p is an integer from 0 to 4;
r is an integer from 1 to 6; and each R$^{1a}$ and R$^{1d}$ is independently (a) hydrogen, phenyl, or benzyl; (b) C$_{3-7}$ cycloalkyl, heteroaryl, or heterocyclyl, each optionally substituted; or (c) C$_{1-6}$ alkyl, optionally substituted with one, two, or three substituents, each independently selected from halo, hydroxyl, carboxy, alkoxy, carbamoyl, C$_{6-14}$ aryl, C$_{1-6}$ alkylcarbamoyl, di(C$_{1-6}$ alkyl)carbamoyl, C$_{3-7}$ cycloalkylcarbamoyl, and C$_{3-7}$ heterocyclylcarbamoyl; and each R$^{1b}$ and R$^{1c}$ is independently (a) hydrogen or phenyl; or (b) C$_{1-6}$ alkyl, optionally substituted with one, two, or three substituents, each independently selected from halo, hydroxyl, carboxy, alkoxy, carbamoyl, C$_{6-14}$ aryl, C$_{1-6}$ alkylcarbamoyl, alkyl)carbamoyl, C$_{3-7}$ cycloalkylcarbamoyl, and C$_{3-7}$ heterocyclylcarbamoyl; or each pair of R$^{1b}$ and R$^{1c}$ together with the N atom to which they are attached independently form heteroaryl or heterocyclyl;

with the proviso that when X is O; Y is —N(R$^{1a}$)—; m and n are 1; R$^1$ and R$^2$ are each independently chloro, nitro, methyl, or isopropyl; R$^3$ is nitro; and p is 0; then R$^{1a}$ is not hydrogen.

In another embodiment, in Formula I,
R$^1$ and R$^2$ are each independently halo or C$_{1-6}$ alkyl, optionally substituted with one, two, or three halo;
R$^3$ is cyano or nitro;
R$^4$ is

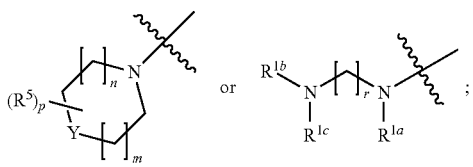

R$^5$ is C$_{1-6}$ alkyl, optionally substituted with one, two, or three halo;

X is O or S;
Y is —O—, —N(R$^{1a}$)—, —C(R$^{1a}$)(R$^{1d}$)—, or C(R$^{1a}$)(NR$^{1b}$R$^{1c}$)—;
m is 1;
n is 1 or 2;
p is 0, 1, or 2;
r is 2;

each R$^{1a}$ and R$^{1d}$ is independently (a) hydrogen; (b) C$_{3-7}$ cycloalkyl, heteroaryl, or heterocyclyl, each optionally substituted; or (c) C$_{1-6}$ alkyl, optionally substituted with one, two, or three substituents, each independently selected from halo, hydroxyl, carboxy, alkoxy, carbamoyl, C$_{6-14}$ aryl, C$_{1-6}$ alkylcarbamoyl, di(C$_{1-6}$ alkyl)carbamoyl, C$_{3-7}$ cycloalkylcarbamoyl, and C$_{3-7}$ heterocyclylcarbamoyl; and each R$^{1b}$ and R$^{1c}$ is independently C$_{1-6}$ alkyl, optionally substituted with one, two, or three substituents, each independently selected from halo, hydroxyl, carboxy, alkoxy, carbamoyl, C$_{6-14}$ aryl, C$_{1-6}$ alkylcarbamoyl, di(C$_{1-6}$ alkyl)carbamoyl, C$_{3-7}$ cycloalkylcarbamoyl, and C$_{3-7}$ heterocyclylcarbamoyl; or each pair of R$^{1b}$ and R$^{1c}$ together with the N atom to which they are attached independently form heterocyclyl; and with the proviso that when X is O; Y is —N(R$^{1a}$)—; m and n are 1; R$^1$ and R$^2$ are each independently chloro, nitro, methyl, or isopropyl; R$^3$ is nitro, and p is 0; then R$^{1a}$ is not hydrogen.

In yet another embodiment, in Formula I,
R$^1$ and R$^2$ are each independently halo or C$_{1-6}$ alkyl;
R$^3$ is cyano or nitro;
R$^4$ is

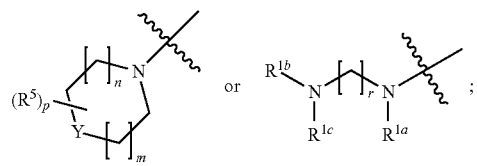

R$^5$ is C$_{1-6}$ alkyl;
X is O or S;
Y is —O—, —N(R$^{1a}$)—, —C(R$^{1a}$)(R$^{1d}$)—, or —C(R$^{1a}$)(NR$^{1b}$R$^{1c}$)—;
m is 1;
n is 1 or 2;
p is 0, 1, or 2;
r is 2;

each R$^{1a}$ and R$^{1d}$ is independently hydrogen, C$_{3-7}$ cycloalkyl, heterocyclyl, or C$_{1-6}$ alkyl; and each R$^{1b}$ and R$^{1c}$ is independently C$_{1-6}$ alkyl; or each pair of R$^{1b}$ and R$^{1c}$ together with the N atom to which they are attached independently form heterocyclyl; and with the proviso that when X is O; Y is —N(R$^{1a}$)—; m and n are 1; R$^1$ and R$^2$ are each independently chloro, nitro, methyl, or isopropyl; R$^3$ is nitro; and p is 0; then R$^{1a}$ is not hydrogen.

In yet another embodiment, in Formula I,
R$^1$ and R$^2$ are each independently fluoro, chloro, methyl, ethyl, propyl (e.g., n-propyl or isopropyl), or butyl (e.g., n-butyl, 2-butyl, isobutyl, or t-butyl);
R$^3$ is cyano or nitro;

$R^4$ is

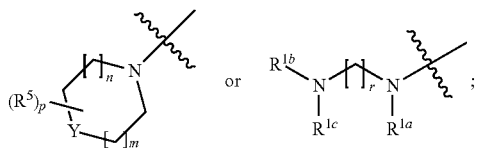

$R^5$ is methyl;
X is O or S;
Y is —O—, —N($R^{1a}$)—, —C($R^{1a}$)($R^{1d}$)—, or —C($R^{1a}$)(N$R^{1b}R^{1c}$)—;
m is 1;
n is 1 or 2;
p is 0, 1, or 2;
r is 2;
each $R^{1a}$ is hydrogen, methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl), cyclopentyl, or 3-oxo-1H-imidazo[1,5-c]imidazol-2(3H)-yl;
each $R^{1b}$ and $R^{1c}$ is independently methyl or ethyl; or each pair of $R^{1b}$ and $R^{1c}$ together with the N atom to which they are attached independently form pyrrolidinyl or piperidinyl; and
$R^{1d}$ is hydrogen;
with the proviso that when X is O; Y is —N($R^{1a}$)—; m and n are 1; $R^1$ and $R^2$ are each independently chloro, nitro, methyl, or isopropyl; $R^3$ is nitro; and p is 0; then $R^{1a}$ is not hydrogen.

In still another embodiment, in Formula I,
$R^1$ and $R^2$ are each independently fluoro, chloro, or methyl;
$R^3$ is cyano or nitro;
$R^4$ is

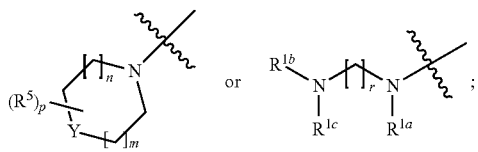

$R^5$ is methyl;
X is O or S;
Y is —O—, —N($R^{1a}$)—, —C($R^{1a}$)($R^{1d}$)—, or —C($R^{1a}$)(N$R^{1b}R^{1c}$)—;
m is 1;
n is 1 or 2;
p is 0, 1, or 2;
r is 2;
each $R^{1a}$ is hydrogen, methyl, isopropyl, 2-pentyl, 3-pentyl, cyclopentyl, or 5-butyl-7-chloro-3-oxo-1H-imidazo[1,5-c]imidazol-2(3H)-yl;
each $R^{1b}$ and $R^{1c}$ is independently methyl or ethyl; or each pair of $R^{1b}$ and $R^{1c}$ together with the N atom to which they are attached independently form pyrrolidinyl or piperidinyl;
$R^{1d}$ is hydrogen; with the proviso that when X is O; Y is —N($R^{1a}$)—; m and n are 1; $R^1$ and $R^2$ are each independently chloro, nitro, methyl, or isopropyl; $R^3$ is nitro; and p is 0; then $R^{1a}$ is not hydrogen.

In one embodiment, in Formula I,
$R^1$ and $R^2$ are each independently halo or $C_{1-6}$ alkyl, optionally substituted with one, two, or three halo;
$R^3$ is cyano or nitro;
$R^4$ is

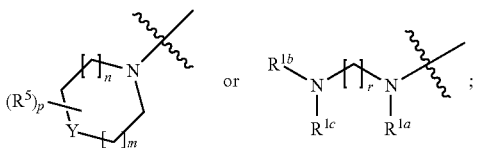

$R^5$ is oxo; $C_{1-6}$ alkyl, optionally substituted with one, two, or three halo; or —C(O)O$R^{1a}$;
X is O or S;
Y is —O—, —S—, —S(O)$_2$—, —N($R^{1a}$)—, —C($R^{1a}$)($R^{1d}$)—, or —C($R^{1a}$)(N$R^{1b}R^{1c}$)—;
m is 1;
n is 1 or 2;
p is 0, 1, or 2;
r is 2;
each $R^{1a}$ and $R^{1d}$ is independently (a) hydrogen; (b) $C_{3-7}$ cycloalkyl, heteroaryl, or heterocyclyl, each optionally substituted; or (c) $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; and
each $R^{1b}$ and $R^{1c}$ is independently $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; or
each pair of $R^{1b}$ and $R^{1c}$ together with the N atom to which they are attached independently form heterocyclyl; and
with the proviso that when X is O; Y is —N($R^{1a}$)—; m and n are 1; $R^1$ and $R^2$ are each independently chloro, nitro, methyl, or isopropyl; $R^3$ is nitro, and p is 0; then $R^{1a}$ is not hydrogen.

In another embodiment, in Formula I,
$R^1$ and $R^2$ are each independently halo or $C_{1-6}$ alkyl;
$R^3$ is cyano or nitro;
$R^4$ is

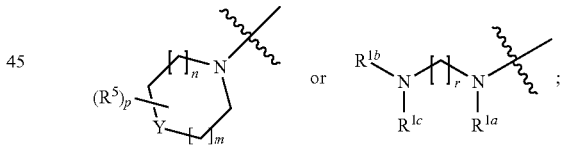

$R^5$ is oxo, $C_{1-6}$ alkyl, or C(O)O$R^{1a}$, wherein $R^{1a}$ is $C_{1-6}$ alkyl;
X is O or S;
Y is —O—, —S—, —S(O)$_2$—, —N($R^{1a}$)—, —C($R^{1a}$)($R^{1d}$)—, or —C($R^{1a}$)(N$R^{1b}R^{1c}$)—;
m is 1;
n is 1 or 2;
p is 0, 1, or 2;
r is 2;
each $R^{1a}$ and $R^{1d}$ is independently hydrogen, $C_{3-7}$ cycloalkyl, heterocyclyl, or $C_{1-6}$ alkyl; and
each $R^{1b}$ and $R^{1c}$ is independently $C_{1-6}$ alkyl; or each pair of $R^{1b}$ and $R^{1c}$ together with the N atom to which they are attached independently form heterocyclyl; and
with the proviso that when X is O; Y is —N($R^{1a}$)—; m and n are 1; $R^1$ and $R^2$ are each independently chloro, nitro, methyl, or isopropyl; $R^3$ is nitro; and p is 0; then $R^{1a}$ is not hydrogen.

In yet another embodiment, in Formula I, $R^1$ and $R^2$ are each independently fluoro, chloro, methyl, ethyl, propyl (e.g., n-propyl or isopropyl), or butyl (e.g., n-butyl, 2-butyl, isobutyl, or t-butyl);

$R^3$ is cyano or nitro;

$R^4$ is

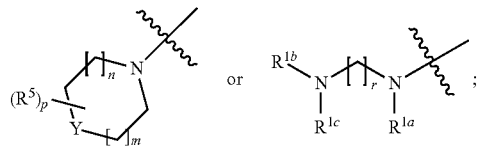

$R^5$ is methyl, oxo, or methoxycarbonyl;

X is O or S;

Y is —O—, —S—, —S(O)$_2$—, —C($R^{1a}$)($R^{1d}$)—, or C($R^{1a}$)(N$R^{1b}R^{1c}$)—;

m is 1;

n is 1 or 2;

p is 0, 1, or 2;

r is 2;

each $R^{1a}$ is hydrogen, methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl), cyclopentyl, or 3-oxo-1H-imidazo[1,5-c]imidazol-2(3H)-yl;

each $R^{1b}$ and $R^{1c}$ is independently methyl or ethyl; or each pair of $R^{1b}$ and $R^{1c}$ together with the N atom to which they are attached independently form pyrrolidinyl or piperidinyl; and $R^{1d}$ is hydrogen;

with the proviso that when X is O; Y is —N($R^{1a}$)—; m and n are 1; $R^1$ and $R^2$ are each independently chloro, nitro, methyl, or isopropyl; $R^3$ is nitro; and p is 0; then $R^{1a}$ is not hydrogen.

In still another embodiment, in Formula I, $R^1$ and $R^2$ are each independently fluoro, chloro, or methyl;

$R^3$ is cyano or nitro;

$R^4$ is

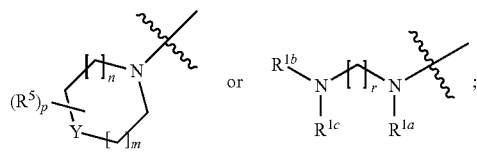

$R^5$ is methyl, oxo, or methoxycarbonyl;

X is O or S;

Y is —O—, —S—, —S(O)$_2$—, —N($R^{1a}$)—, —C($R^{1a}$)($R^{1d}$)—, or —C($R^{1a}$)(N$R^{1b}R^{1c}$)—;

m is 1;

n is 1 or 2;

p is 0, 1, or 2;

r is 2;

each $R^{1a}$ is hydrogen, methyl, ethyl, isopropyl, 2-pentyl, 3-pentyl, cyclopentyl, cyclohexyl, or 5-butyl-7-chloro-3-oxo-1H-imidazo[1,5-c]imidazol-2(3H)-yl;

each $R^{1b}$ and $R^{1c}$ is independently methyl or ethyl; or each pair of $R^{1b}$ and $R^{1c}$ together with the N atom to which they are attached independently form pyrrolidinyl or piperidinyl;

$R^{1d}$ is hydrogen;

with the proviso that when X is O; Y is —N($R^{1a}$)—; m and n are 1; $R^1$ and $R^2$ are each independently chloro, nitro, methyl, or isopropyl; $R^3$ is nitro; and p is 0; then $R^{1a}$ is not hydrogen.

In another embodiment, the arylsulfonamide of Formula I has the structure of Formula II:

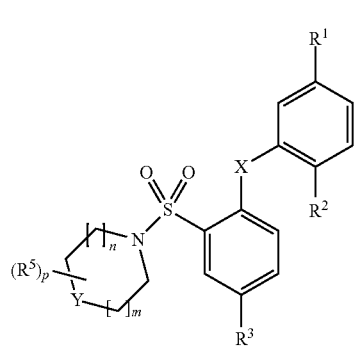

(II)

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof; wherein $R^1$, $R^2$, $R^3$, $R^5$, X, Y, n, and p are each as defined herein.

In one embodiment, in Formula II, $R^1$ and $R^2$ are each independently (a) halo, cyano, nitro, hydroxyl, or guanidine; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, phenyl, benzyl, phenoxy, benzoxy, or heterocyclyl; or (d) —C(O)$R^{1a}$, —C(O)O$R^{1a}$, —C(O)N$R^{1b}R^{1c}$, —OC(O)N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$S(O)$_2R^{1d}$, —S(O)$_2R^{1a}$, or S(O)$_2$N$R^{1b}R^{1c}$;

$R^3$ is (a) hydrogen, halo, cyano, nitro, or hydroxyl; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, or tetrazolyl; or (d) —C(O)$R^{1a}$, —C(O)O$R^{1a}$, —C(O)N$R^{1b}R^{1c}$, —OC(O)N$R^{1b}R^{1c}$, N$R^{1b}R^{1c}$, —N$R^{1a}$C(O)$R^{1d}$, or —N$R^{1a}$C(O)O$R^{1d}$;

$R^5$ is (a) halo, cyano, nitro, hydroxyl, oxo, or guanidine; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, phenyl, benzyl, phenoxy, benzoxy, or heterocyclyl; or (d) C(O)$R^{1a}$, —C(O)O$R^{1a}$, —C(O)N$R^{1b}R^{1c}$, —OC(O)N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$S(O)$_2R^{1d}$, —S(O)$_2R^{1a}$, or S(O)$_2$N$R^{1b}R^{1c}$;

X is O or S;

Y is —O—, —S—, —S(O)—, —S(O)$_2$—, —N($R^{1a}$)—, C($R^{1a}$)($R^{1d}$)—, or —C($R^{1d}$)(N$R^{1b}R^{1c}$)—;

m is an integer from 0 to 3;

n is an integer from 1 to 3;

p is an integer from 0 to 4;

each $R^{1a}$ and $R^{1d}$ is independently (a) hydrogen, phenyl, or benzyl; (b) $C_{3-7}$ cycloalkyl, heteroaryl, or heterocyclyl, each optionally substituted; or (c) $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; and each $R^{1b}$ and $R^{1c}$ is independently (a) hydrogen or phenyl; or (b) $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; or each pair of $R^{1b}$ and $R^{1c}$ together with the N atom to which they are attached independently form heteroaryl or heterocyclyl;

with the proviso that when X is O; Y is —N($R^{1a}$)—; m and n are 1; $R^1$ and $R^2$ are each independently chloro, nitro, methyl, or isopropyl; $R^3$ is nitro; and p is 0; then $R^{1a}$ is not hydrogen.

In another embodiment, in Formula II, $R^1$ and $R^2$ are each independently halo or $C_{1-6}$ alkyl, optionally substituted with one, two, or three halo;

$R^3$ is cyano or nitro;

$R^5$ is $C_{1-6}$ alkyl, optionally substituted with one, two, or three halo;

X is O or S;

Y is —O—, —N($R^{1a}$)—, —C($R^{1a}$)($R^{1d}$)—, or C($R^{1a}$)(N$R^{1b}R^{1c}$)—;

m is 1;

n is 1 or 2;

p is 0, 1, or 2;

each $R^{1a}$ and $R^{1d}$ is independently (a) hydrogen; (b) $C_{3-7}$ cycloalkyl, heteroaryl, or heterocyclyl, each optionally substituted; or (c) $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, alkyl)carbamoyl, $C_{3-7}$ cycloalkylcarbamoyl, and $C_{3-7}$ heterocyclylcarbamoyl; and $R^{1b}$ and $R^{1c}$ are each independently $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; or $R^{1b}$ and $R^{1c}$ together with the N atom to which they are attached form heterocyclyl;

with the proviso that when X is O; Y is —N($R^{1a}$)—; m and n are 1; $R^1$ and $R^2$ are each independently chloro, nitro, methyl, or isopropyl; $R^3$ is nitro; and p is 0; $R^{1a}$ is not hydrogen.

In yet another embodiment, in Formula II, $R^1$ and $R^2$ are each independently halo or $C_{1-6}$ alkyl;

$R^3$ is cyano or nitro;

$R^5$ is $C_{1-6}$ alkyl;

X is O or S;

Y is —O—, —N($R^{1a}$)—, —C($R^{1a}$)($R^{1d}$)—, or —C($R^{1a}$)(N$R^{1b}R^{1c}$)—;

m is 1;

n is 1 or 2;

p is 0, 1, or 2;

each $R^{1a}$ and $R^{1d}$ is independently hydrogen, $C_{3-7}$ cycloalkyl, heterocyclyl, or $C_{1-6}$ alkyl; and $R^{1b}$ and $R^{1c}$ are each independently $C_{1-6}$ alkyl; or $R^{1b}$ and $R^{1c}$ together with the N atom to which they are attached form heterocyclyl;

with the proviso that when X is O; Y is —N($R^{1a}$)—; m and n are 1; $R^1$ and $R^2$ are each independently chloro, nitro, methyl, or isopropyl; $R^3$ is nitro; and p is 0; $R^{1a}$ is not hydrogen.

In yet another embodiment, in Formula II, $R^1$ and $R^2$ are each independently fluoro, chloro, or methyl;

$R^3$ is cyano or nitro;

$R^5$ is methyl;

X is O or S;

Y is —O—, —N($R^{1a}$)—, —C($R^{1a}$)($R^{1d}$)—, or —C($R^{1a}$)(N$R^{1b}R^{1c}$)—;

m is 1;

n is 1 or 2;

p is 0, or 2;

each $R^{1a}$ is hydrogen, methyl, ethyl, propyl (e.g., n-propyl or isopropyl), butyl (e.g., n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl), cyclopentyl, or 3-oxo-1H-imidazo[1,5-c]imidazol-2(3H)-yl;

each $R^{1b}$ and $R^{1c}$ is independently methyl or ethyl; or each pair of $R^{1b}$ and $R^{1c}$ together with the N atom to which they are attached independently form pyrrolidinyl or piperidinyl; and $R^{1d}$ is hydrogen;

with the proviso that when X is O; Y is —N($R^{1a}$)—; m and n are 1; $R^1$ and $R^2$ are each independently chloro, nitro, methyl, or isopropyl; $R^3$ is nitro; and p is 0; $R^{1a}$ is not hydrogen.

In still another embodiment, in Formula II, $R^1$ and $R^2$ are each independently fluoro, chloro, or methyl;

$R^3$ is cyano or nitro;

$R^5$ is methyl;

X is O or S;

Y is —O—, —N($R^{1a}$)—, C($R^{1a}$)($R^{1d}$)—, or —C($R^{1a}$)(N$R^{1b}R^{1c}$)—;

m is 1;

n is 1 or 2;

p is 0, 1, or 2;

each $R^{1a}$ is hydrogen, methyl, isopropyl, 2-pentyl, 3-pentyl, cyclopentyl, or 5-butyl-7-chloro-3-oxo-1H-imidazo[1,5-c]imidazol-2(3H)-yl;

each $R^{1b}$ and $R^{1c}$ is independently methyl or ethyl; or each pair of $R^{1b}$ and $R^{1c}$ together with the N atom to which they are attached independently form pyrrolidinyl or piperidinyl;

$R^{1d}$ is hydrogen;

with the proviso that when X is O; Y is —N($R^{1a}$)—; m and n are 1; $R^1$ and $R^2$ are each independently chloro, nitro, methyl, or isopropyl; $R^3$ is nitro; and p is 0; $R^{1a}$ is not hydrogen.

In one embodiment, in Formula II, $R^1$ and $R^2$ are each independently halo or $C_{1-6}$ alkyl, optionally substituted with one, two, or three halo;

$R^3$ is cyano or nitro;

$R^5$ is oxo; $C_{1-6}$ alkyl, optionally substituted with one, two, or three halo; or —C(O)O$R^{1a}$;

X is O or S;

Y is —O—, —S—, —S(O)$_2$—, —N($R^{1a}$)—, —C($R^{1a}$)($R^{1d}$)—, or —C($R^{1a}$)(N$R^{1b}R^{1c}$)—;

m is 1;

n is 1 or 2;

p is 0, 1, or 2;

each $R^{1a}$ and $R^{1d}$ is independently (a) hydrogen; (b) $C_{3-7}$ cycloalkyl, heteroaryl, or heterocyclyl, each optionally substituted; or (c) $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; and $R^{1b}$ and $R^{1c}$ are each independently $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; or $R^{1b}$ and $R^{1c}$ together with the N atom to which they are attached form heterocyclyl;

with the proviso that when X is O; Y is —N($R^{1a}$)—; m and n are 1; $R^1$ and $R^2$ are each independently chloro, nitro, methyl, or isopropyl; $R^3$ is nitro; and p is 0; $R^{1a}$ is not hydrogen.

In another embodiment, in Formula II, $R^1$ and $R^2$ are each independently halo or $C_{1-6}$ alkyl;

$R^3$ is cyano or nitro;

$R^5$ is oxo, $C_{1-6}$ alkyl, or —C(O)O$R^{1a}$, wherein $R^{1a}$ is $C_{1-6}$ alkyl;

X is O or S;

Y is —O—, —S—, —S(O)$_2$—, —N($R^{1a}$)—, —C($R^{1a}$)($R^{1d}$)—, or —($R^{1a}$)(N$R^{1b}R^{1c}$)—;

m is 1;

n is 1 or 2;

p is 0, 1, or 2;

each $R^{1a}$ and $R^{1d}$ is independently hydrogen, $C_{3-7}$ cycloalkyl, heterocyclyl, or $C_{1-6}$ alkyl; and $R^{1b}$ and $R^{1c}$ are each independently $C_{1-6}$ alkyl; or $R^{1b}$ and $R^{1c}$ together with the N atom to which they are attached form heterocyclyl;

with the proviso that when X is O; Y is —N($R^{1a}$)—; m and n are 1; $R^1$ and $R^2$ are each independently chloro, nitro, methyl, or isopropyl; $R^3$ is nitro; and p is 0; $R^{1a}$ is not hydrogen.

In yet another embodiment, in Formula II, $R^1$ and $R^2$ are each independently fluoro, chloro, or methyl;

$R^3$ is cyano or nitro;

$R^5$ is methyl, oxo, or methoxycarbonyl;

X is O or S;

Y is —O—, —S—, —S(O)$_2$—, —N($R^{1a}$)—, —C($R^{1a}$)($R^{1d}$)—, or —C($R^{1a}$)(N$R^{1b}R^{1c}$)—;

m is 1;

n is 1 or 2;

p is 0, 1, or 2;

each $R^{1a}$ is hydrogen, methyl, ethyl, propyl (e.g., n-propyl or isopropyl), butyl n-butyl, 2-butyl, isobutyl, or t-butyl), pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl), cyclopentyl, or 3-oxo-1H-imidazo[1,5-c]imidazol-2(3H)-yl;

each $R^{1b}$ and $R^{1c}$ is independently methyl or ethyl; or each pair of $R^{1b}$ and $R^{1c}$ together with the N atom to which they are attached independently form pyrrolidinyl or piperidinyl; and $R^{1d}$ is hydrogen;

with the proviso that when X is O; Y is —N($R^{1a}$)—; m and n are 1; $R^1$ and $R^2$ are each independently chloro, nitro, methyl, or isopropyl; $R^3$ is nitro; and p is 0; $R^{1a}$ is not hydrogen.

In still another embodiment, in Formula II, $R^1$ and $R^2$ are each independently fluoro, chloro, or methyl;

$R^3$ is cyano or nitro;

$R^5$ is methyl, oxo, or methoxycarbonyl;

X is O or S;

Y is —O—, —S—, —S(O)$_2$—, —N($R^{1a}$)—, —C($R^{1a}$)($R^{1d}$)—, or —C($R^{1a}$)(N$R^{1b}R^{1c}$)—;

m is 1;

n is 1 or 2;

p is 0, 1, or 2;

each $R^{1a}$ is hydrogen, methyl, isopropyl, 2-pentyl, 3-pentyl, cyclopentyl, or 5-butyl-7-chloro-3-oxo-1H-imidazo[1,5-c]imidazol-2(3H)-yl;

each $R^{1b}$ and $R^{1c}$ is independently methyl or ethyl; or each pair of $R^{1b}$ and $R^{1c}$ together with the N atom to which they are attached independently form pyrrolidinyl or piperidinyl;

$R^{1d}$ is hydrogen;

with the proviso that when X is O; Y is —N($R^{1a}$)—; m and n are 1; $R^1$ and $R^2$ are each independently chloro, nitro, methyl, or isopropyl; $R^3$ is nitro; and p is 0; $R^{1a}$ is not hydrogen.

In yet another embodiment, the arylsulfonamide of Formula I has the structure of Formula III:

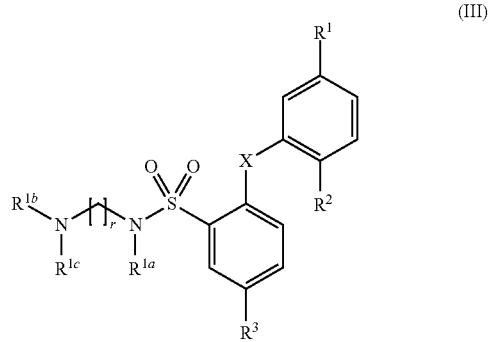

(III)

or an enantiomer, a mixture of enantiomers, a mixture of two or more diastereomers, a tautomer, or a mixture of two or more tautomers thereof; or a pharmaceutically acceptable salt, solvate, hydrate, or prodrug thereof; wherein $R^1$, $R^2$, $R^3$, $R^{1a}$, $R^{1b}$, $R^{1c}$, X, and r are each as defined herein.

In one embodiment, in Formula III, $R^1$ and $R^2$ are each independently (a) halo, cyano, nitro, hydroxyl, or guanidine; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, phenyl, benzyl, phenoxy, benzoxy, or heterocyclyl; or (d) —C(O)$R^{1a}$, —C(O)O$R^{1a}$, —C(O)N$R^{1b}R^{1c}$, —OC(O)N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$S(O)$_2R^{1d}$, —S(O)$_2R^{1a}$, or —S(O)$_2$N$R^{1b}R^{1c}$;

$R^3$ is (a) hydrogen, halo, cyano, nitro, or hydroxyl; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, or tetrazolyl; or (d) —C(O)$R^{1a}$, —C(O)O$R^{1a}$, —C(O)N$R^{1b}R^{1c}$, —OC(O)N$R^{1b}R^{1c}$, —N$R^{1b}R^{1c}$, —N$R^{1a}$C(O)$R^{1d}$, or —N$R^{1a}$C(O)O$R^{1d}$;

X is O or S;

r is an integer from 1 to 6;

each $R^{1a}$ and $R^{1d}$ is independently (a) hydrogen, phenyl, or benzyl; (b) $C_{3-7}$ cycloalkyl; or (c) $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; and each $R^{1b}$ and $R^{1c}$ is independently (a) hydrogen or phenyl; or (b) $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; or each pair of $R^{1b}$ and $R^{1c}$ together with the N atom to which they are attached independently form heteroaryl or heterocyclyl.

In another embodiment, in Formula III, $R^1$ and $R^2$ are each independently halo or $C_{1-6}$ alkyl, optionally substituted with one, two, or three halo;

$R^3$ is cyano or nitro;

X is O or S;

r is 2;

$R^{1a}$ is (a) hydrogen; or (b) $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; and $R^{1b}$ and $R^{1c}$ are each independently $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; or $R^{1b}$ and $R^{1c}$ together with the N atom to which they are attached form heterocyclyl.

In yet another embodiment, in Formula III, $R^1$ and $R^2$ are each independently halo or $C_{1-6}$ alkyl;

$R^3$ is cyano or nitro;

X is O or S;

r is 2;

$R^{1a}$ is hydrogen; and $R^{1b}$ and $R^{1c}$ are each independently $C_{1-6}$ alkyl; or $R^{1b}$ and $R^{1c}$ together with the N atom to which they are attached form heterocyclyl.

In still another embodiment, in Formula III, $R^1$ and $R^2$ are each independently fluoro or methyl;

$R^3$ is cyano;

X is O or S;

r is 2;

$R^{1a}$ is hydrogen; and $R^{1b}$ and $R^{1c}$ are ethyl; or $R^{1b}$ and $R^{1c}$ together with the N atom to which they are attached independently form pyrrolidinyl or piperidinyl.

The groups, $R^1$, $R^2$, $R^3$, $R^4$, $R^5$, $R^{1a}$, $R^{1b}$, $R^{1c}$, $R^{1d}$, X, Y, m, n, p, and r in Formula I, II, or III are further defined in the embodiments described herein. All combinations of the embodiments provided herein for such groups are within the scope of this disclosure.

In certain embodiments, $R^1$ is halo, cyano, nitro, hydroxyl, or guanidine. In certain embodiments, $R^1$ is halo. In certain embodiments, $R^1$ is fluoro or chloro. In certain embodiments, $R^1$ is $C_{1-6}$ alkyl, $C_{1-6}$ alkoxy, or $C_{1-6}$ alkylthio, wherein the alkyl, alkoxy, and alkylthio are each independently and optionally substituted with one, two, or three halo. In certain embodiments, $R^1$ is $C_{1-6}$ alkyl, optionally substituted with one, two, or three halo. In certain embodiments. $R^1$ is methyl, ethyl, propyl (e.g., n-propyl and isopropyl), butyl (n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^1$ is methyl. In certain embodiments, $R^1$ is $C_{2-6}$ alkenyl, $C_{2-6}$ alkynyl, phenyl, benzyl, phenoxy, benzoxy, or heterocyclyl. In certain embodiments. $R^1$ is —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2$$R^{1a}$, —OS(O)N$R^{1b}R^{1c}$, —OS(O)$_2$N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2$$R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2$$R^{1a}$, —S(O)N$R^{1b}R^{1c}$, or —S(O)$_2$N$R^{1b}R^{1c}$; wherein $R^{1a}$, $R^{1b}$, $R^{1c}$, and $R^{1d}$ are each as defined herein. In certain embodiments, $R^1$ is —C(O)$R^{1a}$, —C(O)O$R^{1a}$, —C(O)N$R^{1b}R^{1c}$, —OC(O)N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$S(O)$_2$$R^{1d}$, —S(O)$_2$$R^{1a}$, or —S(O)$_2$N$R^{1b}R^{1c}$; wherein $R^{1a}$, $R^{1b}$, $R^{1c}$, and $R^{1d}$ are each as defined herein.

In certain embodiments, $R^2$ is halo, cyano, nitro, hydroxyl, or guanidine. In certain embodiments, $R^2$ is halo. In certain embodiments, $R^2$ is fluoro or chloro. In certain embodiments, $R^2$ is $C_{1-6}$ alkyl, $C_{1-6}$ alkoxy, or $C_{1-6}$ alkylthio, wherein the alkyl, alkoxy, and alkylthio are each independently and optionally substituted with one, two, or three halo. In certain embodiments, $R^2$ is $C_{1-6}$ alkyl, optionally substituted with one, two, or three halo. In certain embodiments, $R^2$ is methyl, ethyl, propyl (e.g., n-propyl and isopropyl), butyl (n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^2$ is methyl. In certain embodiments, $R^2$ is $C_{2-6}$ alkenyl, $C_{2-6}$ alkynyl, phenyl, benzyl, phenoxy, benzoxy, or heterocyclyl. In certain embodiments, $R^2$ is —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2$$R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2$$R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2$$R^{1a}$, —S(O)N$R^{1b}R^{1c}$, or —S(O)$_2$N$R^{1b}R^{1c}$; wherein $R^{1a}$, $R^{1b}$, $R^{1c}$, and $R^{1d}$ are each as defined herein. In certain embodiments, $R^2$ is —C(O)$R^{1a}$, —C(O)O$R^{1a}$, —C(O)N$R^{1b}R^{1c}$, —OC(O)N$R^{1b}R^{1c}$, —N$R^{1b}R^{1c}$, —N$R^{1a}$C(O)$R^{1d}$, —N$R^{1a}$C(O)O$R^{1d}$, —$^{1a}$S(O)$_2$$R^{1d}$, —S(O)$_2$$R^{1a}$, or —S(O)$_2$N$R^{1b}R^{1c}$; wherein $R^{1a}$, $R^{1b}$, $R^{1c}$, and $R^{1d}$ are each as defined herein.

In certain embodiments, $R^1$ and $R^2$ are the same. In certain embodiments, $R^1$ and $R^2$ are fluoro. In certain embodiments, $R^1$ and $R^2$ are chloro. In certain embodiments, $R^1$ and $R^2$ are methyl.

In certain embodiments, $R^1$ and $R^2$ are different. In certain embodiments, $R^1$ is fluoro, chloro, or methyl. In certain embodiments, $R^2$ is fluoro, chloro, or methyl.

In certain embodiments, $R^3$ is hydrogen, halo, cyano, nitro, or hydroxyl. In certain embodiments, $R^3$ is cyano or nitro. In certain embodiments, $R^3$ is $C_{1-6}$ alkyl, $C_{1-6}$ alkoxy, or $C_{1-6}$ alkylthio, wherein the alkyl, alkoxy, and alkylthio are each independently and optionally substituted with one, two, or three halo. In certain embodiments, $R^3$ is $C_{2-6}$ alkenyl, $C_{2-6}$ alkynyl, or tetrazolyl. In certain embodiments, $R^3$ is —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2$$R^{1a}$, —OS(O)N$R^{1b}R^{1c}$, —OS(O)$_2$N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2$$R^{1d}$, —N$R^{1a}$S(O)$R^{1d}$, —N$R^{1a}$S(O)$_2$$R^{1d}$, —S(O)$R^{1a}$, —S(O)$_2$$R^{1a}$, —S(O)N$R^{1b}R^{1c}$, or —S(O)$_2$N$R^{1b}R^{1c}$; wherein $R^{1a}$, $R^{1b}$, $R^{1c}$, and $R^{1d}$ are each as defined herein. In certain embodiments, $R^3$ is —C(O)$R^{1a}$, —C(O)O$R^{1a}$, —C(O)N$R^{1b}R^{1c}$, —OC(O)N$R^{1b}R^{1c}$, —N$R^{1b}R^{1c}$, —N$R^{1a}$C(O)$R^{1d}$, or —N$R^{1a}$C(O)O$R^{1d}$; wherein $R^{1a}$, $R^{1b}$, $R^{1c}$, and $R^{1d}$ are each as defined herein.

In certain embodiments, $R^4$ is

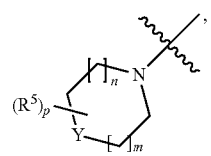

wherein $R^5$, Y, m, n, and p are each as defined herein; and $R^5$ is not attached to Y. In certain embodiments, $R^4$ is

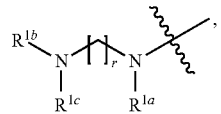

wherein $R^{1a}$, $R^{1b}$, and $R^{1c}$, are each as defined herein.

In certain embodiments, $R^5$ is halo, cyano, nitro, hydroxyl, oxo, or guanidine. In certain embodiments, $R^5$ is oxo. In certain embodiments, $R^5$ is $C_{1-6}$ alkyl, $C_{1-6}$ alkoxy, or $C_{1-6}$ alkylthio, wherein the alkyl, alkoxy, and alkylthio are each independently and optionally substituted with one, two, or three halo. In certain embodiments, $R^5$ is $C_{1-6}$ alkyl. In certain embodiments, $R^5$ is methyl, ethyl, propyl (e.g., n-propyl and isopropyl), butyl (n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^5$ is methyl. In certain embodiments, $R^5$ is $C_{2-6}$ alkenyl, $C_{2-6}$ alkynyl, phenyl, benzyl, phenoxy, benzoxy, or heterocyclyl. In certain embodiments, $R^5$ is —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1d}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)$R^{1d}$, —N$R^{1a}$S(O)$_2R^{1d}$, —S(O)$R^{1a}$, —S(O)$_2R^{1a}$, —S(O)N$R^{1b}R^{1c}$, or —S(O)$_2$N$R^{1b}R^{1c}$; wherein $R^{1a}$, $R^{1b}$, $R^{1c}$, and $R^{1d}$ are each as defined herein. In certain embodiments, $R^5$ is C(O)$R^{1a}$, —C(O)O$R^{1a}$, —C(O)N$R^{1b}R^{1c}$, —OC(O)N$R^{1b}R^{1c}$, —N$R^{1b}R^{1c}$, —N$R^{1a}$C(O)$R^{1d}$, or N$R^{1a}$C(O)O$R^{1d}$; wherein $R^{1a}$, $R^{1b}$, $R^c$, and $R^{1d}$ are each as defined herein. In certain embodiments, $R^5$ is C(O)O$R^{1a}$, wherein $R^{1a}$ is as defined herein. In certain embodiments, $R^5$ is —C(O)O—$C_{1-6}$ alkyl, optionally substituted with one or more substituents. In certain embodiments, $R^5$ is —C(O)O—$C_{1-6}$ alkyl. In certain embodiments, $R^5$ is methoxycarbonyl.

In certain embodiments, X is O. In certain embodiments. X is S.

In certain embodiments, Y is —O—. In certain embodiments, Y is —S—. In certain embodiments, Y is —S(O)—. In certain embodiments, Y is —S(O)$_2$—. In certain embodiments. Y is —N$R^{1a}$—, wherein $R^{1a}$ is as defined herein. In certain embodiments, Y is —C($R^{1a}$)($R^{1d}$)—, wherein $R^{1a}$ and $R^{1d}$ are each as defined herein. In certain embodiments, Y is —C$R^{1a}$N$R^{1b}R^{1c}$—, wherein $R^{1a}$, $R^{1b}$, and $R^{1c}$ are each as defined herein.

In certain embodiments, m is 0. In certain embodiments, m is 1. In certain embodiments, m is 2. In certain embodiments, m is 3.

In certain embodiments, n is 1. In certain embodiments, n is 2. In certain embodiments, n is 3.

In certain embodiments, m is 1 and n is 1. In certain embodiments, m is 1 and n is 2.

In certain embodiments, p is 0. In certain embodiments, p is 1. In certain embodiments, p is 2. In certain embodiments, p is 3. In certain embodiments, p is 4.

In certain embodiments, r is 1. In certain embodiments, r is 2. In certain embodiments, r is 3. In certain embodiments, r is 4. In certain embodiments, r is 5. In certain embodiments, r is 6.

In certain embodiments, $R^{1a}$ is hydrogen. In certain embodiments, $R^{1a}$ is phenyl or benzyl. In certain embodiments, $R^{1a}$ is $C_{3-7}$ cycloalkyl. In certain embodiments, $R^{1a}$ is cyclopentyl or cyclohexyl. In certain embodiments, $R^{1a}$ is heteroaryl or heterocyclyl, each optionally substituted. In certain embodiments, $R^{1a}$ is 3-oxo-1H-imidazo[1,5-c]imidazol-2(3H)-yl. In certain embodiments, $R^{1a}$ is 5-butyl-7-chloro-3-oxo-1H-imidazo[1,5-c]imidazol-2(3H)-yl. In certain embodiments, $R^{1a}$ is $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl. In certain embodiments, $R^{1a}$ is alkyl. In certain embodiments, $R^{1a}$ is methyl, ethyl, propyl (e.g., n-propyl and isopropyl), butyl (n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^{1a}$ is methyl, methyl, isopropyl, or 3-pentyl.

In certain embodiments, $R^{1b}$ is hydrogen. In certain embodiments, $R^{1b}$ is phenyl. In certain embodiments, $R^{1b}$ is benzyl. In certain embodiments, $R^{1b}$ is $C_{3-7}$ cycloalkyl. In certain embodiments, $R^{1b}$ is cyclopentyl. In certain embodiments, $R^{1b}$ is $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl. $C_{3-7}$ cycloalkylcarbamoyl, and $C_{3-7}$ heterocyclylcarbamoyl. In certain embodiments, $R^{1b}$ is $C_{1-6}$ alkyl. In certain embodiments, $R^{1b}$ is methyl, ethyl, propyl (e.g., n-propyl and isopropyl), butyl (n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^{1b}$ is methyl or ethyl.

In certain embodiments, $R^{1c}$ is hydrogen. In certain embodiments, $R^{1c}$ is phenyl. In certain embodiments, $R^{1c}$ is benzyl. In certain embodiments, $R^{1c}$ is $C_{3-7}$ cycloalkyl. In certain embodiments, $R^{1c}$ is cyclopentyl. In certain embodiments, $R^{1c}$ is $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl. In certain embodiments, $R^{1c}$ is $C_{1-6}$ alkyl. In certain embodiments, $R^{1c}$ is methyl, ethyl, propyl n-propyl and isopropyl), butyl (n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^{1c}$ is methyl or ethyl.

In certain embodiments, $R^{1b}$ and $R^{1c}$ together with the N atom to which they are attached form heteroaryl, optionally substituted with one or more substituents Q as described herein. In certain embodiments, $R^{1b}$ and $R^{1c}$ together with the N atom to which they are attached form heterocyclyl, optionally substituted with one or more substituents Q as described herein. In certain embodiments, $R^{1b}$ and $R^{1c}$ together with the N atom to which they are attached form 5- to 7-membered heteroaryl. In certain embodiments, $R^{1b}$ and $R^{1c}$ together with the N atom to which they are attached form 5- to 7-membered heterocyclyl. In certain embodiments, $R^{1b}$ and $R^{1c}$ together with the N atom to which they are attached form 5-membered heterocyclyl. In certain embodiments, $R^{1b}$ and $R^{1c}$ together with the N atom to which they are attached form pyrrolidinyl. In certain embodiments, $R^{1b}$ and $R^{1c}$ together with the N atom to which they are attached form 6-membered heterocyclyl. In certain embodiments, $R^{1b}$ and $R^{1c}$ together with the N atom to which they are attached form piperidinyl.

In certain embodiments, $R^{1d}$ is hydrogen. In certain embodiments, $R^{1d}$ is phenyl or benzyl. In certain embodiments, $R^{1d}$ is $C_{3-7}$ cycloalkyl. In certain embodiments, $R^{1d}$ is cyclopentyl. In certain embodiments, $R^{1d}$ is $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl. In certain embodiments, $R^{1d}$ is $C_{1-6}$ alkyl. In certain embodiments, $R^{1d}$ is methyl, ethyl, propyl (e.g., n-propyl and isopropyl), butyl (n-butyl, 2-butyl, isobutyl, or t-butyl), or pentyl (e.g., n-pentyl, 2-pentyl, 3-pentyl, 2-methylbutyl, 3-methylbutyl, 1,1-dimethylpropyl, 1,2-dimethylpropyl, or 2,2-dimethylpropyl). In certain embodiments, $R^{1d}$ is methyl, isopropyl, or 3-pentyl. In certain embodiments, $R^{1d}$ is 1-hydroxyl-isopropyl.

In one embodiment, provided herein is a compound selected from the group consisting of:

51

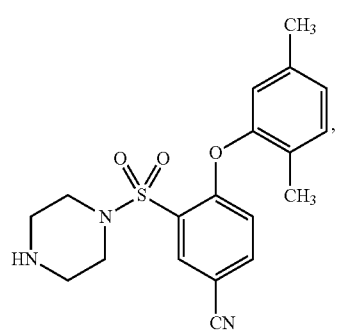

52

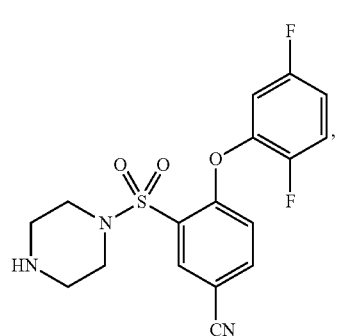

53

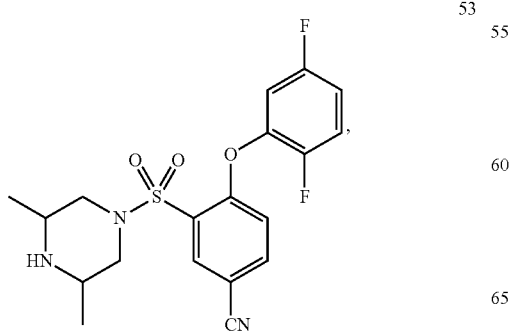

54

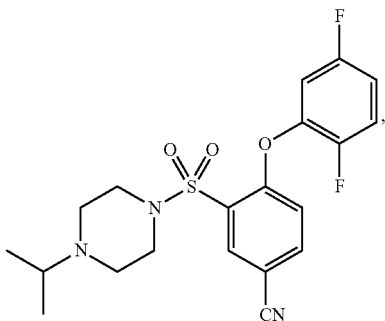

55

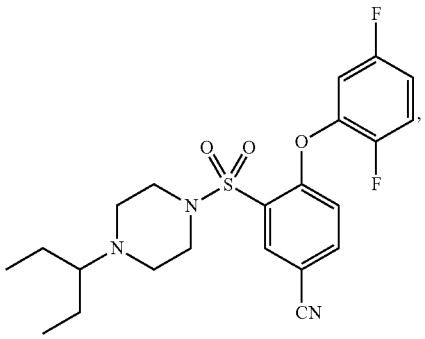

56

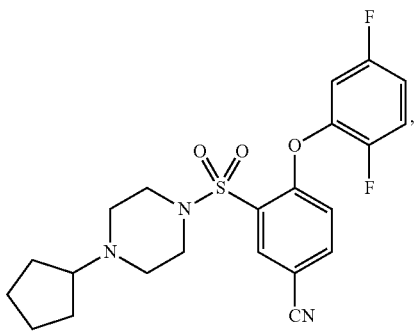

57

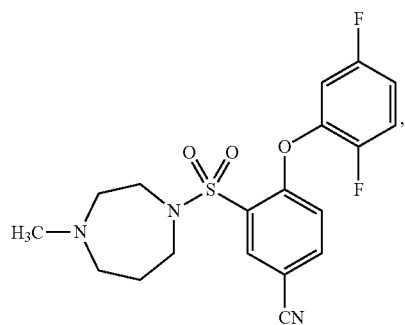

58

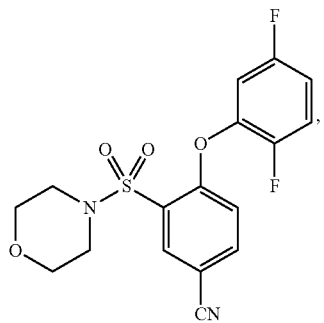

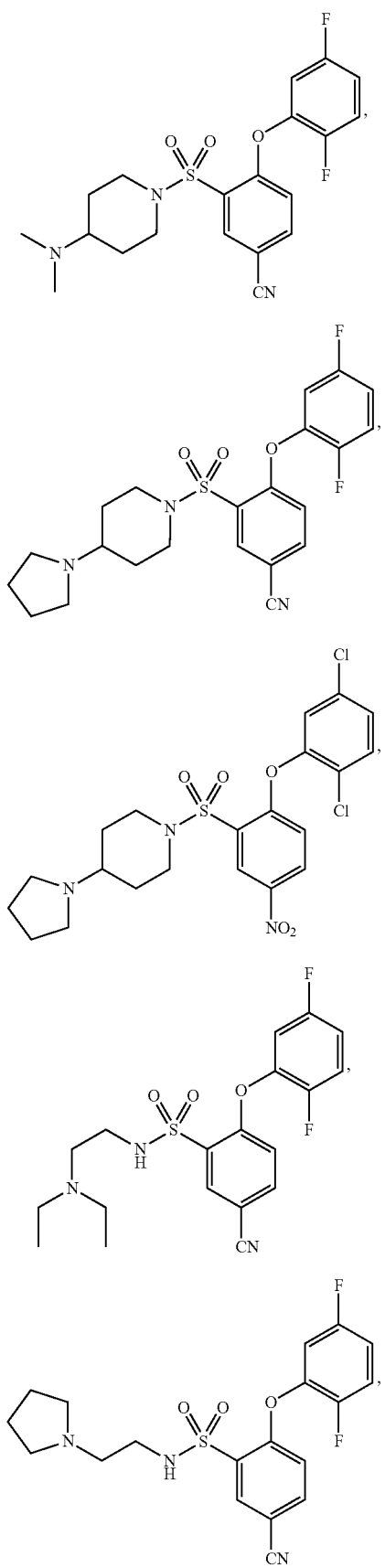
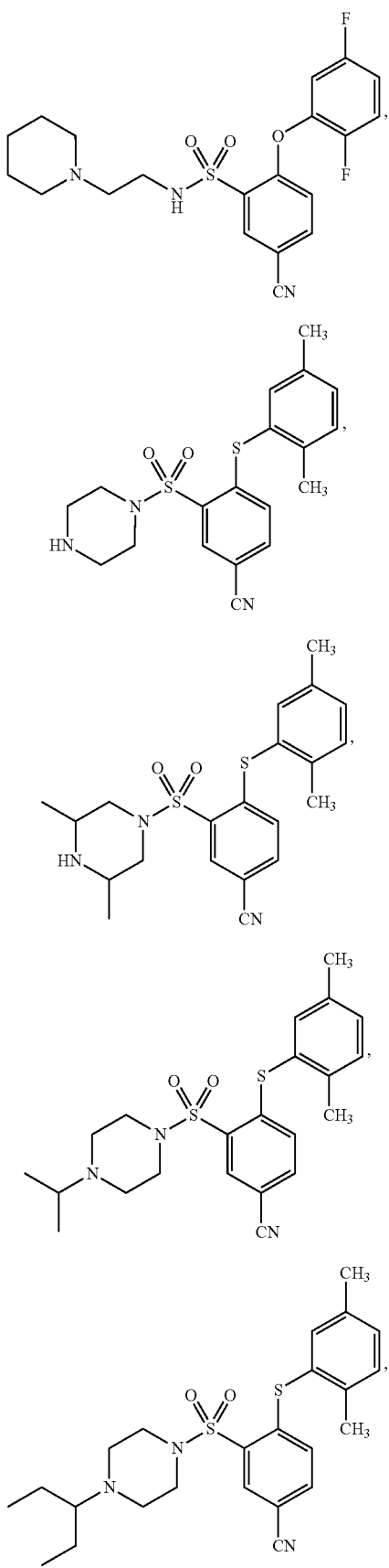

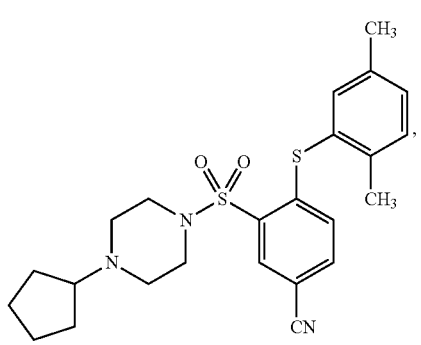
69
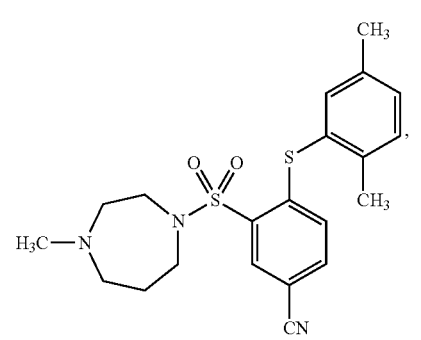
70
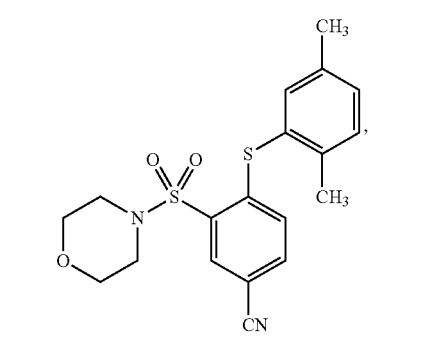
71
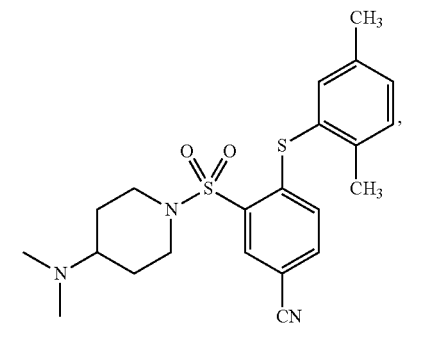
72
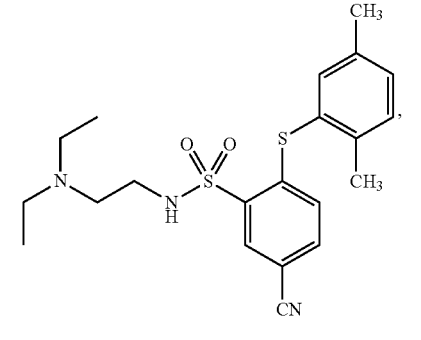
73
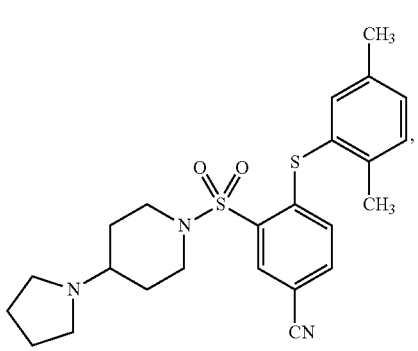
74
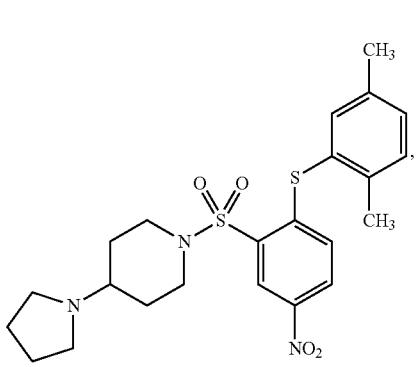
75
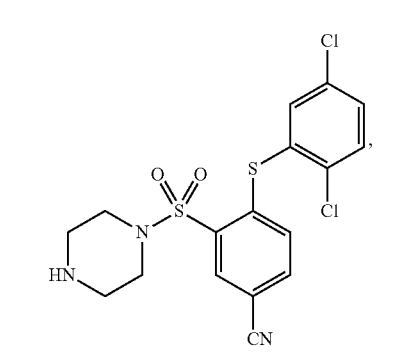
76
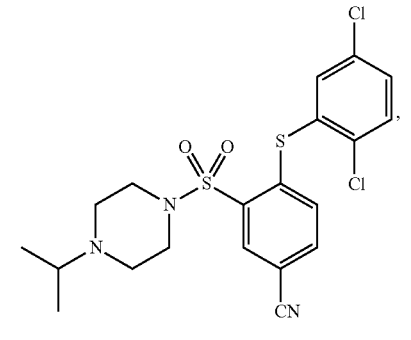
77

-continued
78 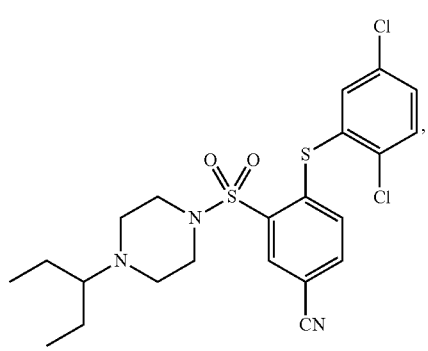
79 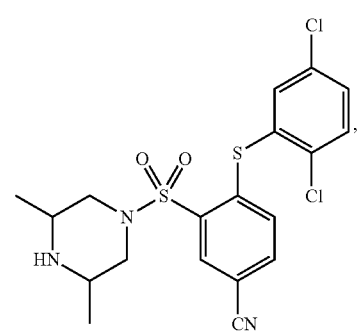
80 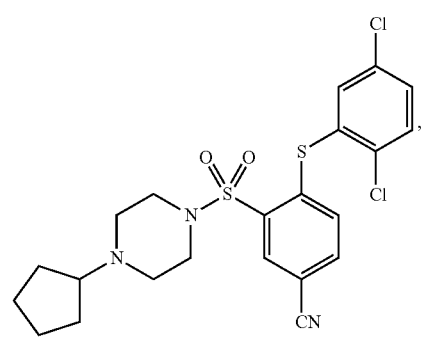
81 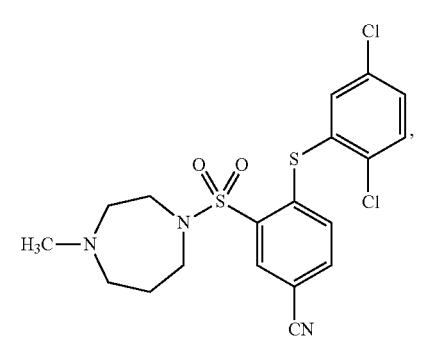
82 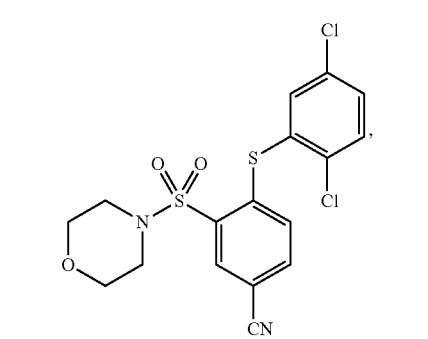
-continued
83 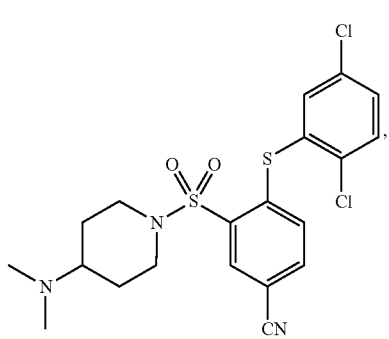
84 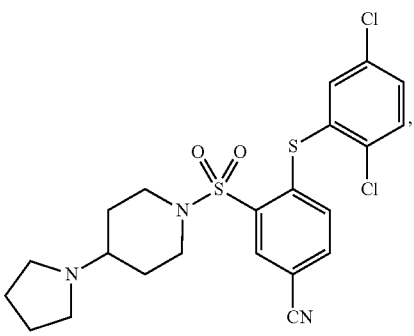
85 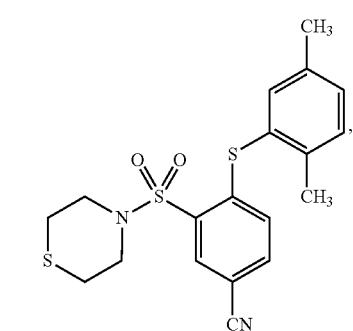
86 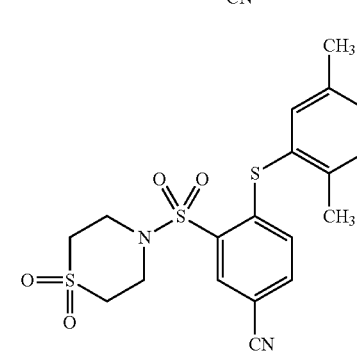
87 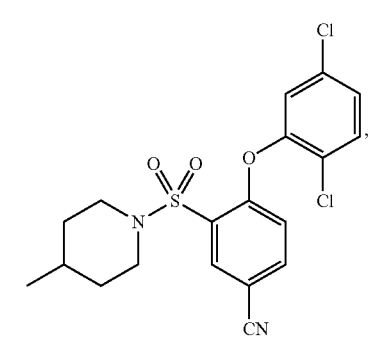

88
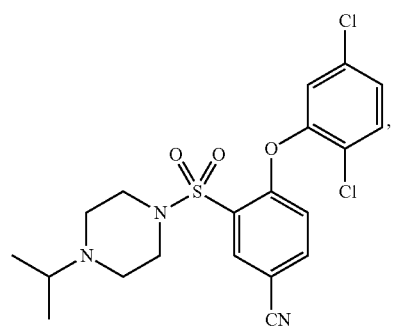
92
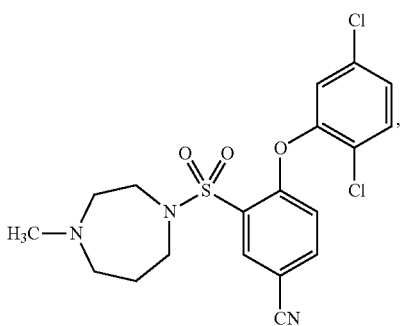
89
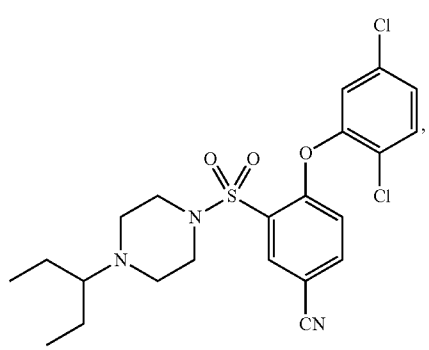
93
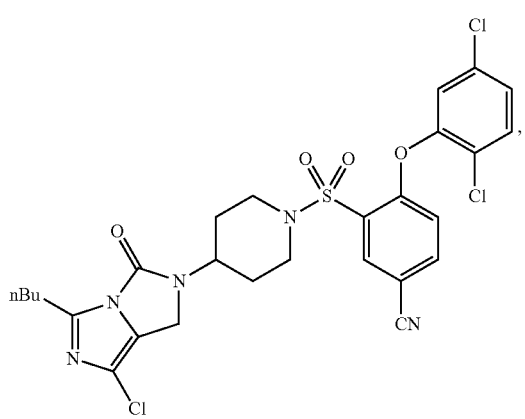
90
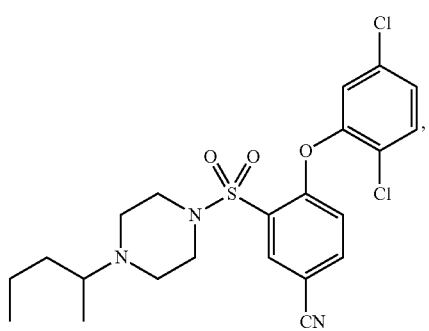
94
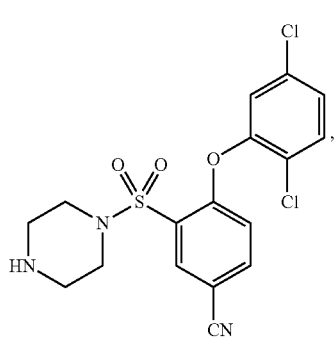
91
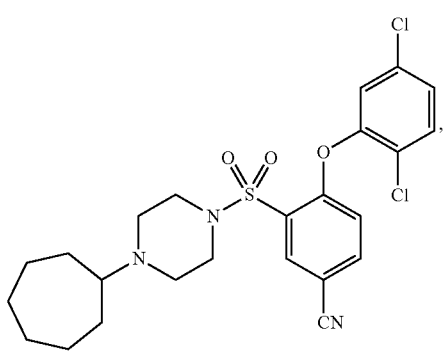
95
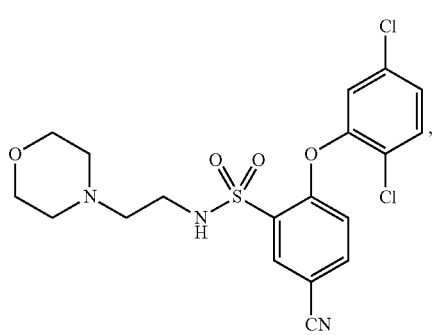

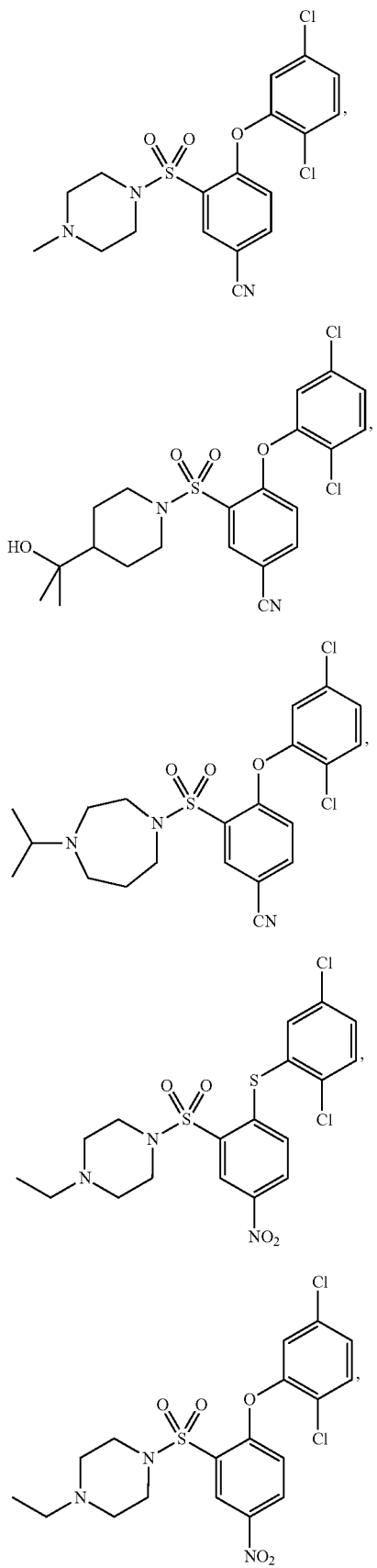
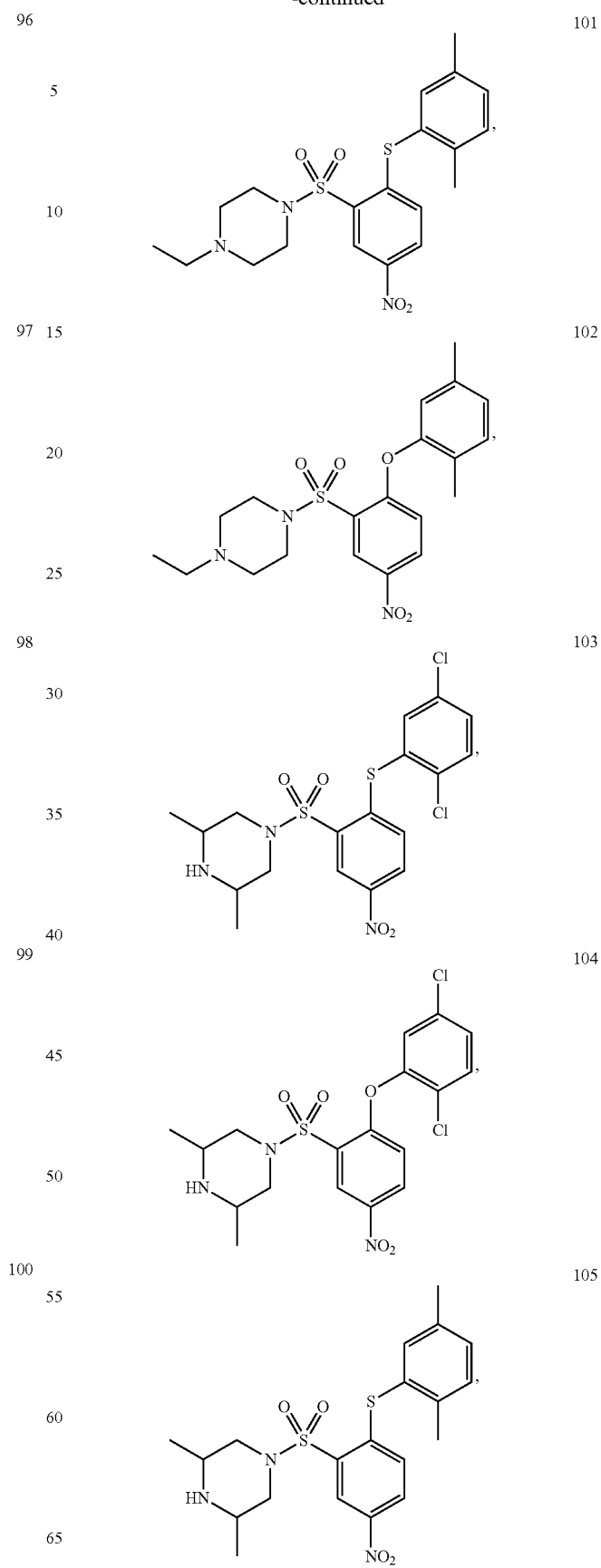

106
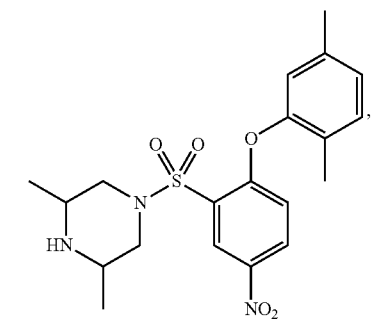
107
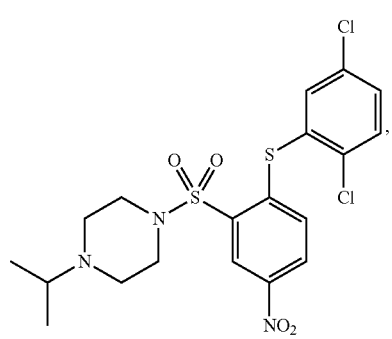
108
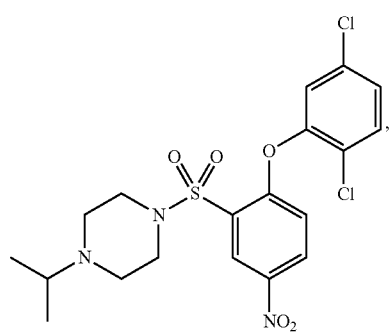
109
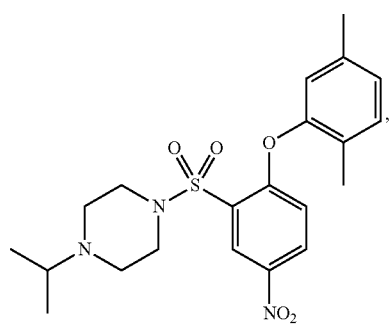
110
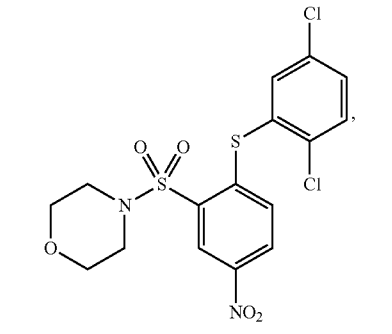
111
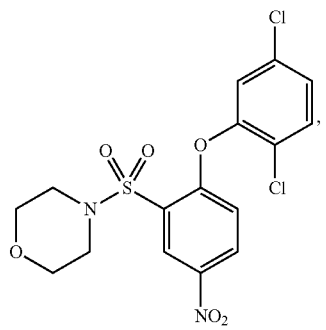
112
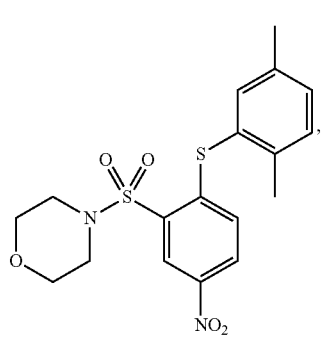
113
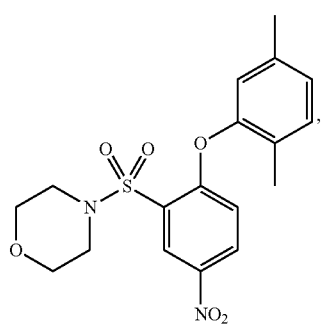
114
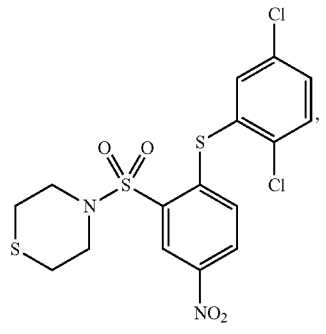
115
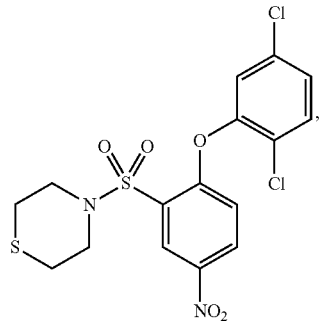

116 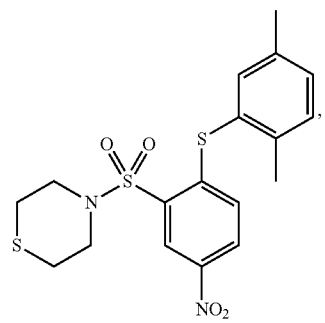
117 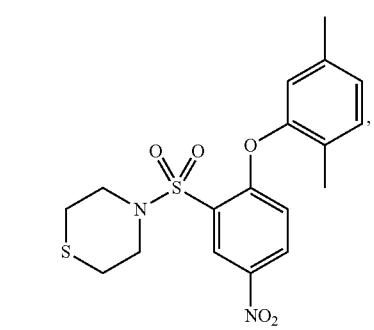
118 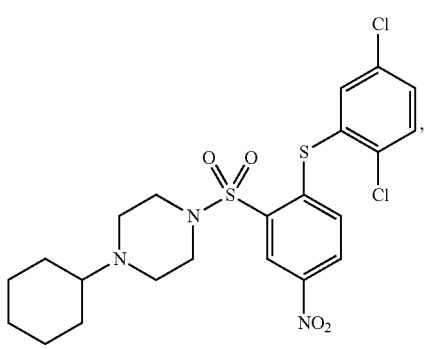
119 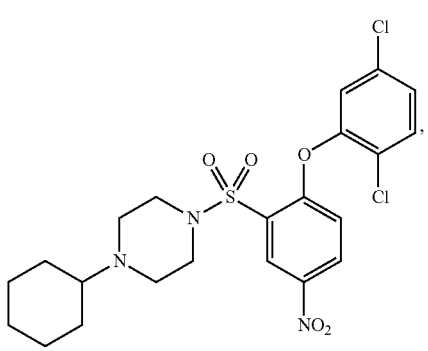
120 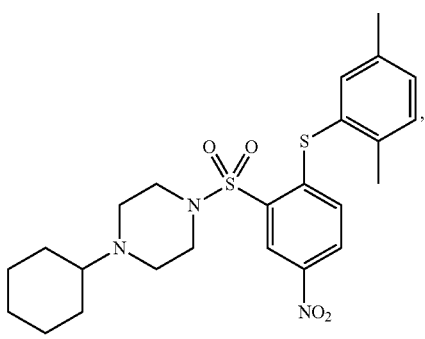
121 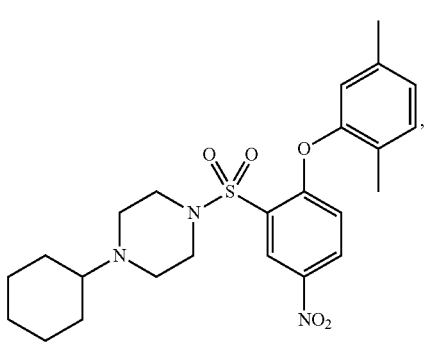
122 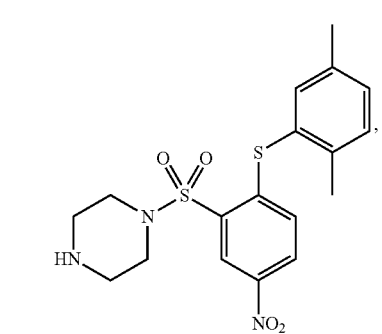
123 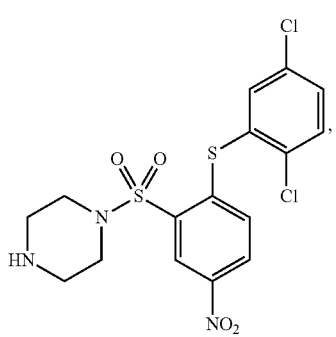

124
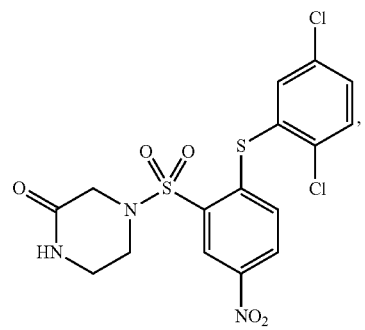
125
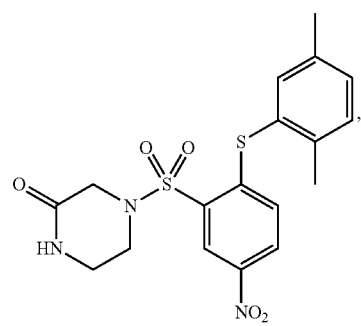
126
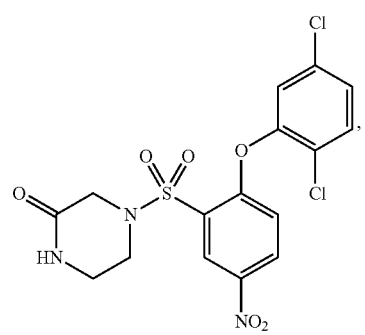
127
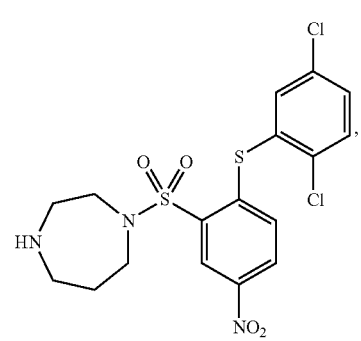
128
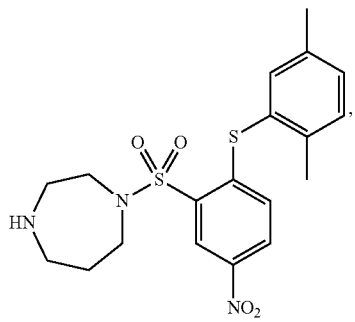
129
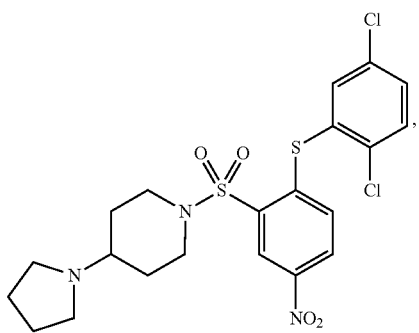
130
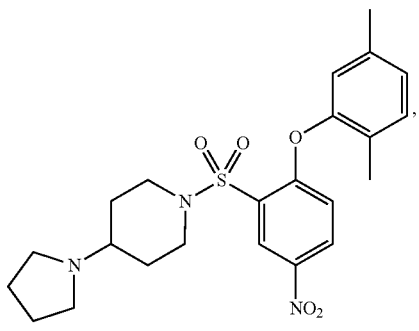
131
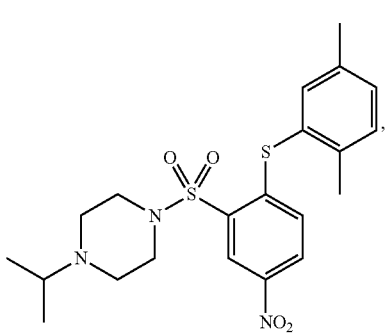
132
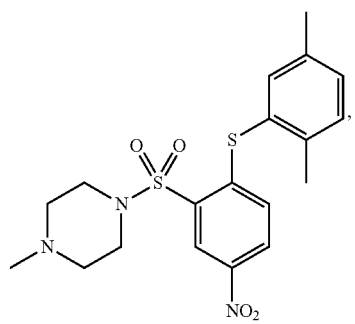

133 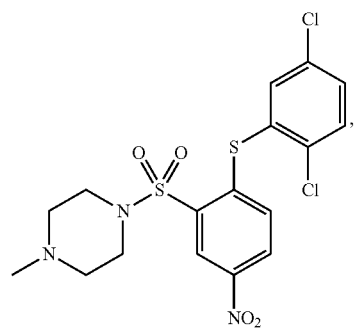
134 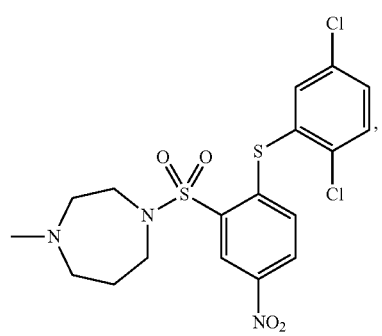
135 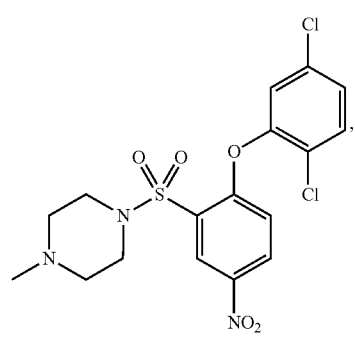
136 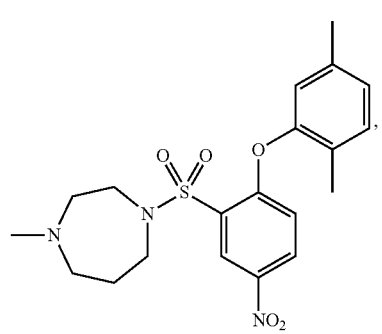
137 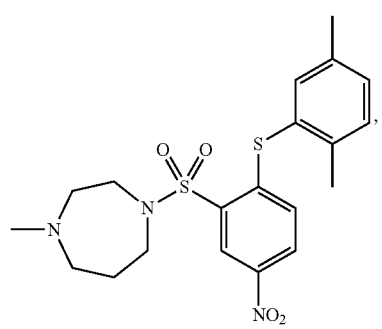
138 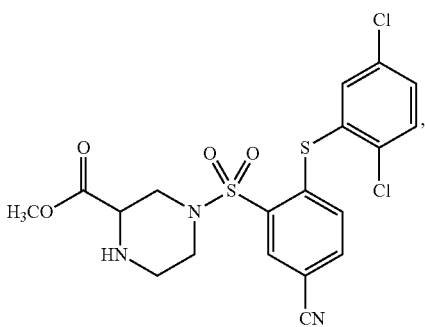
139 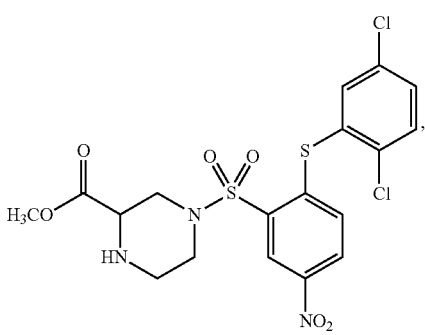
140 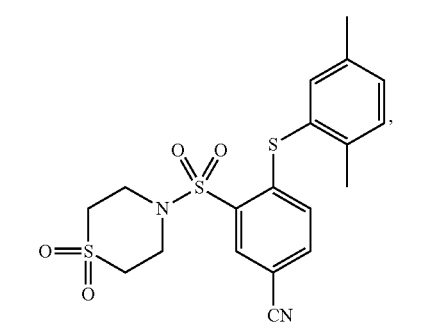
141 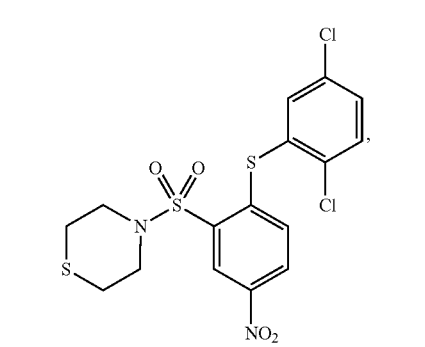
142 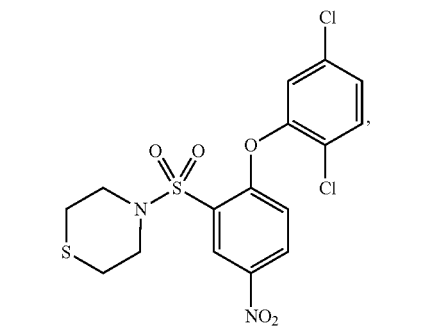

-continued

143
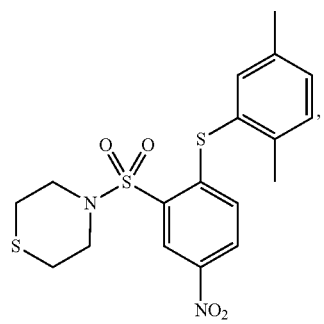

144
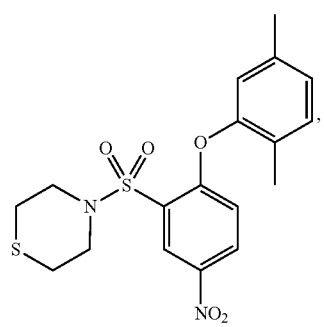

145
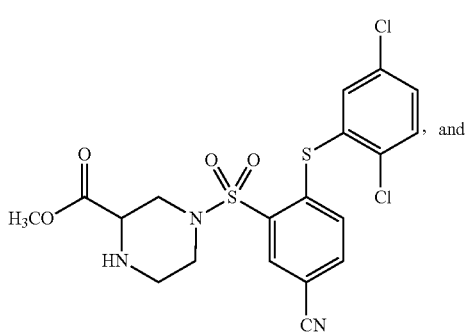
, and

146
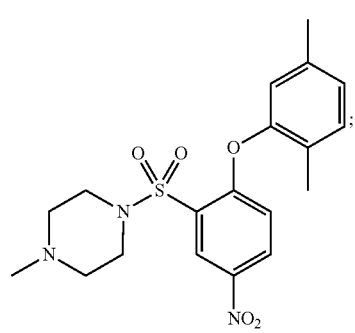

and enantiomers, mixtures of enantiomers, mixtures of two or more diastereomers, tautomers, and mixtures of two or more tautomers thereof; and pharmaceutically acceptable salts, solvates, hydrates, and prodrugs thereof.

The compounds provided herein are intended to encompass all possible stereoisomers, unless a particular stereochemistry is specified. Where the compound provided herein contains an alkenyl or alkenylene group, the compound may exist as one or mixture of geometric cis/trans (or Z/E) isomers. Where structural isomers are interconvertible, the compound may exist as a single tautomer or a mixture of tautomers. This can take the form of proton tautomerism in the compound that contains, for example, an imino, keto, or oxime group; or so-called valence tautomerism in the compound that contain an aromatic moiety. It follows that a single compound may exhibit more than one type of isomerism.

The compounds provided herein may be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of skill in the art will recognize that administration of a compound in its (R) form is equivalent, for compounds that undergo epimerization in vivo, to administration of the compound in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the compound provided herein contains an acidic or basic moiety, it may also be provided as a pharmaceutically acceptable salt (See, Berge et al., *J. Pharm. Sci.* 1977, 66, 1-19; and "Handbook of Pharmaceutical Salts, Properties, and Use," Stahl and Wermuth, Ed.; Wiley-VCH and VHCA, Zurich, 2002).

Suitable acids for use in the preparation of pharmaceutically acceptable salts include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

In one embodiment, the compound provided here is a hydrochloride salt.

Suitable bases for use in the preparation of pharmaceutically acceptable salts, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, deanol, diethanolamine, diethylamine, dimethylamine, dipropylamine, diisopropylamine, 2-(diethylamino)-ethanol, ethanolamine, ethylamine, ethylenediamine, isopropylamine, N-methylglucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, secondary amines, triethanolamine, trimethylamine, triethylamine, N-methyl-D-glucamine, 2-amino-2-(hydroxymethyl)-1,3-propanediol, and tromethamine.

The compound provided herein may also be provided as a prodrug, which is a functional derivative of the compound, for example, of Formula I and is readily convertible into the parent compound in vivo. Prodrugs are often useful because, in some situations, they may be easier to administer than the parent compound. They may, for instance, be bioavailable by oral administration whereas the parent compound is not. The prodrug may also have enhanced solubility in pharmaceutical compositions over the parent compound. A prodrug may be converted into the parent drug by various mechanisms, including enzymatic processes and metabolic hydrolysis. See Harper, *Progress in Drug Research* 1962, 4, 221-294; Morozowich et al. in "Design of Biopharmaceutical Properties through Prodrugs and Analogs," Roche Ed., APHA Acad. Pharm. Sci. 1977; "Bioreversible Carriers in Drug in Drug Design, Theory and Application," Roche Ed., APHA Acad. Pharm. Sci. 1987; "Design of Prodrugs," Bundgaard, Elsevier, 1985; Wang et al., *Curr. Pharm. Design* 1999, 5, 265-287; Pauletti et al., *Adv. Drug. Delivery Rev.* 1997, 27, 235-256; Mizen et al., *Pharm. Biotech.* 1998, 11, 345-365; Gaignault et al., *Pract. Med. Chem.* 1996, 671-696; Asgharnejad in "Transport Processes in Pharmaceutical Systems," Amidon et al., Ed., Marcell Dekker, 185-218, 2000; Balant et al., *Eur. J. Drug Metab. Pharmacokinet.* 1990, 15, 143-53; Balimane and Sinko, *Adv. Drug Delivery Rev.* 1999, 39, 183-209; Browne, *Clin. Neuropharmacol.* 1997, 20, 1-12; Bundgaard, *Arch. Pharm. Chem.* 1979, 86, 1-39; Bundgaard, *Controlled Drug Delivery* 1987, 17, 179-96; Bundgaard, *Adv. Drug Delivery Rev.* 1992, 8, 1-38; Fleisher et al., *Adv. Drug Delivery Rev.* 1996, 19, 115-130; Fleisher et al., *Methods Enzymol.* 1985, 112, 360-381; Farquhar et al., *J. Pharm. Sci.* 1983, 72, 324-325; Freeman et al., *J. Chem. Soc., Chem. Commun.* 1991, 875-877; Friis and Bundgaard, *Eur. J. Pharm. Sci.* 1996, 4, 49-59; Gangwar et al., *Des. Biopharm. Prop. Prodrugs Analogs,* 1977, 409-421; Nathwani and Wood, *Drugs* 1993, 45, 866-94; Sinhababu and Thakker, *Adv. Drug Delivery Rev.* 1996, 19, 241-273; Stella et al., *Drugs* 1985, 29, 455-73; Tan et al. *Adv. Drug Delivery Rev.* 1999, 39, 117-151; Taylor, *Adv. Drug Delivery Rev.* 1996, 19, 131-148; Valentino and Borchardt, *Drug Discovery Today* 1997, 2, 148-155; Wiebe and Knaus, *Adv. Drug Delivery Rev.* 1999, 39, 63-80; and Waller et al., *Br. J. Clin. Pharmac.* 1989, 28, 497-507.

Methods of Synthesis

The compound provided herein can be prepared, isolated, or obtained by any method known to one of skill in the art. For an example, a compound of Formula I can be prepared as shown in Scheme 1. Nitrobenzene 1 reacts with compound 2 via aromatic substitution reaction in the presence of a base, such as potassium carbonate, to form nitrobiaryl 3. Subsequently, the nitrobiaryl 3 is reduced with a reducing agent, such as $TiCl_2$ or sodium hydrosulfite, to aminobiaryl 4, which is then converted to sulfonyl chloride 5 via the Sandmeyer reaction. A compound of Formula I is formed by reacting sulfonyl chloride 5 with $R^4H$ in the presence of a base, such as triethylamine.

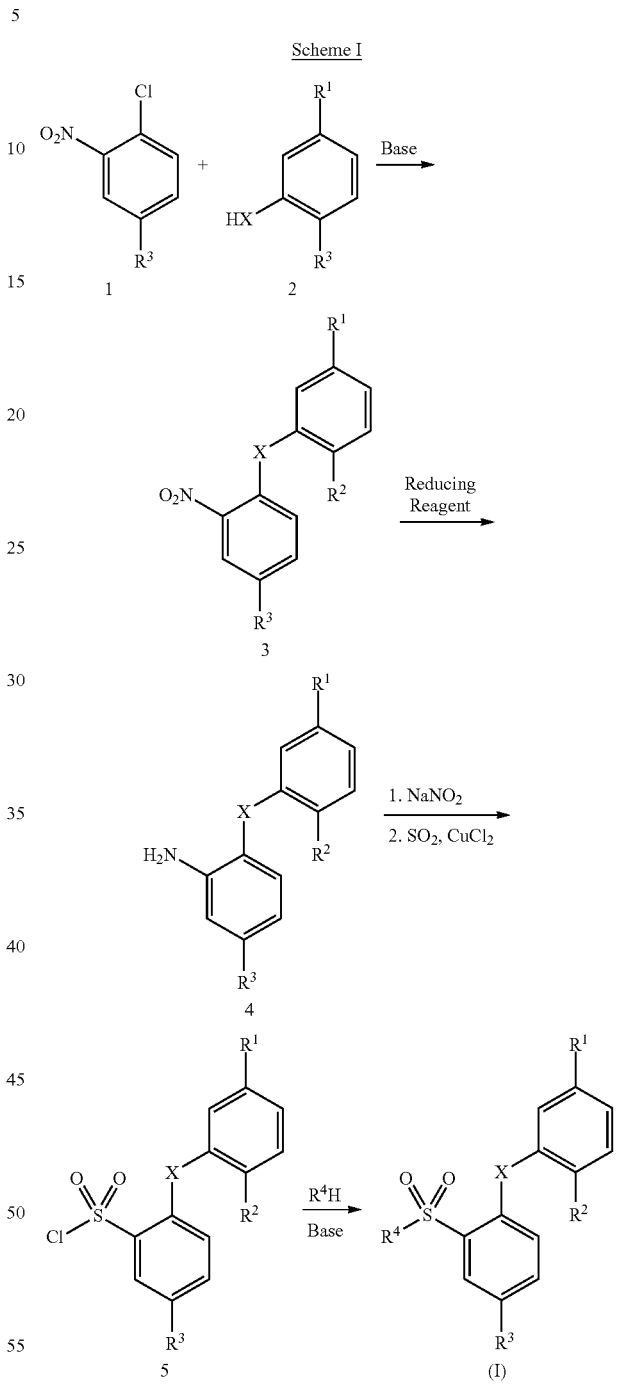

A compound of Formula I can also be prepared as shown in Scheme 2. Aniline 6 is first converted into sulfonyl chloride 7 via the Sandmeyer reaction. Subsequently, sulfonyl chloride 7 reacts with $R^4H$ in the presence of a base, such as triethylamine, to form chlorobenzene 8, which then reacts with compound 2 via aromatic substitution reaction in the presence of a base, such as potassium carbonate, to form a compound of Formula I.

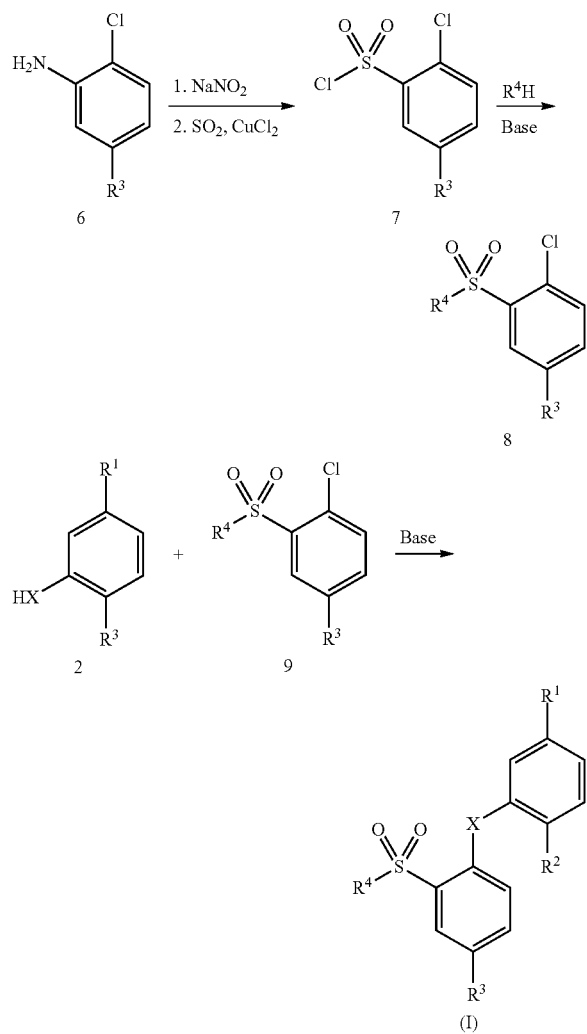

Scheme 2

Pharmaceutical Compositions

Provided herein are pharmaceutical compositions comprising a compound provided herein, e.g., a compound of Formula I, as an active ingredient, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; in combination with a pharmaceutically acceptable vehicle, carrier, diluent, or excipient, or a mixture thereof.

The compound provided herein may be administered alone, or in combination with one or more other compounds provided herein. The pharmaceutical compositions that comprise a compound provided herein, e.g., a compound of Formula I, can be formulated in various dosage forms for oral, parenteral, and topical administration. The pharmaceutical compositions can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art (see, *Remington: The Science and Practice of Pharmacy,* supra; *Modified-Release Drug Delivery Technology,* 2nd Edition, Rathbone et al., Eds., Marcel Dekker, Inc.: New York, N.Y., 2008).

In one embodiment, the pharmaceutical compositions are provided in a dosage form for oral administration, which comprise a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and one or more pharmaceutically acceptable excipients or carriers.

In another embodiment, the pharmaceutical compositions are provided in a dosage form for parenteral administration, which comprise a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and one or more pharmaceutically acceptable excipients or carriers.

In yet another embodiment, the pharmaceutical compositions are provided in a dosage form for topical administration, which comprise a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof; and one or more pharmaceutically acceptable excipients or carriers.

The pharmaceutical compositions provided herein can be provided in a unit-dosage form or multiple-dosage form. A unit-dosage form, as used herein, refers to physically discrete a unit suitable for administration to a human and animal subject, and packaged individually as is known in the art. Each unit-dose contains a predetermined quantity of an active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein can be administered at once, or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein for oral administration can be provided in solid, semisolid, or liquid dosage forms for oral administration. As used herein, oral administration also includes buccal, lingual, and sublingual administration. Suitable oral dosage forms include, but are not limited to, tablets, fastmelts, chewable tablets, capsules, pills, strips, troches, lozenges, pastilles, cachets, pellets, medicated chewing gum, bulk powders, effervescent or non-effervescent powders or granules, oral mists, solutions, emulsions, suspensions, wafers, sprinkles, elixirs, and syrups. In addition to the active ingredient(s), the pharmaceutical compositions can contain one or more pharmaceutically acceptable carriers or excipients, including, but not limited to, binders, fillers, diluents, disintegrants, wetting agents, lubricants, glidants, coloring agents, dye-migration inhibitors, sweetening agents, flavoring agents, emulsifying agents, suspending and dispersing agents, preservatives, solvents, non-aqueous liquids, organic acids, and sources of carbon dioxide.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. Suitable fillers include, but are not limited to, talc, calcium carbonate, microcrystalline cellulose, powdered cellulose, dextrates, kaolin, mannitol, silicic acid, sorbitol, starch, pre-gelatinized starch, and mixtures thereof. The amount of a binder or filler in the pharmaceutical compositions provided herein varies upon the type of formulation, and is readily discernible to those of ordinary skill in the art. The binder or filler may be present from about 50 to about 99% by weight in the pharmaceutical compositions provided herein.

Suitable diluents include, but are not limited to, dicalcium phosphate, calcium sulfate, lactose, sorbitol, sucrose, inositol, cellulose, kaolin, mannitol, sodium chloride, dry starch, and powdered sugar. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The amount of a diluent in the pharmaceutical compositions provided herein varies upon the type of formulation, and is readily discernible to those of ordinary skill in the art.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant.

Suitable glidants include, but are not limited to, colloidal silicon dioxide, CAB-O-SIL® (Cabot Co. of Boston, Mass.), and asbestos-free talc. Suitable coloring agents include, but are not limited to, any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Suitable flavoring agents include, but are not limited to, natural flavors extracted from plants, such as fruits, and synthetic blends of compounds which produce a pleasant taste sensation, such as peppermint and methyl salicylate. Suitable sweetening agents include, but are not limited to, sucrose, lactose, mannitol, syrups, glycerin, and artificial sweeteners, such as saccharin and aspartame. Suitable emulsifying agents include, but are not limited to, gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suitable suspending and dispersing agents include, but are not limited to, sodium carboxymethylcellulose, pectin, tragacanth, Veegum, acacia, sodium carbomethylcellulose, hydroxypropyl methylcellulose, and polyvinylpyrrolidone. Suitable preservatives include, but are not limited to, glycerin, methyl and propylparaben, benzoic add, sodium benzoate and alcohol. Suitable wetting agents include, but are not limited to, propylene glycol monostearate, sorbitan monooleate, diethylene glycol monolaurate, and polyoxyethylene lauryl ether. Suitable solvents include, but are not limited to, glycerin, sorbitol, ethyl alcohol, and syrup. Suitable non-aqueous liquids utilized in emulsions include, but are not limited to, mineral oil and cottonseed oil. Suitable organic acids include, but are not limited to, citric and tartaric acid. Suitable sources of carbon dioxide include, but are not limited to, sodium bicarbonate and sodium carbonate.

It should be understood that many carriers and excipients may serve several functions, even within the same formulation.

The pharmaceutical compositions provided herein for oral administration can be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms can be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein for oral administration can be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein for oral administration can be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations can further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration can be also provided in the forms of liposomes, micelles, microspheres, or nanosystems. Micellar dosage forms can be prepared as described in U.S. Pat. No. 6,350,458.

The pharmaceutical compositions provided herein for oral administration can be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms.

The pharmaceutical compositions provided herein for oral administration can be formulated as immediate or modified release dosage forms, including delayed-, sustained, pulsed-, controlled, targeted-, and programmed-release forms.

B. Parenteral Administration

The pharmaceutical compositions provided herein can be administered parenterally by injection, infusion, or implantation, for local or systemic administration. Parenteral administration, as used herein, include intravenous, intraarterial, intraperitoneal, intrathecal, intraventricular, intraurethral, intrasternal, intracranial, intramuscular, intrasynovial, intravesical, and subcutaneous administration.

The pharmaceutical compositions provided herein for parenteral administration can be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration can include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Suitable non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Suitable water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents are those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

When the pharmaceutical compositions provided herein are formulated for multiple dosage administration, the multiple dosage parenteral formulations must contain an antimicrobial agent at bacteriostatic or fungistatic concentrations. All parenteral formulations must be sterile, as known and practiced in the art.

In one embodiment, the pharmaceutical compositions for parenteral administration are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein for parenteral administration can be formulated as immediate or modified release dosage forms, including delayed-, sustained, pulsed-, controlled-, targeted-, and programmed-release forms.

The pharmaceutical compositions provided herein for parenteral administration can be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include, but are not limited to, polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include but are not limited to, polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein can be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein can be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, and dermal patches. The topical formulation of the pharmaceutical compositions provided herein can also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions can also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein can be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Suitable cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include, but are not limited to, crosslinked acrylic acid polymers, such as carbomers, carboxypolyalkylenes, and CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein can be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, and hydrogels, such as polyvinyl alcohol, hydroxyethyl methacrylate, and polyacrylic acid. Combinations of the various vehicles can also be used. Rectal and vaginal suppositories may be prepared by compressing or molding. The typical weight of a rectal and vaginal suppository is about 2 to about 3 g.

The pharmaceutical compositions provided herein can be administered ophthalmically in the forms of solutions, suspensions, ointments, emulsions, gel-forming solutions, powders for solutions, gels, ocular inserts, and implants.

The pharmaceutical compositions provided herein can be administered intranasally or by inhalation to the respiratory tract. The pharmaceutical compositions can be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions can also be provided as a dry powder for insufflation, alone or in combination with an inert carrier such as lactose or phospholipids; and nasal drops. For intranasal use, the powder can comprise a bioadhesive agent, including chitosan or cyclodextrin.

Solutions or suspensions for use in a pressurized container, pump, spray, atomizer, or nebulizer can be formulated to contain ethanol, aqueous ethanol, or a suitable alternative agent for dispersing, solubilizing, or extending release of the active ingredient provided herein; a propellant as solvent; and/or a surfactant, such as sorbitan trioleate, oleic acid, or an oligolactic acid.

The pharmaceutical compositions provided herein can be micronized to a size suitable for delivery by inhalation, such as about 50 micrometers or less, or about 10 micrometers or less. Particles of such sizes can be prepared using a comminuting method known to those skilled in the art, such as spiral jet milling, fluid bed jet milling, supercritical fluid processing to form nanoparticles, high pressure homogenization, or spray drying.

Capsules, blisters, and cartridges for use in an inhaler or insufflator can be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include, but are not limited to, dextran, glucose, maltose, sorbitol, xylitol, fructose, sucrose, and trehalose. The pharmaceutical compositions provided herein for inhaled/intranasal administration can further comprise a suitable flavor, such as menthol and levomenthol; and/or sweeteners, such as saccharin and saccharin sodium.

The pharmaceutical compositions provided herein for topical administration can be formulated to be immediate release or modified release, including delayed-, sustained-, pulsed-, controlled-, targeted, and programmed release.

D. Modified Release

The pharmaceutical compositions provided herein can be formulated as a modified release dosage form. As used herein, the term "modified release" refers to a dosage form in which the rate or place of release of the active ingredient(s) is different from that of an immediate dosage form when administered by the same route. Modified release dosage forms include, but are not limited to, delayed-, extended-, prolonged-, sustained-, pulsatile-, controlled-, accelerated-, fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form can be fabricated using a matrix controlled release device known to those skilled in the art (see, Takada et al. in "Encyclopedia of Controlled Drug Delivery," Vol. 2, Mathiowitz Ed., Wiley, 1999).

In certain embodiments, the pharmaceutical compositions provided herein in a modified release dosage form is formulated using an erodible matrix device, which is water-swellable, erodible, or soluble polymers, including, but not limited to, synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethyl hydroxyethyl cellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methyl methacrylate, ethyl methacrylate, ethylacrylate, (2-dimethylaminoethyl)methacrylate, and (trimethylaminoethyl)methacrylate chloride.

In certain embodiments, the pharmaceutical compositions provided herein are formulated with a non-erodible matrix device. The active ingredient(s) is dissolved or dispersed in an inert matrix and is released primarily by diffusion through the inert matrix once administered. Materials suitable for use as a non-erodible matrix device include, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubbers, epichlorohydrin rubbers, ethylene/vinyl alcohol copolymer, ethylene/vinyl acetate/vinyl alcohol terpolymer, ethylene/vinyloxyethanol copolymer, polyvinyl chloride, plasticized nylon, plasticized polyethylene terephthalate, natural rubber, silicone rubbers, polydimethylsiloxanes, and silicone carbonate copolymers; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form can be prepared by methods known to those skilled in the art, including direct compression, dry or wet granulation followed by compression, and melt-granulation followed by compression.

2. Osmotic Controlled Release Devices

The pharmaceutical compositions provided herein in a modified release dosage form can be fabricated using an osmotic controlled release device, including, but not limited to, one-chamber system, two-chamber system, asymmetric membrane technology (AMT), and extruding core system (ECS). In general, such devices have at least two components: (a) a core which contains an active ingredient; and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents is water-swellable hydrophilic polymers, which are also referred to as "osmopolymers" and "hydrogels." Suitable water-swellable hydrophilic polymers as osmotic agents include, but are not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol; organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates can be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core can also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate. CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS. HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane can also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane can be formed post-coating by mechanical or laser drilling. Delivery port(s) can also be formed in situ by erosion of a plug of water-soluble material or by rupture of a thinner portion of the membrane over an indentation in the core. In addition, delivery ports can be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form can further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form can be fabricated as a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates can be made by the processes known to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein can be blended with the pharmaceutical compositions to aid in processing and forming the multiparticulates. The resulting particles can themselves constitute the multiparticulate device or can be coated by various film-forming materials, such as enteric polymers, water-swellable, and water-soluble polymers. The multiparticulates can be further processed as a capsule or a tablet.

4. Targeted Delivery

The pharmaceutical compositions provided herein can also be formulated to be targeted to a particular tissue, receptor, or other area of the body of the subject to be treated, including liposome-, resealed erythrocyte-, and antibody-based delivery systems. Examples include, but are not limited to, those disclosed in U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709.874.

Methods of Use

In one embodiment, provided is a method of treating, preventing, or ameliorating one or more symptoms of a disorder, disease, or condition associated with CCR3 in a subject, which comprises administering to the subject a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In another embodiments, provided is a method of treating, preventing, or ameliorating one or more symptoms of a disorder, disease, or condition responsive to the modulation of CCR3 activity in a subject, comprising administering to the subject a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method of treating, preventing, or ameliorating one or more symptoms of a disorder, disease, or condition mediated by a CCR3 receptor in a subject, comprising administering to the subject a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method for treating, preventing, or ameliorating one or more symptoms of an eosinophil-related disorder, disease, or condition in a subject, comprising administering to the subject a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method for treating, preventing, or ameliorating one or more symptoms of a basophil-related disorder, disease, or condition in a subject, comprising administering to a subject, a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method for treating, preventing, or ameliorating one or more symptoms of a mast cell-related disorder, disease, or condition in a subject, comprising administering to a subject a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

In yet another embodiment, provided is a method for treating, preventing, or ameliorating one or more symptoms of an inflammatory disease in a subject, comprising administering to the subject a therapeutically effective amount of a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the subject is a mammal. In another embodiment, the subject is a human.

The disorders, diseases, or conditions treatable with a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof, include, but are not limited to, (1) inflammatory or allergic diseases, including systemic anaphylaxis and hypersensitivity disorders, atopic dermatitis, urticaria, drug allergies, insect sting allergies, food allergies (including celiac disease and the like), and mastocytosis; (2) inflammatory bowel diseases, including Crohn's disease, ulcerative colitis, ileitis, and enteritis; (3) vasculitis, and Behcet's syndrome; (4) psoriasis and inflammatory dermatoses, including dermatitis, eczema, atopic dermatitis, allergic contact dermatitis, urticaria, viral cutaneous pathologies including those derived from human papillomavirus, HIV or RLV infection, bacterial, flugal, and other parasital cutaneous pathologies, and cutaneous lupus erythematosus; (5) asthma and respiratory allergic diseases, including allergic asthma, exercise induced asthma, allergic rhinitis, otitis media, allergic conjunctivitis, hypersensitivity lung diseases, and chronic obstructive pulmonary disease; (6) autoimmune diseases, including arthritis (including rheumatoid and psoriatic), systemic lupus erythematosus, type I diabetes, myasthenia gravis, multiple sclerosis, Graves' disease, and glomerulonephritis; (7) graft rejection (including allograft rejection and graft-v-host disease), e.g., skin graft rejection, solid organ transplant rejection, bone marrow transplant rejection; (8) fever; (9) cardiovascular disorders, including acute heart failure, hypotension, hypertension, angina pectoris, myocardial infarction, cardiomyopathy, congestive heart failure, atherosclerosis, coronary artery disease, restenosis, and vascular stenosis; (10) cerebrovascular disorders, including traumatic brain injury, stroke, ischemic reperfusion injury and aneurysm; (11) cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system; (12) fibrosis, connective tissue disease, and sarcoidosis, (13) genital and reproductive conditions, including erectile dysfunction; (14) gastrointestinal disorders, including gastritis, ulcers, nausea, pancreatitis, and vomiting; (15) neurologic disorders, including Alzheimer's disease; (16) sleep disorders, including insomnia, narcolepsy, sleep apnea syndrome, and Pickwick Syndrome; (17) pain; (18) renal disorders; (19) ocular disorders, including glaucoma; and (20) infectious diseases, including HIV.

In certain embodiments, the disorder, disease, or condition is selected from the group consisting of asthma, allergic asthma, exercise induced asthma, allergic rhinitis, perennial allergic rhinitis, seasonal allergic rhinitis, atopic dermatitis, contact hypersensitivity, contact dermatitis, conjunctivitis, allergic conjunctivitis, eosinophilic bronchitis, food allergies, eosinophilic gastroenteritis, inflammatory bowel disease, ulcerative colitis. Crohn's disease, mastocytosis, hyper IgE syndrome, systemic lupus erythematous, psoriasis, acne, multiple sclerosis, allograft rejection, reperfusion injury, chronic obstructive pulmonary disease, Churg-Strauss syndrome, sinusitis, basophilic leukemia, chronic urticaria, basophilic leukocytosis, psoriasis, eczema, COPD (chronic obstructive pulmonary disorder), arthritis, rheumatoid arthritis, psoriatic arthritis, and osteoarthritis.

In certain embodiments, the disorder, disease, or condition is asthma, exercise induced asthma, allergic rhinitis, atopic dermatitis, chronic obstructive pulmonary disease, or allergic conjunctivitis.

Depending on the disorder, disease, or condition to be treated, and the subject's condition, the compounds or pharmaceutical compositions provided herein can be administered by oral, parenteral (e.g., intramuscular, intraperitoneal, intravenous, ICV, intracisternal injection or infusion, subcutaneous injection, or implant), inhalation, nasal, vaginal, rectal, sublingual, or topical (e.g., transdermal or local) routes of administration and can be formulated, alone or together, in suitable dosage unit with pharmaceutically acceptable excipients, carriers, adjuvants, and vehicles appropriate for each route of administration. Also provided is administration of the compounds or pharmaceutical compositions provided herein in a depot formulation, in which the active ingredient is released over a predefined time period.

In the treatment, prevention, or amelioration of one or more symptoms of asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, or other conditions, disorders or diseases associated with a CCR3 receptor, an appropriate dosage level generally is ranging from about 0.001 to 100 mg per kg subject body weight per day (mg/kg per day), from about 0.01 to about 75 mg/kg per day, from about 0.1 to about 50 mg/kg per day, from about 0.5 to about 25 mg/kg per day, or from about 1 to about 20 mg/kg per day, which can be administered in single or multiple doses. Within this range, the dosage can be ranging from about 0.005 to about 0.05, from about 0.05 to about 0.5, from about 0.5 to about 5.0, from about 1 to about 15, from about 1 to about 20, or from about 1 to about 50 mg/kg per day. In certain embodiments, the dosage level is ranging from about 0.001 to about 100 mg/kg per day. In certain embodiments, the dosage level is ranging from about 0.01 to about 75 mg/kg per day. In certain embodiments, the dosage level is ranging from about 0.1 to about 50 mg/kg per day. In certain embodiments, the dosage level is ranging from about 0.5 to about 25 mg/kg per day. In certain embodiments, the dosage level is ranging from about 1 to about 20 mg/kg per day.

For oral administration, the pharmaceutical compositions provided herein can be formulated in the form of tablets containing from about 1.0 to about 1,000 mg of the active ingredient, in one embodiment, about 1, about 5, about 10, about 15, about 20, about 25, about 50, about 75, about 100, about 150, about 200, about 250, about 300, about 400, about 500, about 600, about 750, about 800, about 900, and about 1,000 mg of the active ingredient for the symptomatic adjustment of the dosage to the patient to be treated. The pharmaceutical compositions can be administered on a regimen of 1 to 4 times per day, including once, twice, three times, and four times per day.

It will be understood, however, that the specific dose level and frequency of dosage for any particular patient can be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Also provided herein are methods of modulating CCR3 activity, comprising contacting a CCR3 receptor with a compound provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof. In one embodiment, the CCR3 receptor is expressed by a cell.

The compounds provided herein, e.g., a compound of Formula I, including an enantiomer, a mixture of enantiomers, a mixture of two or more diastereomers, a tautomer, or a mixture of two or more tautomers thereof; or a pharmaceutically acceptable salt, solvate, hydrate, or prodrug thereof, can also be combined or used in combination with other agents useful in the treatment, prevention, or amelioration of one or more symptoms of the disorders, diseases, or conditions for which the compounds provided herein are useful, including asthma, allergic rhinitis, eczema, psoriasis, atopic dermatitis, fever, sepsis, systemic lupus erythematosus, diabetes, rheumatoid arthritis, multiple sclerosis, atherosclerosis, transplant rejection, inflammatory bowel disease, cancer, infectious diseases, and those pathologies noted above.

In certain embodiments, the compounds provided herein can be combined with one or more steroidal drugs known in the art, including, but not limited to the group including, aldosterone, beclometasone, betamethasone, deoxycorticosterone acetate, fludrocortisone, hydrocortisone (cortisol), prednisolone, prednisone, methylprednisolone, dexamethasone, and triamcinolone.

In certain embodiments, the compounds provided herein can be combined with one or more antibacterial agents known in the art, including, but not limited to the group including amikacin, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditorin, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, cloxacillin, colistin, dalfopristin, demeclocycline, dicloxacillin, dirithromycin, doxycycline, erythromycin, enrofloxacin, ertepenem, ethambutol, flucloxacillin, fosfomycin, furazolidone, gatifloxacin, geldanamycin, gentamicin, herbimycin, imipenem, isoniazid, kanamycin, levofloxacin, linezolid, lomefloxacin, loracarbef, mafenide, moxifloxacin, meropenem, metronidazole, mezlocillin, minocycline, mupirocin, nafcillin, neomycin, netilmicin, nitrofurantoin, norfloxacin, ofloxacin, oxytetracycline, penicillin, piperacillin, platensimycin, polymyxin B, prontocil, pyrazinamide, quinupristine, rifampin, roxithromycin, spectinomycin, streptomycin, sulfacetamide, sulfamethizole, sulfamethoxazole, teicoplanin, telithromycin, tetracycline, ticarcillin, tobramycin, trimethoprim, troleandomycin, trovafloxacin, and vancomycin.

In certain embodiments, the compounds provided herein can be combined with one or more antifungal agents known in the art, including, but not limited to the group including amorolfine, amphotericin B, anidulafungin, bifonazole, butenafine, butoconazole, caspofungin, ciclopirox, clotrimazole, econazole, fenticonazole, filipin, fluconazole, isoconazole, itraconazole, ketoconazole, micafungin, miconazole, naftifine, natamycin, nystatin, oxyconazole, ravuconazole, posaconazole, rimocidin, sertaconazole, sulconazole, terbinafine, terconazole, tioconazole, and voriconazole.

In certain embodiments, the compounds provided herein can be combined with one or more anticoagulants known in the art, including, but not limited to the group including acenocoumarol, argatroban, bivalirudin, lepirudin, fondaparinux, heparin, phenindione, warfarin, and ximelagatran.

In certain embodiments, the compounds provided herein can be combined with one or more thrombolytics known in the art, including, but not limited to the group including anistreplase, reteplase, t-PA (alteplase activase), streptokinase, tenecteplase, and urokinase.

In certain embodiments, the compounds provided herein can be combined with one or more non-steroidal anti-inflammatory agents known in the art, including, but not limited to, aceclofenac, acemetacin, amoxiprin, aspirin, azapropazone, benorilate, bromfenac, carprofen, celecoxib, choline magnesium salicylate, diclofenac, diflunisal, etodolac, etoricoxib, faislamine, fenbufen, fenoprofen, flurbiprofen, ibuprofen, indometacin, ketoprofen, ketorolac, lornoxicam, loxoprofen, lumiracoxib, meclofenamic acid, mefenamic acid, meloxicam, metamizole, methyl salicylate, magnesium salicylate, nabumetone, naproxen, nimesulide, oxyphenbutazone, parecoxib, phenylbutazone, piroxicam, salicyl salicylate, sulindac, sulfinpyrazone, suprofen, tenoxicam, tiaprofenic acid, and tolmetin.

In certain embodiments, the compounds provided herein can be combined with one or more antiplatelet agents known in the art, including, but not limited to, abciximab, cilostazol, clopidogrel, dipyridamole, ticlopidine, and tirofibin.

The compounds provided herein can also be administered in combination with other classes of compounds, including, but not limited to, endothelin converting enzyme (ECE) inhibitors, such as phosphoramidon; thromboxane receptor antagonists, such as ifetroban; potassium channel openers;

thrombin inhibitors, such as hirudin; growth factor inhibitors, such as modulators of PDGF activity; platelet activating factor (PAF) antagonists; anti-platelet agents, such as GPIIb/IIIa blockers (e.g., abciximab, eptifibatide, and tirofiban), P2Y (AC) antagonists (e.g., clopidogrel, ticlopidine and CS-747), and aspirin; anticoagulants, such as warfarin; low molecular weight heparins, such as enoxaparin; Factor VIIa Inhibitors and Factor Xa Inhibitors; renin inhibitors; neutral endopeptidase (NEP) inhibitors; vasopeptidase inhibitors (dual NEP-ACE inhibitors), such as omapatrilat and gemopatrilat; HMG CoA reductase inhibitors, such as pravastatin, lovastatin, atorvastatin, simvastatin, NK-104 (a.k.a. itavastatin, nisvastatin, or nisbastatin), and ZD-4522 (also known as rosuvastatin, atavastatin, or visastatin); squalene synthetase inhibitors; fibrates; bile acid sequestrants, such as questran; niacin; anti-atherosclerotic agents, such as ACAT inhibitors; MTP Inhibitors; calcium channel blockers, such as amlodipine besylate; potassium channel activators; alpha-adrenergic agents; beta-adrenergic agents, such as carvedilol and metoprolol; antiarrhythmic agents; diuretics, such as chlorothiazide, hydrochlorothiazide, flumethiazide, hydroflumethiazide, bendroflumethiazide, methylchlorothiazide, trichloromethiazide, polythiazide, benzothiazide, ethacrynic acid, ticrynafen, chlorthalidone, furosenide, muzolimine, bumetanide, triamterene, amiloride, and spironolactone; thrombolytic agents, such as tissue plasminogen activator (tPA), recombinant tPA, streptokinase, urokinase, prourokinase, and anisoylated plasminogen streptokinase activator complex (APSAC); anti-diabetic agents, such as biguanides (e.g., metformin), glucosidase inhibitors (e.g., acarbose), insulins, meglitinides (e.g., repaglinide), sulfonylureas (e.g., glimepiride, glyburide, and glipizide), thiozolidinediones (e.g., troglitazone, rosiglitazone, and pioglitazone), and PPAR-gamma agonists; mineralocorticoid receptor antagonists, such as spironolactone and eplerenone; growth hormone secretagogues; aP2 inhibitors; phosphodiesterase inhibitors, such as PDE III inhibitors (e.g., cilostazol) and PDE V inhibitors (e.g., sildenafil, tadalafil, and vardenafil); protein tyrosine kinase inhibitors; antiinflammatories; antiproliferatives, such as methotrexate, FK506 (tacrolimus), mycophenolate mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes); antimetabolites, such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone antagonists, and octreotide acetate; microtubule-disruptor agents, such as ecteinascidins; microtubule-stabilizing agents, such as pacitaxel, docetaxel, and epothilones A-F; plant-derived products, such as vinca alkaloids, epipodophyllotoxins, and taxanes; and topoisomerase inhibitors; prenyl-protein transferase inhibitors; and cyclosporins; steroids, such as prednisone and dexamethasone; cytotoxic drugs, such as azathioprine and cyclophosphamide; TNF-alpha inhibitors, such as tenidap; anti-TNF antibodies or soluble TNF receptor, such as etanercept, rapamycin, and leflunimide; and cyclooxygenase-2 (COX-2) inhibitors, such as celecoxib and rofecoxib; and miscellaneous agents such as, hydroxyurea, procarbazine, mitotane, hexamethylmelamine, gold compounds, platinum coordination complexes, such as cisplatin, satraplatin and carboplatin.

Such other agents, or drugs, can be administered, by a route and in an amount commonly used therefor, simultaneously or sequentially with the compounds provided herein, e.g., a compound of Formula I, including a single enantiomer, a mixture of enantiomers, or a mixture of diastereomers thereof; or a pharmaceutically acceptable salt, solvate, or prodrug thereof. When a compound provided herein is used contemporaneously with one or more other drugs, a pharmaceutical composition containing such other drugs in addition to the compound provided herein can be utilized, but is not required. Accordingly, the pharmaceutical compositions provided herein include those that also contain one or more other active ingredients or therapeutic agents, in addition to a compound provided herein.

The weight ratio of a compound provided herein to the second active ingredient can be varied, and will depend upon the effective dose of each ingredient. Generally, an effective dose of each will be used. Thus, for example, when a compound provided herein is combined with a NSAID, the weight ratio of the compound to the NSAID can range from about 1,000:1 to about 1:1,000, or about 200:1 to about 1:200. Combinations of a compound provided herein and other active ingredients will generally also be within the aforementioned range, but in each case, an effective dose of each active ingredient should be used.

The compounds provided herein can also be provided as an article of manufacture using packaging materials well known to those of skill in the art. See, e.g., U.S. Pat. Nos. 5,323,907; 5,052,558; and 5,033,252. Examples of pharmaceutical packaging materials include, but are not limited to, blister packs, bottles, tubes, inhalers, pumps, bags, vials, containers, syringes, and any packaging material suitable for a selected formulation and intended mode of administration and treatment.

Provided herein also are kits which, when used by the medical practitioner, can simplify the administration of appropriate amounts of active ingredients to a subject. In certain embodiments, the kit provided herein includes a container and a dosage form of a compound provided herein, including a single enantiomer or a mixture of diastereomers thereof; or a pharmaceutically acceptable salt, solvate, or prodrug thereof.

In certain embodiments, the kit includes a container comprising a dosage form of the compound provided herein, including a single enantiomer or a mixture of diastereomers thereof; or a pharmaceutically acceptable salt, solvate, or prodrug thereof, in a container comprising one or more other therapeutic agent(s) described herein.

Kits provided herein can further include devices that are used to administer the active ingredients. Examples of such devices include, but are not limited to, syringes, needle-less injectors drip bags, patches, and inhalers. The kits provided herein can also include condoms for administration of the active ingredients.

Kits provided herein can further include pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: aqueous vehicles, including, but not limited to, Water for Injection USP, Sodium Chloride Injection, Ringer's Injection, Dextrose Injection, Dextrose and Sodium Chloride Injection, and Lactated Ringer's Injection; water-miscible vehicles, including, but not limited to, ethyl alcohol, polyethylene glycol, and polypropylene glycol; and non-aqueous vehicles, including, but not limited to, corn oil, cottonseed oil, peanut oil, sesame oil, ethyl oleate, isopropyl myristate, and benzyl benzoate.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: g (grams); mg (milligrams); mL (milliliters); μL (microliters); mM (millimolar); μM (micromolar); eq. (equivalent); Hz (Hertz); MHz (megahertz); mmol (millimoles); hr or hrs (hours); min (minutes); MS (mass spectrometry); ESI (electrospray ionization); TLC (thin layer chromatography); $R_f$ (retention time); $SiO_2$ (silica); THF (tetrahydrofuran); DCM (dichloromethane); DMSO (dimethylsulfoxide); DMSO-$d_6$ (deuterated dimethylsulfoxide); EtOAc (ethyl acetate); EtOH (ethanol); $Et_2O$, (diethylether); HCl (hydrochloric acid); $K_2CO_3$ (potassium carbonate); NaOH, (sodium hydroxide); $Na_2SO_4$ (sodium sulfate); NaCl, (sodium chloride); $MgSO_4$ (magnesium sulfate); NaH (sodium hydride); $NaHCO_3$ (sodium bicarbonate); TEA (triethylamine); $NaNO_2$, (sodium nitrite); $CuCl_2$, (copper(II) chloride); $SO_2$, (sulfur dioxide); Me (methyl); Et (ethyl); tBu (tert-butyl); and Boc (tert-butoxylcarbony).

For all of the following examples, standard work-up and purification methods known to those skilled in the art can be utilized. Unless otherwise indicated, all temperatures are expressed in ° C. (degrees Centigrade). All reactions are conducted at room temperature unless otherwise noted. Synthetic methodologies illustrated herein are intended to exemplify the applicable chemistry through the use of specific examples and are not indicative of the scope of the disclosure.

Example 1

Preparation of 4-(2,5-difluorophenoxy)-3-(4-(dimethylamino)piperidin-1-ylsulfonyl)benzonitrile

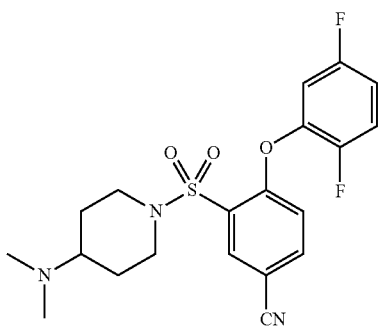

59

Compound 59 was synthesized as shown in Scheme 3.

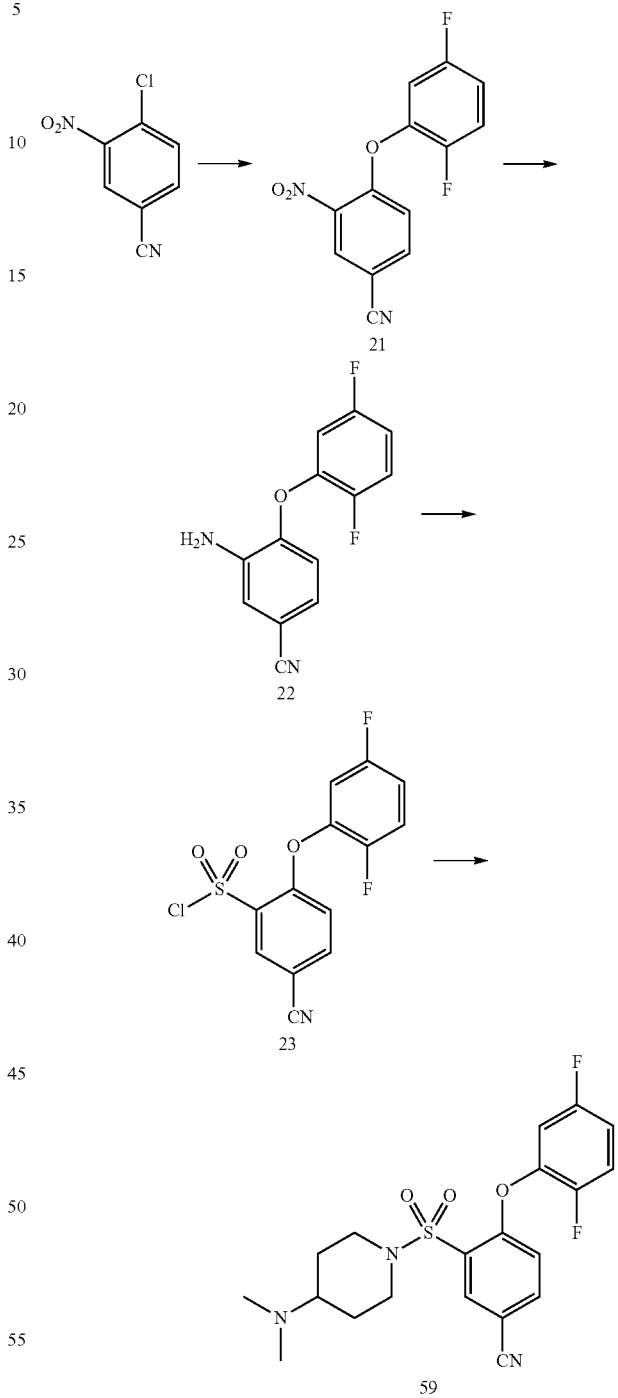

Scheme 3

4-(2,5-Difluorophenoxy)-3-nitrobenzonitrile 21. A solution of 4-chloro-3-nitrobenzonitrile (5 g) in THF (200 mL) at room temperature was treated with $K_2CO_3$ (19 g), followed by 2,5-difluorophenol (3.7 g). After stirring at room temperature for 18 hrs, the solid was filtered off and rinsed with copious amounts of EtOAc. The filtrate was washed sequentially with saturated aqueous $NaHCO_3$ solution, water, and saturated aqueous NaCl solution, dried over anhydrous $Na_2SO_4$, filtered, and concentrated in vacuo. The residual was triturated with hexanes and collected by suction to furnish the desired product 21, which was used directly in the next step without further purification.

3-Amino-4-(2,5-difluorophenoxy)benzonitrile 22. A mixture of Tin (II) chloride dihydrate (18.238 g, 81.00 mmol) in EtOH (65.00 mL) and HCl (12 M, 10.00 mL) was stirred at 70° C. until the solution became clear. Compound 21 (5.60 g, 20.28 mmol) was then added over 10 min. The solution was kept slightly refluxing during addition. The reaction was monitored with TCL (25% EtOAc in hexanes, $R_f$=0.65). The reaction was complete after refluxing for 1.5 hrs, as indicated by the absence of the starting material (TLC). Water (80 mL) was added and the resulting solution was allowed to cool to room temperature. The desired product was precipitated out as a white solid during cooling. The mixture was further cooled and stirred for 30 min at 15° C. The resulting precipitation was collected via filtration under vacuum, washed with water, and dried under vacuum to yield compound 22 as a white solid (3.60 g, 99.0% HPLC purity, 63% yield). $^1$H NMR (500 MHz, DMSO-$d_6$): δ 7.44 (m, 1H), 7.09 (m, 2H), 7.04 (m, 1H), 6.92 (dd, $J_1$=2 Hz, $J_2$=8 Hz, 1H), 6.78 (d, J=8 Hz, 1H), 5.65 (s, 2H).

5-Cyano-2-(2,5-difluorophenoxy)benzene-1-sulfonyl chloride 23. To a solution of compound 22 (4.20 g, 14.86 mmol) in acetic acid (50.00 mL) was added HCl (12 M, 40.00 mL). The solution was stirred in an ice bath. A solution of NaNO$_2$ (1.230 g, 17.83 mmol) in water (5 mL) was added dropwise to the compound 22 containing solution with stirring. The reaction mixture was stirred in an ice bath for additional 2 hrs. In a separate flask, SO$_2$ was bubbled through acetic acid (100 mL) for 45 min to form a SO$_2$ saturated solution. CuCl$_2$ (1.267 g, 7.43 mmol) was then added to the SO$_2$ saturated solution and stirred for an additional 15 min. The CuCl$_2$ solution was then cooled with an ice bath and stirred for 10 min. The solution containing compound 22 was then added dropwise into the CuCl$_2$ solution. After the addition, the solution was stirred for additional 45 min, and then poured onto ice water and stirred for 1 hr. The resulting orange precipitate was collected through filtration. The solid (3.5 g) was dissolved in minimal amount of DCM and purified with chromatography eluted with DCM. Pure fractions were combined and evaporated in vacuo. The resulting solid was triturated with DCM and hexanes, and filtered to obtain compound 23 as a yellow/white solid (0.600 g, 95% HPLC purity, 12.2% yield). A second trituration of the filtrate yielded 150 mg of impure product.

4-(2,5-Difluorophenoxy)-3-(4-(dimethylamino)piperidin-1-ylsulfonyl)benzonitrile 59. To a solution of compound 23 (0.080 g, 0.24 mmol) in DCM (10.00 mL) was added 4-dimethylaminopiperidine (0.040 g, 0.31 mmol) and TEA (0.043 g, 0.31 mmol). The reaction was monitored with TLC (25% EtOAc in hexanes, Rf=0.0). The reaction was complete after stirring at room temperature for 30 min, as indicated by the absence of the starting material (TLC). Water was then added and extracted twice with DCM. Combined organic extracts were washed sequentially with water and brine, dried over MgSO$_4$, filtered, and evaporated in vacuo to form a yellow oil. The oil was triturated with DCM and hexanes, and filtered to yield compound 59 as a white powder (0.85 g, 97.4% HPLC purity, 84% yield). $^1$H NMR (500 MHz, DMSO-$d_6$): δ 8.27 (d, J=2 Hz, 1H), 8.08 (dd, $J_1$=2 Hz, $J_2$=8 Hz, 1H), 7.56 (m, 1H), 7.40 (m, 1H), 7.26 (m, 1H), 7.19 (d, J=9 Hz, 1H), 3.71 (d, J=13 Hz, 2H), 2.77 (t, J=13 Hz, 2H), 2.18 (m, 1H), 2.12 (s, 3H), 1.76 (d, J=11 Hz, 2H), 1.35 (m, 2H); MS (ESI, EI$^+$): m/z=422 (MH$^+$); melting point: 154-157° C.

4-(2,5-Difluorophenoxy)-3-(4-(dimethylamino)piperidin-1-ylsulfonyl)benzonitrile, hydrochloride 59. To a solution of neutral compound 59 (25.0 mg, 0.06 mmol) in 1,4-dioxane (2.0 mL) was added 4 N HCl in 1,4-dioxane (60.0 μL, 0.24 mmol). The reaction mixture was stirred for 10 min at room temperature before adding 2 mL of diethyl ether. A white precipitate formed and collected via filtration to obtain compound 59 hydrochloride as a white solid (25.0 mg, 100% HPLC purity, 91% yield). $^1$H NMR (500 MHz, DMSO-$d_6$): δ 10.78 (s, 1H), 8.30 (d, J=2 Hz, 1H), 8.10 (dd, $J_1$=2 Hz, $J_2$=8 Hz, 1H), 7.55 (m, 1H), 7.47 (m, 1H), 7.28 (m, 1H), 7.20 (d, J=8 Hz, 1H), 3.89 (m, 2H), 3.25 (m, 1H), 2.78 (t, $J_1$=$J_2$=12 Hz, 2H), 2.68 (s, 6H), 2.11 (m, 2H), 1.64 (m, 2H); MS (ESI, EI$^+$): m/z=422 (MH$^+$); melting point: 250-252° C.

The following compounds were made according to the procedures as described in this example.

4-(2,5-Difluorophenoxy)-3-(piperazin-1-ylsulfonyl)benzonitrile, dihydrochloride 52. HPLC purity: 100%; $^1$H NMR (500 MHz, DMSO-$d_6$): δ 9.41 (s, 2H), 8.31 (d, J=2 Hz, 1H), 8.13 (dd, $J_1$=2 Hz, $J_2$=8 Hz, 1H), 7.55 (m, 2H), 7.29 (m, 1H), 7.21 (d, J=8 Hz, 1H), 3.50 (m, 4H), 3.16 (m, 4H); MS (ESI, EI$^+$): m/z=380 (MH$^+$); melting point: 125-143° C.

4-(2,5-Difluorophenoxy)-3-(3,5-dimethylpiperazin-1-ylsulfonyl)benzonitrile 53. HPLC purity: 100%; $^1$H NMR (500 MHz, DMSO-$d_6$): δ 8.27 (d, J=2 Hz, 1H), 8.09 (dd, $J_1$=2 Hz, $J_2$=8 Hz, 1H), 7.56 (m, 1H), 7.35 (m, 1H), 7.24 (m, 1H), 3.55 (m, 2H), 2.69 (m, 2H), 2.17 (t, $J_1$=$J_2$=11 Hz, 3H), 0.91 (d, J=8 Hz, 6H); MS (ESI, EI$^+$): m/z=408 (MH$^+$); melting point: 157-159° C.

4-(2,5-Difluorophenoxy)-3-(3,5-dimethylpiperazin-1-ylsulfonyl)benzonitrile, dihydrochloride 53. HPLC purity: 100%; $^1$H NMR (500 MHz, DMSO-$d_6$): δ 9.50 (m, 1H), 9.26 (m, 1H), 8.31 (d, J=2 Hz, 1H), 8.13 (dd, $J_1$=2 Hz, $J_2$=8 Hz, 1H), 7.58 (m, 1H), 7.51 (m, 1H), 7.28 (m, 1H), 7.23 (d, J=8 Hz, 1H), 3.87 (m, 2H), 2.89 (t. $J_1$=$J_2$=12 Hz, 2H), 1.23 (d, J=6 Hz, 6H); MS (ESI, EI$^+$): m/z=408 (MH$^+$).

4-(2,5-Difluorophenoxy)-3-(4-isopropylpiperazin-1-ylsulfonyl)benzonitrile 54. HPLC purity: 99%; $^1$H NMR (500 MHz, DMSO-$d_6$): δ 8.26 (d, J=2 Hz, 1H), 8.09 (dd, $J_1$=2 Hz, $J_2$=8 Hz, 1H), 7.56 (m, 1H), 7.42 (m, 1H), 7.25 (m, 1H), 7.21 (d, J=8 Hz, 1H), 3.18 (m, 4H), 2.65 (m, 1H), 2.46 (m, 4H), 0.92 (d, J=7 Hz, 6H); melting point: 179-182° C.

4-(2,5-Difluorophenoxy)-3-(4-isopropylpiperazin-1-ylsulfonyl)benzonitrile, hydrochloride 54. HPLC purity: 100%; $^1$H NMR (500 MHz, DMSO-$d_6$): δ 11.00 (s, 1H), 8.33 (d, J=2 Hz, 1H), 8.12 (dd, $J_1$=2 Hz, $J_2$=8 Hz, 1H), 7.64 (m, 1H), 7.57 (m, 1H), 7.30 (m, 1H), 7.20 (d, J=8 Hz, 1H), 3.88 (m, 2H), 3.48 (m, 3H), 3.40 (m, 2H), 3.08 (m, 2H), 1.26 (d, J=7 Hz, 6H); MS (ESI, EI$^+$): m/z=422 (MH$^+$).

4-(2,5-Difluorophenoxy)-3-(4-(pentan-3-yl)piperazin-1-ylsulfonyl)benzonitrile 55. HPLC purity: 97%; $^1$H NMR (500 MHz, DMSO-$d_6$): δ 8.26 (d, J=2 Hz, 1H), 8.09 (dd, $J_1$=2 Hz, $J_2$=8 Hz, 1H), 7.56 (m, 1H), 7.39 (m, 1H), 7.26 (m, 1H), 7.21 (d, J=8 Hz, 1H), 3.16 (m, 4H), 2.50 (m, 4H), 2.13 (m, 1H), 1.37 (m, 2H), 1.22 (m, 2H), 0.81 (t, $J_1$=$J_2$=7 Hz, 6H); melting point: 107-109° C.

4-(2,5-Difluorophenoxy)-3-(4-(pentan-3-yl)piperazin-1-ylsulfonyl)benzonitrile, hydrochloride 55. HPLC purity: 100%; $^1$H NMR (500 MHz, DMSO-$d_6$): δ 10.72 (s, 1H), 8.32 (d, J=2 Hz, 1H), 8.13 (dd, $J_1$=2 Hz, $J_2$=8 Hz, 1H), 7.67 (m, 1H), 7.57 (m, 1H), 7.30 (m, 1H), 7.21 (d, J=8 Hz, 1H), 3.84 (m, 2H), 3.49 (m, 4H), 3.06-3.17 (m, 3H), 1.83 (m, 2H), 1.61 (m, 2H), 0.94 (t, $J_1$=J2=7 Hz, 6H); MS (ESI, EI$^+$): m/z=450 (MH$^+$); melting point: 206-209° C.

3-(4-Cyclopentylpiperazin-1-ylsulfonyl)-4-(2,5-difluorophenoxy)benzonitrile 56. HPLC purity: 99%; $^1$H NMR (500 MHz, DMSO-$d_6$): δ 8.26 (d, J=2 Hz, 1H), 8.09 (dd, $J_1$=2 Hz, $J_2$=8 Hz, 1H), 7.56 (m, 1H), 7.43 (m, 1H), 7.26 (m, 1H), 7.20 (d, J=8 Hz, 1H), 3.19 (m, 4H), 2.46 (m, 5H), 1.72 (m, 2H), 1.56 (m, 2H), 1.47 (m, 2H), 1.26 (m, 2H); MS (ESI, EI⁺): m/z=448 (MH⁺); melting point: 158-160° C.

3-(4-Cyclopentylpiperazin-1-ylsulfonyl)-4-(2,5-difluorophenoxy)benzonitrile, hydrochloride 56. HPLC purity: 100%; ¹H NMR (500 MHz, DMSO-d₆): δ 11.06 (s, 1H), 8.32 (d, J=2 Hz, 1H), 8.13 (dd, J₁=2 Hz, J₂=8 Hz, 1H), 7.60 (m, 2H), 7.30 (m, 1H), 7.21 (d, J=8 Hz, 1H), 3.87 (m, 2H), 3.52 (m, 3H), 3.32 (m, 2H), 3.10 (m, 2H), 1.97 (m, 2H), 1.72 (m, 4H), 1.53 (m, 2H); MS (ESI, EI⁺): m/z=448 (MH⁺).

4-(2,5-Difluorophenoxy)-3-(4-methyl-1,4-diazepan-1-ylsulfonyl)benzonitrile, hydrochloride 57. HPLC purity: 100%; ¹H NMR (500 MHz, DMSO-d₆): δ 10.68 (s, 1H), 8.30 (d, J=2 Hz, 1H), 8.09 (dd, J₁=2 Hz, J₂=8 Hz, 1H), 7.58 (m, 1H), 7.52 (m, 1H), 7.30 (m, 1H), 7.18 (d, J=8 Hz, 1H), 3.88 (, 1H), 3.49-3.59 (m, 4H), 3.36 (m, 1H), 3.26 (m, 1H), 3.18 (m, 1H), 2.79 (s, 3H), 2.15 (m, 2H); MS (ESI, EI⁺): m/z=408 (MH⁺); melting point: 238-242° C.

4-(2,5-Difluorophenoxy)-3-(morpholinosulfonyl)benzonitrile 58. HPLC purity: 99%; ¹H NMR (500 MHz, DMSO-d₆): δ 8.28 (d, J=2 Hz, 1H), 8.10 (dd, J₁=2 Hz, J₂=8 Hz, 1H), 7.57 (m, 1H), 7.47 (m, 1H), 7.27 (m, 1H), 7.20 (d, J=8 Hz, 1H), 3.62 (m, 4H), 3.20 (m, 4H); melting point: 165-168° C.

4-(2,5-Difluorophenoxy)-3-(4-(pyrrolidin-1-ylpiperidin-1-ylsulfonyl)benzonitrile 60. HPLC purity: 99%; ¹H NMR (500 MHz, DMSO-d₆): δ 8.27 (d, J=2 Hz, 1H), 8.08 (dd, J₁=2 Hz, J₂=8 Hz, 1H), 7.55 (m, 1H), 7.38 (m, 1H), 7.25 (m, 1H), 7.20 (dd, J₁=2 Hz, J₂=8 Hz, 1H), 3.60 (m, 2H), 2.87 (m, 2H), 2.44 (m, 4H), 2.10 (s, 1H), 1.85 (m, 2H), 1.64 (m, 4H), 1.40 (m, 2H); MS (ESI, EI⁺): m/z=448 (MH⁺); melting point: 189-192° C.

4-(2,5-Difluorophenoxy)-3-(4-(pyrrolidin-1-yl)piperidin-1-ylsulfonyl)benzonitrile, hydrochloride 60. HPLC purity: 100%; ¹H NMR (500 MHz, DMSO-d₆): δ 10.92 (m, 1H), 8.30 (d, J=2 Hz, 1H), 8.09 (dd, J₁=2 Hz, J₂=8 Hz, 1H), 7.49-7.58 (m, 2H), 7.29 (m, 1H), 7.20 (d, J=8 Hz, 1H), 3.86 (m, 2H), 3.44 (m, 2H), 3.20 (m, 1H), 3.00 (m, 2H), 2.78 (t, J₁=J₂=12 Hz, 2H), 2.12 (m, 2H), 1.92 (m, 2H), 1.85 (m, 2H), 1.70 (m, 2H); MS (ESI, EI⁺): m/z=448 (MH⁺); melting point: 260-263° C.

5-Cyano-N-(2-(diethylamino)ethyl)-2-(2,5-difluorophenoxy)benzenesulfonamide, hydrochloride 62. HPLC purity: 100%; ¹H NMR (500 MHz, DMSO-d₆): δ 10.47 (s, 1H), 8.39 (t, J₁=J₂=6 Hz, 1H), 8.27 (d, J=2 Hz, 1H), 8.08 (dd, J₁=2 Hz, J₂=8 Hz, 1H), 7.55 (m, 1H), 7.50 (m, 1H), 7.30 (m, 1H), 7.12 (d, J=8 Hz, 1H), 3.30 (m, 2H), 3.14 (m, 6H), 1.20 (t, J₁=J₂=7 Hz, 6H); MS (ESI, EI⁺): m/z=410 (MH⁺); melting point: 180-182° C.

5-Cyano-2-(2,5-difluorophenoxy)-N-(2-(pyrrolidin-1-yl)ethyl)benzenesulfonamide 63. HPLC purity: 100%; ¹H NMR (500 MHz, DMSO-d₆): δ 8.26 (d, J=2 Hz, 1H), 8.02 (dd, J₁=2 Hz, J₂=8 Hz, 1H), 7.56 (m, 1H), 7.36 (m, 1H), 7.27 (m, 1H), 7.07 (d, J=8 Hz, 1H), 3.06 (t, J₁=J₂=7 Hz, 2H), 2.42 (t, J₁=J₂=7 Hz, 2H), 2.29 (s, 4H), 1.56 (s, 4H); MS (ESI, EI⁺): m/z=408 (MH⁺); melting point: 122-125° C.

5-Cyano-2-(2,5-difluorophenoxy)-N-(2-(pyrrolidin-1-yl)ethyl)benzenesulfonamide, hydrochloride 63. HPLC purity: 100%; ¹H NMR (500 MHz, DMSO-d₆): δ 10.46 (s, 1H), 8.38 (m, 1H), 8.27 (d, J=2 Hz, 1H), 8.08 (dd, J₁=2 Hz, J₂=8 Hz, 1H), 7.55 (m, 1H), 7.50 (m, 1H), 7.30 (m, 1H), 7.12 (d, J=7 Hz, 1H), 3.55 (m, 2H), 3.26 (m, 4H), 3.00 (m, 2H), 1.98 (m, 2H), 1.86 (m, 2H); MS (ESI, EI⁺): m/z=408 (MH⁺); melting point: 229-232° C.

5-Cyano-2-(2,5-difluorophenoxy)-N-(2-(piperidin-1-yl)ethyl)benzenesulfonamide 64. HPLC purity: 99.5%; ¹H NMR (500 MHz, DMSO-d₆): δ 8.25 (d, J=2 Hz, 1H), 8.03 (dd, J₁=2 Hz, J₂=8 Hz, 1H), 7.8-7.9 (stretched peak, 1H), 7.56 (m, 1H), 7.37 (m, 1H), 7.27 (m, 1H), 7.10 (dd, J₁=2 Hz, J₂=8 Hz, 1H), 3.03 (t, J₁=J₂=7 Hz, 2H), 2.29 (t, J₁=J₂=7 Hz, 2H), 2.21 (s, 4H), 1.24-1.38 (m, 6H); MS (ESI, EI⁺): m/z=422 (MH⁺); melting point: 70-80° C.

5-Cyano-2-(2,5-difluorophenoxy)-N-(2-(piperidin-1-yl)ethyl)benzenesulfonamide, hydrochloride 64. HPLC purity: 100%; ¹H NMR (500 MHz, DMSO-d₆): δ 10.10 (s, 1H), 8.38 (t. J₁=J₂=6 Hz, 1H), 8.26 (d, J=2 Hz, 1H), 8.08 (dd, J₁=2 Hz, J₂=8 Hz, 1H), 7.55 (m, 1H), 7.50 (m, 1H), 7.30 (m, 1H), 7.12 (d, J=7 Hz, 1H), 3.42 (m, 2H), 3.32 (m, 2H), 3.14 (m, 2H), 2.89 (m, 2H), 1.66-1.78 (m, 5H), 1.36 (m, 1H); MS (ESI, EI⁺): m/z=422 (MH⁺); melting point: 210-213° C.

Example 2

Preparation of 3-(4-(dimethylamino)piperidin-1-ylsulfonyl)-4-(2,5-dimethylphenylthio)benzonitrile

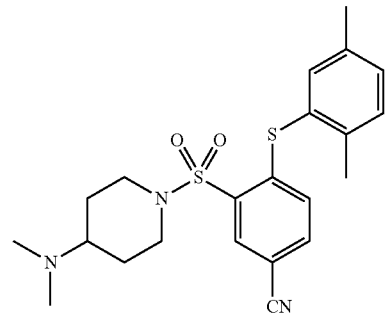

72

Compound 72 was synthesized as shown in Scheme 4.

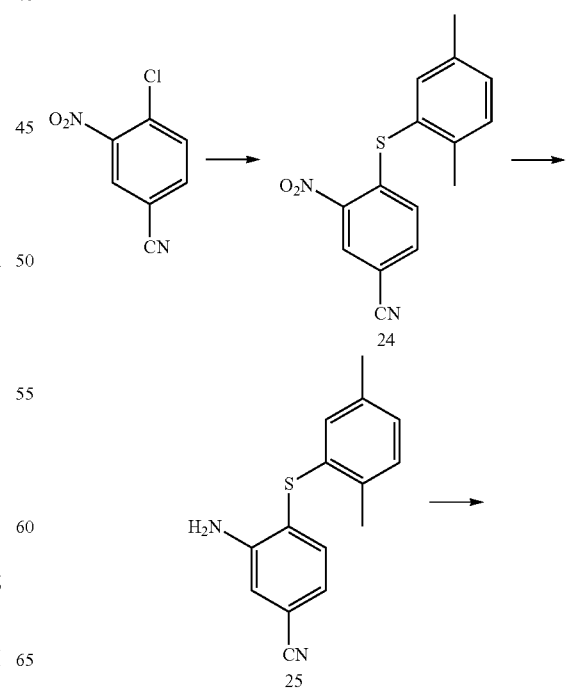

Scheme 4

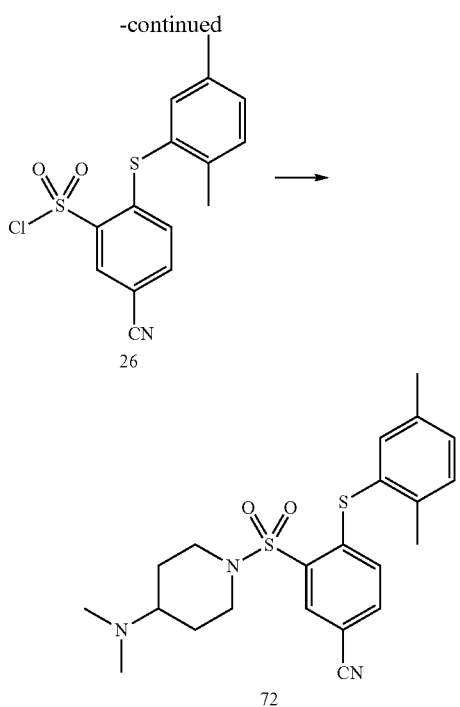

4-(2,5-Dimethylphenylthio)-3-nitrobenzonitrile 24. To a solution of 4-chloro-3-nitrobenzonitrile (5.4 g, 29.67 mmol) in THF (100 mL) was added 2,5-dimethylthiophenol (4.921 g, 35.60 mmol) and $K_2CO_3$ (20.45 g, 148.0 mmol). The reaction was monitored with TLC (25% EtOAc in hexanes). After refluxing for 16 hrs, the reaction was complete. The solid was filtered and washed with copious amounts of EtOAc. The filtrate was washed sequentially with saturated $NaHCO_3$, water, saturated NaCl solution, dried over $MgSO_4$, filtered, and evaporated in vacuo. The resulting solid was then sonicated in hexanes and filtered to yield compound 24 as a yellow/white solid (8.00 g, 97.8% HPLC purity, 95% yield). $^1$H NMR (500 MHz, DMSO-$d_6$): δ8.77 (d, J=2 Hz, 1H), 7.94 (dd, $J_1$=2 Hz, $J_2$=8 Hz, 1H), 7.46 (s, 1H), 7.41 (d, J=8 Hz, 1H), 7.36 (d, J=8 Hz, 1H), 6.76 (d, J=8 Hz, 1H), 2.32 (s, 3H), 2.23 (s, 3H).

3-Amino-4-(2,5-dimethylphenylthio)benzonitrile 25. A mixture of Tin (II) chloride dihydrate (25.218 g, 112.0 mmol) in EtOH (85.0 mL) and conc. HCl (12 M, 15.0 mL) was stirred at 70° C. until a clear solution was formed. Compound 24 (8.0 g, 28.14 mmol) was then added over 10 min. The solution was kept slightly refluxing during addition. The reaction was monitored with TLC (25% EtOAc in hexanes, $R_f$=0.65). The reaction was complete after refluxing for 1.5 hrs as indicated by the absence of the starting material (TLC). Water (35 mL) was added and the resulting solution was allowed to cool to room temperature. Precipitation occurred during cooling. The mixture was further cooled and stirred for 30 min at 15° C. The precipitate was filtered, washed with water, and dried under vacuum to yield compound 25 as a white solid (5.30 g, 95% HPLC purity, 65% yield). $^1$H NMR (500 MHz, DMSO-$d_6$): δ 7.20 (d, J=8 Hz, 1H), 7.07 (d, J=2 Hz, 1H), 7.04 (d, J=8 Hz, 1H), 7.00 (d, J=8 Hz, 1H), 6.90 (dd, $J_1$=2 Hz, $J_2$=8 Hz, 1H), 6.85 (s, 1H), 5.72 (s, 2H), 2.26 (s, 3H), 2.18 (s, 3H).

5-Cyano-2-(2,5-dimethylphenylthio)benzene-1-sulfonyl chloride 26. To a solution of compound 25 (5.00 g, 17.19 mmol) in acetic acid (80 mL) was added hydrochloric acid ((12 M, 50.0 mL). The mixture was stirred in an ice bath. A solution of $NaNO_2$ (2.97 g, 43.00 mmol) in water (7 mL) was added dropwise to the compound 25-containing solution stirred in an ice bath. After addition, the resulting solution was stirred in an ice bath for 1 hr. In a separate flask, $SO_2$ was bubbled through acetic acid (40 mL) for 45 min at room temperature to form a saturated $SO_2$ solution. Copper II chloride dihydrate (1.47 g, 8.60 mmol) was then added to the $SO_2$ saturated solution and stirred for an additional 15 min. The saturated $SO_2$ solution was then cooled with an ice bath and stirred for 10 min. The compound 25-containing solution was then added dropwise into the $SO_2$ saturated solution. After the addition, the solution was stirred for additional 45 min. The reaction mixture was then poured onto ice water and stirred for 1 hr. The resulting precipitate was filtered to yield compound 26 as an orange solid (2.00 g, 65% HPLC purity, 35% yield).

3-(4-(Dimethylamino)piperidin-1-ylsulfonyl)-4-(2,5-dimethylphenylthio)-benzonitrile 72. To a solution of compound 26 (0.200 g, 0.59 mmol) in DCM was added TEA (0.090 g, 0.89 mmol) and 4-dimethylaminopiperidine (0.114 g, 0.89 mmol). The reaction was monitored by HPLC. The reaction was complete after stirring at room temperature for 16 hrs. DCM was removed in vacuo, and the resulting solid was dissolved in a minimal amount of DCM and purified with chromatography with a gradient of 10 to 30% MeOH in DCM. Pure fractions were combined and evaporated in vacuo to yield an oil, which was triturated with DCM and hexanes, and then filtered to yield compound 72 as a peach solid (0.124 g, 49% yield). HPLC purity: 96.5%; $^1$H NMR (500 MHz, DMSO-$d_6$): δ 8.22 (d, J=2 Hz, 1H), 7.84 (dd, $J_1$=2 Hz, $J_2$=8 Hz, 1H), 7.41 (d, J=6 Hz, 1H), 7.39 (s, 1H), 7.34 (d, J=8 Hz, 1H), 6.70 (d, J=8 Hz, 1H), 3.8 (d, J=13 Hz, 2H), 2.84 (t, J=12 Hz, 2H), 2.31 (s, 3H), 2.26 (m, 1H), 2.25 (s, 3H), 2.15 (s, 6H), 1.79 (d, J=12 Hz, 2H), 1.43 (m, 2H); MS (ESI, EI$^+$): m/z=430 (MH$^+$); melting point: 136-139° C.

3-(4-(Dimethylamino)piperidin-1-ylsulfonyl)-4-(2,5-dimethylphenylthio)-benzonitrile, hydrochloride 72. To a solution of neutral compound 72 (30.0 mg, 0.07 mmol) in 1,4-dioxane (2.0 mL) and added 4 N HCl in 1,4-dioxane (60.0 μL, 0.24 mmol). The reaction mixture was stirred for 10 min at room temperature before adding 2 mL of diethyl ether. A white precipitate was formed and collected via filtration to obtain compound 72 hydrochloride as a white solid (32.0 mg, 97.6% HPLC purity, 100% yield). $^1$H NMR (500 MHz, DMSO-$d_6$): δ 10.62 (m, 1H), 8.24 (d, J=2 Hz, 1H), 7.86 (dd, $J_1$=2 Hz, $J_2$=8 Hz, 1H), 7.44 (s, 1H), 7.40 (d, J=8 Hz, 1H), 7.34 (d, J=8 Hz, 1H), 6.71 (d, J=8 Hz, 1H), 3.96 (m, 2H), 3.31 (m, 1H), 2.84 (m, 2H), 2.70 (d, J=5 Hz, 2.32 (s, 3H), 2.23 (s, 3H), 2.13 (m, 2H), 1.68 (m, 2H); MS (ESI, EI$^+$): m/z=430 (MH$^+$); melting point: 242-244° C.

The following compounds were made according to the procedures as described in this example.

4-(2,5-Dimethylphenylthio)-3-(piperazin-1-ylsulfonyl) benzonitrile 65. HPLC purity: 98.7%; $^1$H NMR (500 MHz, DMSO-$d_6$): δ 8.19 (s, 1H), 7.85 (dd, $J_1$=2 Hz, $J_2$=8 Hz, 1H), 7.42 (d, J=8 Hz, 1H), 7.39 (s, 1H), 7.34 (d, $J_7$=8 Hz, 1H), 6.70 (d, J=8 Hz, 1H), 3.15 (m, 4H), 2.75 (m, 4H), 2.32 (s, 3H), 2.23 (s, 3H); MS (ESI, EI$^+$): m/z=388 (MH$^+$); melting point: 192-195° C.

Tert-butyl-4-(5-cyano-2-(2,5-dimethylphenylthio)phenylsulfonyl)piperazine-1-carboxylate. HPLC purity: 100%; $^1$H NMR (500 MHz, DMSO-$d_6$): δ 8.20 (d, J=2 Hz, 1H), 7.85 (dd, $J_1$=2 Hz, $J_2$=8 Hz, 1H), 7.45 (s, 1H), 7.39 (d, J=8 Hz, 1H), 7.33 (d, J=8 Hz, 1H), 6.70 (d, J=8 Hz, 1H), 3.42 (m, 4H), 3.26 (m, 4H), 2.31 (s, 3H), 2.22 (s, 3H), 1.38 (s, 9H); MS (ESI, EI$^+$): m/z=430 (MH$^+$).

4-(2,5-Dimethylphenylthio)-3-(3,5-dimethylpiperazin-1-ylsulfonyl)-benzonitrile 66. HPLC purity: 100%; ¹H NMR (500 MHz, DMSO-d₆): δ 8.20 (s, 1H), 7.84 (d, J=8 Hz, 1H), 7.40 (d, J=9 Hz, 2H), 7.34 (d, J=8 Hz, 1H), 6.69 (d, J=8 Hz, 1H), 3.66 (d, J=12 Hz, 2H), 2.73 (m, 2H), 2.32 (s, 3H), 2.21 (s, 3H), 2.19 (s, 1H), 2.17 (s, 2H), 0.95 (d, J=6 Hz, 6H); MS (ESI, EI⁺): m/z=416 (MH⁺); melting point: 161-164° C.

4-(2,5-Dimethylphenylthio)-3-(4-isopropylpiperazin-1-ylsulfonyl)benzonitrile 67. HPLC purity: 100%; ¹H NMR (500 MHz, DMSO-d₆): δ 8.20 (d, J=2 Hz, 1H), 7.85 (dd, J₁=2 Hz, J₂=8 Hz, 1H), 7.40 (m, 2H), 7.33 (m, 1H), 6.70 (d, J=8 Hz, 1H), 3.24 (s, 4H), 2.68 (m, 1H), 2.31 (s, 3H), 2.23 (s, 3H), 0.94 (d, J=7 Hz, 6H); MS (ESI, EI⁺): m/z=430 (MH⁺); melting point: 148-151° C.

4-(2,5-Dimethylphenylthio)-3-(4-isopropylpiperazin-1-ylsulfonyl)benzonitrile, hydrochloride 67. HPLC purity: 100%; ¹H NMR (500 MHz, DMSO-d₆): δ 10.92 (s, 1H), 8.28 (d, J=2 Hz, 1H), 7.90 (dd, J₁=2 Hz, J₂=8 Hz, 1H), 7.47 (s, 1H), 7.41 (d, J=8 Hz, 1H), 7.34 (d, J=8 Hz, 1H), 6.74 (d, J=8 Hz, 1H), 3.99 (m, 2H), 3.50 (m, 2H), 3.38 (m, 2H), 3.11 (m, 2H), 2.32 (s, 3H), 2.25 (s, 3H), 1.27 (d, J=7 Hz, 6H); MS (ESI, EI⁺): m/z=430 (MH⁺).

4-(2,5-Dimethylphenylthio)-3-(4-(pentan-3-yl)piperazin-1-ylsulfonyl)benzonitrile 68. HPLC purity: 100%; ¹H NMR (500 MHz, DMSO-d₆): δ 8.20 (s, 1H), 7.85 (d, J=8 Hz, 1H), 7.40 (m, 2H), 7.33 (d, J=7 Hz, 1H), 6.71 (d, J=9 Hz, 1H), 3.23 (m, 4H), 2.54 (m, 3H), 2.46 (m, 2H), 2.31 (s, 3H), 2.23 (s, 3H), 1.40 (m, 1H), 1.26 (m, 2H), 1.22 (m, 1H), 0.86 (m, 6H); MS (ESI, EI⁺): m/z=458 (MH⁺); melting point: 94-99° C.

4-(2,5-Dimethylphenylthio)-3-(4-(pentan-3-yl)piperazin-1-ylsulfonyl)benzonitrile, hydrochloride 68. HPLC purity: 100%; ¹H NMR (500 MHz, DMSO-d₆): δ 10.77 (s, 1H), 8.28 (s, 1H), 7.90 (d, J=8 Hz, 1H), 7.47 (s, 1H), 7.41 (d, J=8 Hz, 1H), 7.35 (d, J=8 Hz, 1H), 6.75 (d, J=8 Hz, 1H), 4.00 (m, 2H), 3.45 (m, 5H), 3.15 (m, 2H), 2.31 (s, 3H), 2.25 (s, 3H), 1.80 (m, 1H), 1.38 (m, 2H), 1.24 (d, J=8 Hz, 4H), 0.90 (t, J₁=J₂=8 Hz, 3H); MS (ESI, EI⁺): m/z=458 (MH⁺); melting point: 200-202° C.

3-(4-Cyclopentylpiperazin-1-ylsulfonyl)-4-(2,5-dimethylphenylthio)-benzonitrile 69. HPLC purity: 99%; ¹H NMR (500 MHz, DMSO-d₆): δ 8.19 (d, J=2 Hz, 1H), 7.85 (dd, J₁=2 Hz, J₂=8 Hz, 1H), 7.43 (s, 1H), 7.39 (d, J=8 Hz, 1H), 7.33 (d, J=8 Hz, 1H), 6.70 (d, J=8 Hz, 1H), 3.25 (s, 4H), 2.48 (s, 4H), 2.31 (s, 3H), 2.23 (s, 3H), 1.73 (m, 2H), 1.56 (m, 2H), 1.48 (m, 2H), 1.29 (2H); MS (ESI, m/z=456 (MH⁺); melting point: 168-170° C.

3-(4-Cyclopentylpiperazin-1-ylsulfonyl)-4-(2,5-dimethylphenylthio)-benzonitrile, hydrochloride 69. HPLC purity: 99%; ¹H NMR (500 MHz, DMSO-d₆): δ 11.25 (s, 1H), 8.27 (d, J=2 Hz, 1H), 7.90 (dd, J₁=2 Hz, J₂=8 Hz, 1H), 7.48 (s, 1H), 7.41 (d, J=8 Hz, 1H), 7.35 (d, J=8 Hz, 1H), 6.74 (d, J=8 Hz, 1H), 3.97 (m, 2H), 3.53 (m, 3H), 3.37 (m, 2H), 3.11 (m, 2H), 2.32 (s, 3H), 2.24 (s, 3H), 1.99 (m, 2H), 1.74 (m, 4H), 1.54 (m, 2H); MS (ESI, EI⁺): m/z=456 (MH⁺).

4-(2,5-Dimethylphenylthio)-3-(4-methyl-1,4-diazepan-1-ylsulfonyl)benzonitrile 70. HPLC purity: 100%; ¹H NMR (500 MHz, DMSO-d₆): δ 8.23 (s, 1H), 7.82 (d, J=7 Hz, 1H), 7.43 (s, 1H), 7.39 (d, J=8 Hz, 1H), 7.33 (d, J=8 Hz, 1H), 6.72 (d, J=9 Hz, 1H), 3.53 (m, 2H), 3.48 (t, J₁=J₂=6 Hz, 2H), 2.58 (m, 4H), 2.32 (s, 3H), 2.28 (s, 3H), 2.21 (s, 3H), 1.84 (m, 2H); MS (ESI, EI⁺): m/z=416 (MH⁺).

4-(2,5-Dimethylphenylthio)-3-(morpholinosulfonyl)benzonitrile 71. HPLC purity: 100%; ¹H NMR (500 MHz, DMSO-d₆): δ 8.21 (s, 1H), 7.86 (d, J=9 Hz, 1H), 7.45 (s, 1H), 7.40 (d, J=8 Hz, 1H), 7.34 (d, J=8 Hz, 1H), 6.71 (d, J=8 Hz, 1H), 3.66 (m, 4H), 3.25 (m, 4H), 2.32 (s, 3H), 2.24 (s, 3H); MS (ESI, EI⁺): m/z=343 (MH⁺); melting point: 206-209° C.

5-Cyano-N-(2-(diethylamino)ethyl)-2-(2,5-dimethylphenylthio)-benzenesulfonamide, hydrochloride 73. HPLC purity: 97.3%; ¹H NMR (500 MHz, DMSO-d₆): δ 10.29 (s, 1H), 8.55 (t, J₁=J₂=6 Hz, 1H), 8.24 (d, J=2 Hz, 1H), 7.86 (dd, J₁=2 Hz, J₂=8 Hz, 1H), 7.47 (s, 1H), 7.39 (d, J=8 Hz, 1H), 7.33 (d, J=8 Hz, 1H), 6.76 (d, J=8 Hz, 1H), 3.31 (m, 2H), 3.16 (m, 6H), 2.33 (s, 3H), 2.22 (s, 3H), 1.21 (t, J₁=J₂=7 Hz, 6H); MS (ESI, EI⁺): m/z=418 (MH⁺); melting point: 181-184° C.

4-(2,5-Dimethylphenylthio)-3-(4-(pyrrolidin-1-yl)piperidin-1-ylsulfonyl)-benzonitrile 74. HPLC purity: 98.4%; ¹H NMR (500 MHz, DMSO-d₆): δ 8.21 (d, J=2 Hz, 1H), 7.84 (dd, J₁=2 Hz, J₂=8 Hz, 1H), 7.42 (s, 1H), 7.40 (d, J=8 Hz, 1H), 7.33 (d, J=8 Hz, 1H), 6.71 (d, J=8 Hz, 1H), 3.68 (m, 2H), 2.95 (m, 2H), 2.45 (s, 4H), 2.31 (s, 3H), 2.21 (s, 3H), 2.15 (m, 1H), 1.88 (m, 2H), 1.65 (s, 4H), 1.47 (m, 2H); MS (ESI, EI⁺): m/z=457 (MH⁺); melting point: 179-181° C.

4-(2,5-Dimethylphenylthio)-3-(4-(pyrrolidin-1-yl)piperidin-1-ylsulfonyl)-benzonitrile, hydrochloride 74. HPLC purity: 98.1%; ¹H NMR (500 MHz, DMSO-d₆): δ 10.98 (s, 1H), 8.24 (d, J=2 Hz, 1H), 7.86 (dd, J₁=2 Hz, J₂=8 Hz, 1H), 7.49 (s, 1H), 7.40 (d, J=8 Hz, 1H), 7.34 (d, J=8 Hz, 1H), 6.71 (d, J=8 Hz, 1H), 3.94 (m, 2H), 3.47 (m, 2H), 3.24 (m, 1H), 3.00 (m, 2H), 2.83 (t, J₁=J₂=12 Hz, 2H), 2.32 (s, 3H), 2.23 (s, 3H), 2.15 (m, 2H), 1.96 (m, 2H), 1.85 (m, 2H), 1.76 (m, 2H); MS (ESI, EI⁺): m/z=456 (MH⁺).

4-(2,5-Dimethylphenylthio)-3-(thiomorpholinosulfonyl)benzonitrile 85. HPLC purity: 100%; ¹H NMR (500 MHz, DMSO-d₆): δ 8.24 (d, J=1 Hz, 1H), 7.85 (dd, J₁=7 Hz, J₂=1 Hz, 1H), 7.44 (s, 1H), 7.40 (d, J=8 Hz, 1H), 7.34 (d, J=8 Hz, 1H), 6.72 (d, J=8 Hz, 1H), 3.58 (m, 4H), 2.70 (m, 4H), 2.32 (s, 3H), 2.22 (s, 3H); MS (ESI, EI⁺): m/z=343 (MH⁺); melting point: 196-199° C.

Compound 86. HPLC purity: 97.8%; ¹H NMR (500 MHz, DMSO-d₆): δ 8.31 (d, J=1 Hz, 1H), 7.88 (dd, J₁=7 Hz, J₂=1 Hz, 1H), 7.45 (s, 1H), 7.40 (d, J=8 Hz, 1H), 7.34 (d, J=8 Hz, 1H), 6.74 (d, J=8 Hz, 1H), 3.83 (m, 4H), 3.31 (m, 4H), 2.32 (s, 3H), 2.22 (s, 3H); MS (ESI, EI⁺): m/z=500 (MH⁺); melting point: 169-173° C.

Example 3

Preparation of 4-(2,5-dichlorophenylthio)-3-(4-(dimethylamino)piperidin-1-ylsulfonyl)benzonitrile

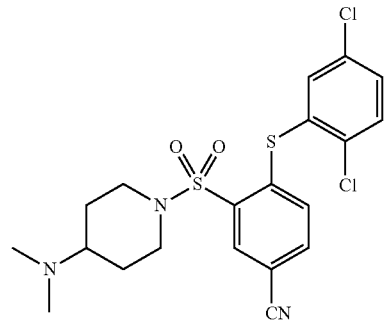

Compound 83 was synthesized as shown in Scheme 5.

Scheme 5

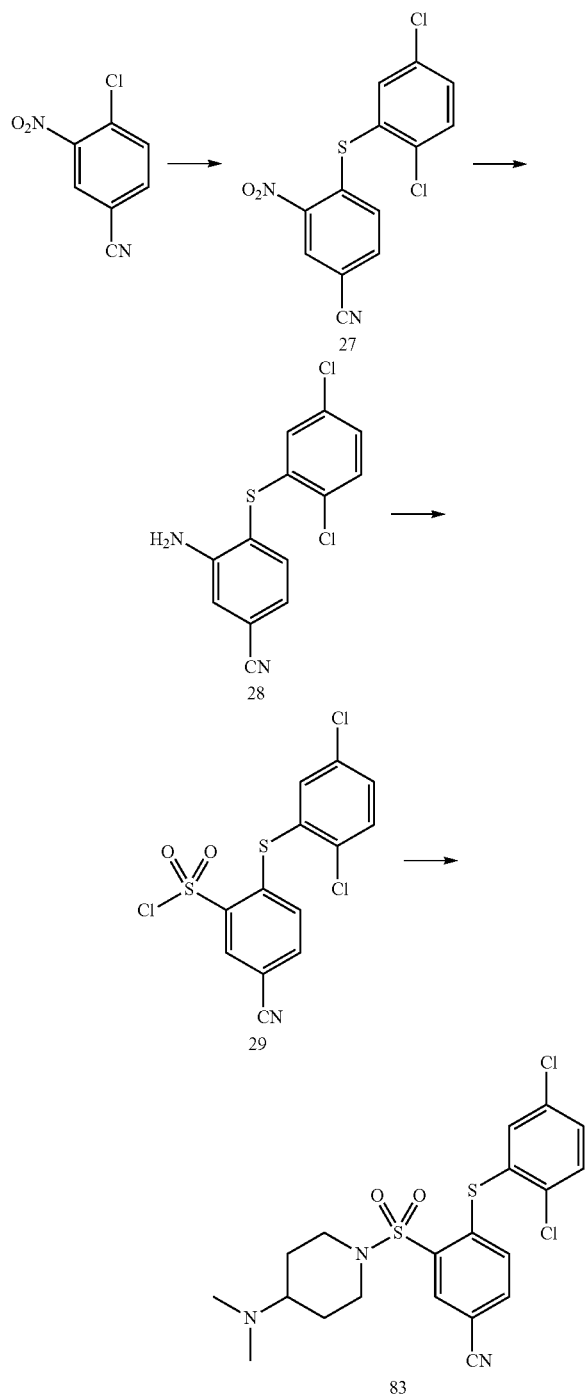

4-(2,5-Dichlorophenylthio)-3-nitrobenzonitrile 27. To a solution of 4-chloro-3-nitrobenzonitrile (10.0 g, 54.77 mmol) in THF (300 mL) was added 2,5-dichlorobenzenethiol (19.6 g, 12.108 mmol) and $K_2CO_3$ (37.8 g, 273.85 mmol). The reaction mixture was refluxed for 48 hrs. The solid was filtered and washed with copious amounts of EtOAc. The filtrate was washed sequentially with saturated $NaHCO_3$, $H_2O$, and saturated NaCl solution, dried over $MgSO_4$, filtered, and evaporated in vacuo. The resulting solid was then triturated with DCM and hexanes, and filtered to yield compound 27 as a yellow solid (11.823 g, 91.0% HPLC purity, 66.4% yield). $^1$H NMR (500 MHz, DMSO-$d_6$): δ 8.82 (d, J=2 Hz, 1H), 8.00 (m, 3H), 7.80 (d, J=9 Hz, 1H), 7.75 (dd, $J_1$=3 Hz, $J_2$=9 Hz, 1H), 6.97 (d, J=9 Hz, 2H).

3-Amino-4-(2,5-dichlorophenylthio)benzonitrile 28. A solution of compound 27 (11.8 g, 36.36 mmol) in THF (200 mL) was combined with a solution of sodium hydrosulfite (37.98 g, 218.16 mmol) in water (50 mL). The combined solution was stirred vigorously overnight at 45° C. The reaction was monitored by TLC (25% EtOAc in hexanes), and was complete after 16 hrs as indicated by absence of the starting material. The reaction was removed from heat and THF was evaporated. Aqueous solution was filtered to yield a white solid. The solid was washed with water and dried in a vacuum oven overnight to yield compound 28 (9.077 g, 97% HPLC purity, 84.6% yield). $^1$H NMR (500 MHz, DMSO-$d_6$): δ 7.55 (d, J=8 Hz, 1H), 7.48 (d, J=8 Hz, 1H), 7.28 (dd, $J_1$=2 Hz, $J_2$=7 Hz, 1H), 7.19 (d, J=2 Hz, 1H), 6.99 (dd, $J_1$=2 Hz, $J_2$=8 Hz, 1H), 6.50 (d, J=2 Hz, 1H), 6.04 (s, 2H).

5-Cyano-2-(2,5-dichlorophenylthio)benzene-1-sulfonyl chloride 29. A solution of compound 28 (6.00 g, 20.34 mmol) in acetic acid (100 mL) was added HCl (12 M, 40.00 mL). The solution was stirred at 85° C. for 20 min. The solution was then cooled to room temperature. A solution of $NaNO_2$ (2.807 g, 40.68 mmol) in water (5 mL) was added dropwise to the compound 28 containing solution stirred in an ice bath. After addition, the solution was stirred in an ice bath for additional 2 hrs. In a separate flask, $SO_2$ was bubbled through acetic acid (100 mL) for 45 min at room temperature to form a $SO_2$ saturated solution. $CuCl_2$ (1.007 g, 10.17 mmol) was then added to the $SO_2$ saturated solution and stirred for additional 15 min to form a $CuCl_2$ solution. The $CuCl_2$ solution was then cooled with an ice bath and stirred for 10 min. The compound 28 containing solution was then added dropwise into the $CuCl_2$ solution. After the addition, the solution was stirred for additional 45 min, and was then poured onto ice water and stirred for 1 hr. The resulting precipitate was then filtered to yield compound 29 as an orange solid (1.3 g, 80% HPLC purity, 17% yield).

4-(2,5-Dichlorophenylthio)-3-(4-(dimethylamino)piperidin-1-ylsulfonyl)benzonitrile 83. To a solution of compound 29 (0.100 g, 0.26 mmol) in DCM (8.00 mL) was added 4-dimethylaminopiperidine (0.044 g, 0.34 mmol) and TEA (0.034 g, 0.34 mmol). The reaction was monitored with TLC (25% EtOAc in hexanes, $R_f$=0.0). After stirring at room temperature for 2 hrs, the reaction was complete as indicated by the absence of the starting material (TLC). Water was added and aqueous layer was extracted twice with DCM. Combined extracts were washed sequentially with water and brine, dried over $MgSO_4$, filtered, and evaporated in vacuo to form a clear oil. The oil was dissolved in DCM and purified with chromatography with a gradient from 0 to 30% MeOH in DCM. Pure fractions were combined, evaporated in vacuo, triturated with DCM and hexanes, and then filtered to yield compound 83 as a white powder (0.068 g, 100% HPLC purity, 56% yield). $^1$H NMR (500 MHz, DMSO-$d_6$): δ 8.26 (d, J=2 Hz, 1H), 7.89 (m, 2H), 7.78 (d, J=9 Hz, $^1$H), 7.71 (dd, $J_1$=3 Hz, $J_2$=9 Hz, 1H), 6.93 (d, J=8 Hz, 1H), 3.79 (d, J=12 Hz, 2H), 2.85 (t, J=13 Hz, 2H), 2.22 (m, 1H), 2.12 (s, 6H), 1.79 (m, 2H), 1.40 (m, 2H); MS (ESI, EI$^+$): m/z=470 (MH$^+$); melting point: 140-143° C.

4-(2,5-Dichlorophenylthio)-3-(4-(dimethylamino)piperidin-1-ylsulfonyl)benzonitrile, hydrochloride 83. To a solution of neutral compound 83 (15.0 mg, 0.03 mmol) in 1,4-dioxane (2.0 mL) was added 4 N HCl in 1,4-dioxane (30.0 μL, 0.12 mmol). The reaction mixture was stirred for 10 min at room temperature before adding 2 mL of diethyl ether. A white precipitate was formed and collected via filtration to obtain compound 83 hydrochloride as a white solid as product (15.0 mg, 100% HPLC purity, 99% yield). HPLC purity:

100%; $^1$H NMR (500 MHz, DMSO-d$_6$): δ 10.64 (s, 1H), 8.29 (d, J=2 Hz, 1H), 7.94 (d, J=2 Hz, 1H), 7.91 (dd, J$_1$=2 Hz, J$_2$=8 Hz, 1H), 7.79 (d, J=8 Hz, 1H), 7.72 (dd, J$_1$=2 Hz, J$_2$=8 Hz, 1H), 6.93 (d, J=8 Hz, 1H), 3.97 (d, J=12 Hz, 2H), 3.29 (m, 1H), 2.84 (t, J$_1$=J$_2$=12 Hz, 2H), 2.68 (d, J=8 Hz, 6H), 2.12 (d, J=12 Hz, 2H), 1.69 (m, 2H); MS (ESI, EI$^+$): m/z=470 (MH$^+$); melting point: 267-269° C.

The following compounds were made according to the procedures as described in this example.

4-(2,5-Dichlorophenylthio)-3-(piperazin-1-yl sulfonyl) benzonitrile 76. HPLC purity: 100%; $^1$H NMR (500 MHz, DMSO-d$_6$): δ 8.24 (d, J=2 Hz, 1H), 7.89 (m, 2H), 7.79 (d, J=8 Hz, 1H), 7.72 (dd, J$_1$=2 Hz, J$_2$=8 Hz, 1H), 6.91 (d, J=8 Hz, 1H), 3.15 (m, 4H), 2.73 (m, 4H); MS (ESI, EI$^+$): m/z=429 (MH$^+$); melting point: 190-194° C.

4-(2,5-Dichlorophenylthio)-3-(piperazin-1-ylsulfonyl) benzonitrile, dihydrochloride 76. HPLC purity: 100%; $^1$H NMR (500 MHz, DMSO-d$_6$): δ 9.30 (s, 2H), 8.32 (d, J=2 Hz, 1H), 7.95 (m, 2H), 7.80 (d, J=8 Hz, 1H), 7.73 (dd, J$_1$=2 Hz, J$_2$=8 Hz, 1H), 6.94 (d, J=8 Hz, 1H), 3.54 (m, 4H), 3.19 (m, 4H); MS (ESI, EI$^+$): m/z=428 (MH$^+$); melting point: 156-162° C.

4-(2,5-Dichlorophenylthio)-3-(4-isopropylpiperazin-1-ylsulfonyl)benzonitrile 77. HPLC purity: 100%; $^1$H NMR (500 MHz, DMSO-d$_6$): δ 8.25 (d, J=2 Hz, 1H), 7.91 (dd, J$_1$=2 Hz, J$_2$=8 Hz, 2H), 7.78 (d, J=8 Hz, 1H), 7.71 (dd, J$_1$=2 Hz, J$_2$=8 Hz, 1H), 6.94 (d, J=8 Hz, 1H), 3.24 (m, 4H), 2.67 (m, 1H), 2.48 (m, 4H), 0.92 (d, J=7 Hz, 6H); MS (ESI, EI$^+$): m/z=472 (MH$^+$); melting point: 163-166° C.

4-(2,5-Dichlorophenylthio)-3-(4-isopropylpiperazin-1-ylsulfonyl)benzonitrile, hydrochloride 77. HPLC purity: 100%; $^1$H NMR (500 MHz, DMSO-d$_6$): δ 10.77 (s, 1H), 8.34 (d, J=2 Hz, 1H), 7.95 (m, 2H), 7.80 (d, J=8 Hz, 1H), 7.73 (dd, J$_1$=2 Hz, J$_2$=8 Hz, 1H), 6.96 (d, J=8 Hz, 1H), 3.99 (d, J=12 Hz, 2H), 3.49 (m, 3H), 3.34 (m, 2H), 3.11 (m, 2H), 1.25 (d, J=8 Hz, 6H); MS (ESI, EI$^+$): m/z=470 (MH$^+$); melting point: 259-285° C.

4-(2,5-Dichlorophenylthio)-3-(4-(pentan-3-yl)piperazin-1-ylsulfonyl)-benzonitrile 78. HPLC purity: 100%; $^1$H NMR (500 MHz, DMSO-d$_6$): δ 8.26 (d, J=2 Hz, 1H), 7.90 (dd, J$_1$=2 Hz, J$_2$=8 Hz, 1H), 7.89 (d, J=2 Hz, 1H), 7.79 (d, J=8 Hz, 1H), 7.71 (dd, J$_1$=2 Hz, J$_2$=8 Hz, 1H), 6.95 (d, J=8 Hz, 1H), 3.23 (m, 4H), 2.51 (m, 4H), 2.15 (m, 1H), 1.36 (m, 2H), 1.21 (m, 2H), 0.81 (t, J$_1$=J$_2$=7 Hz, 6H); melting point: 127-130° C.

4-(2,5-Dichlorophenylthio)-3-(4-(pentan-3-yl)piperazin-1-ylsulfonyl)-benzonitrile, hydrochloride 78. HPLC purity: 100%; $^1$H NMR (500 MHz, DMSO-d$_6$): δ 10.62 (s, 1H), 8.33 (d, J=2 Hz, 1H), 7.95 (m, 2H), 7.80 (d, J=8 Hz, 1H), 7.73 (dd, J$_1$=2 Hz, J$_2$=8 Hz, 1H), 7.96 (d, J=8 Hz, 1H), 3.95 (d, J=13 Hz, 2H), 3.48 (m, 4H), 3.07-3.18 (m, 3H), 1.81 (m, 1H), 1.60 (m, 2H), 0.85 (t, J$_1$=J$_2$=7 Hz, 6H); melting point: 239-248° C.

4-(2,5-Dichlorophenylthio)-3-(3,5-dimethylpiperazin-1-ylsulfonyl)benzonitrile 79. HPLC purity: 97.2%; $^1$H NMR (500 MHz, DMSO-d$_6$): δ 8.25 (d, J=2 Hz, 1H), 7.90 (d, J=2 Hz, 1H), 7.89 (d, J=2 Hz, 1H), 7.79 (d, J=8 Hz, 1H), 7.72 (dd, J$_1$=2 Hz, J$_2$=8 Hz, 1H), 6.90 (d, J=7 Hz, 1H), 3.65 (m, 2H), 2.72 (m, 2H), 2.20 (t, J$_1$=J$_2$=11 Hz, 3H); melting point: 176-180° C.

4-(2,5-Dichlorophenylthio)-3-(3,5-dimethylpiperazin-1-ylsulfonyl)benzonitrile, dihydrochloride 79. HPLC purity: 100%; $^1$H NMR (500 MHz, DMSO-d$_6$): δ 9.48 (s, 1H), 9.10 (s, 1H), 8.32 (d, J=2 Hz, 1H), 7.96 (m, 2H), 7.93 (d, J$_1$=2 Hz, J$_2$=8 Hz, 1H), 7.80 (d, J=8 Hz, 1H), 7.74 (dd, J$_1$=2 Hz, J$_2$=8 Hz, 1H), 6.93 (d, J=8 Hz, 1H), 3.99 (d, J=13 Hz, 2H), 3.37 (m, 2H), 2.89 (t, J=12 Hz, 2H), 1.25 (d, J=7 Hz, 6H); MS (ESI, EI$^+$): m/z=456 (MH$^+$); melting point: 160-190° C.

3-(4-Cyclopentylpiperazin-1-ylsulfonyl)-4-(2,5-dichlorophenylthio)-benzonitrile 80. HPLC purity: 99.6%; $^1$H NMR (500 MHz, DMSO-d$_6$): δ 8.24 (d, J=2 Hz, 1H), 7.90 (m, 2H), 7.78 (d, J=8 Hz, 1H), 7.70 (dd, J$_1$=2 Hz, J$_2$=8 Hz, 1H), 6.92 (d, J=8 Hz, 1H), 3.25 (m, 4H), 2.47 (m, 4H), 1.72 (m, 2H), 1.56 (m, 2H), 1.47 (m, 2H), 1.27 (m, 2H); MS (ESI, EI$^+$): m/z=496 (MH$^+$); melting point: 198-200° C.

3-(4-Cyclopentylpiperazin-1-ylsulfonyl)-4-(2,5-dichlorophenylthio)-benzonitrile, hydrochloride 80. HPLC purity: 100%; $^1$H NMR (500 MHz, DMSO-d$_6$): 11.25 (s, 1H), 8.33 (d, J=2 Hz, 1H), 7.97 (d, J=2 Hz, 1H), 7.95 (dd, J$_1$=2 Hz, J$_2$=8 Hz, 1H), 7.79 (d, J=8 Hz, 1H), 7.73 (dd, J$_1$=2 Hz, J$_2$=8 Hz, 1H), 6.95 (d, J=8 Hz, 1H), 3.97 (d, J=13 Hz, 2H), 3.57 (m, 2H), 4.51 (m, 1H), 3.35 (m, 2H), 3.09 (m, 2H), 1.97 (m, 2H), 1.69-1.78 (m, 4H), 1.53 (m, 2H); MS (ESI, EI$^+$): m/z=496 (MH$^+$); melting point: 260-285° C.

3-(4-Cyclopentylpiperazin-1-ylsulfonyl)-4-(2,5-dichlorophenylthio)-benzonitrile, sulfuric acid 80. HPLC purity: 99%; $^1$H NMR (500 MHz, DMSO-d$_6$): δ 9.48 (s, 1H), 8.34 (d, J=2 Hz, 1H), 7.95 (m, 2H), 7.81 (d, J=8 Hz, 1H), 7.74 (dd, J$_1$=2 Hz, J$_2$=8 Hz, 1H), 6.96 (d, J=8 Hz, 1H), 4.00 (m, 2H), 3.59 (m, 4H), 3.13 (m, 4H), 2.00 (m, 2H), 1.53-1.72 (m, 6H); melting point: 230-240° C.

3-(4-Cyclopentylpiperazin-1-yl sulfonyl)-4-(2,5-dichlorophenylthio)-benzonitrile, ethanesulfonic acid 80. HPLC purity: 100%; $^1$H NMR (500 MHz, DMSO-d$_6$): δ 9.65 (s, 1H), 8.34 (d, J=2 Hz, 1H), 7.95 (d, J=8 Hz, 2H), 7.81 (d, J=8 Hz, 1H), 7.74 (dd, J$_1$=2 Hz, J$_2$=8 Hz, 1H), 6.95 (d, J=8 Hz, 1H), 4.00 (m, 2H), 3.57 (m, 3H), 3.14 (m, 4H), 2.40 (dd, J$_1$=J$_2$=7 Hz, 3H), 1.99 (m, 2H), 1.67 (m, 3H), 1.54 (m, 2H), 1.04 (t, J$_1$=J$_2$=7 Hz, 3H); melting point: 63-65° C.

3-(4-Cyclopentylpiperazin-1-ylsulfonyl)-4-(2,5-dichlorophenylthio)-benzonitrile, nitric acid 80. HPLC purity: 97.8%; $^1$H NMR (500 MHz, DMSO-d$_6$): δ 9.44 (s, 1H), 8.34 (d, J=2 Hz, 1H), 7.95 (m, 2H), 7.81 (d, J=8 Hz, 1H), 7.74 (dd, J$_1$=2 Hz, J$_2$=8 Hz, 1H), 6.97 (d, J=8 Hz, 1H), 4.01 (d, J=10 Hz, 2H), 3.60 (d, J=10 Hz, 2H), 3.05-3.17 (m, 4H), 2.00 (m, 2H), 1.54-1.69 (m, 7H); melting point: 170-190° C.

3-(4-Cyclopentylpiperazin-1-ylsulfonyl)-4-(2,5-dichlorophenylthio)-benzonitrile, oxalic acid 80. HPLC purity: 98%; $^1$H NMR (500 MHz, DMSO-d$_6$): δ 8.29 (s, 1H), 7.93 (m, 2H), 7.79 (d, J=8 Hz, 1H), 7.72 (dd, J$_1$=2 Hz, J$_2$=8 Hz, 1H), 6.94 (d, J=8 Hz, 1H), 3.42 (s, 4H), 3.01 (m, 1H), 2.91 (s, 4H), 1.85 (m, 2H), 1.62 (m, 2H), 1.50 (m, 4H).

4-(2,5-Dichlorophenylthio)-3-(4-methyl-1,4-diazepan-1-ylsulfonyl)-benzonitrile 81. HPLC purity: 100%; $^1$H NMR (500 MHz, DMSO-d$_6$): δ 8.28 (d, J=2 Hz, 1H), 7.88 (m, 2H), 7.76 (d, J=8 Hz, 1H), 7.70 (dd, J$_1$=2 Hz, J$_2$=8 Hz, 1H), 6.95 (d, J=8 Hz, 1H), 3.54 (m, 2H), 3.48 (t, J$_1$=J$_2$=6 Hz, 2H), 2.58 (m, 2H), 2.54 (m, 2H), 2.26 (s, 3H), 1.81 (m, 2H); MS (ESI, EI$^+$): m/z=456 (MH$^+$); melting point: 101-104° C.

4-(2,5-Dichlorophenylthio)-3-(4-methyl-1,4-diazepan-1-ylsulfonyl)-benzonitrile, hydrochloride 81. HPLC purity: 100%; $^1$H NMR (500 MHz, DMSO-d$_6$): δ 10.68 (s, 1H), 8.31 (d, J=2 Hz, 1H), 7.91 (m, 2H), 7.78 (d, J=8 Hz, 1H), 7.71 (dd, J$_1$=2 Hz, J$_2$=8 Hz, 1H), 6.97 (d, J=8 Hz, 1H), 4.01 (m, 1H), 3.67 (m, 1H), 3.48-3.59 (m, 4H), 3.23 (m, 2H), 2.81 (s, 3H), 2.16 (m, 2H); MS (ESI, EI$^+$): m/z=456 (MH$^+$); melting point: 241-255° C.

4-(2,5-Dichlorophenylthio)-3-(morpholinosulfonyl)benzonitrile 82. HPLC purity: 96%; $^1$H NMR (500 MHz, DMSO-d$_6$): δ 8.26 (d, J=2 Hz, 1H), 7.96 (d, J=2 Hz, 1H), 7.91 (dd, J$_1$=2 Hz, J$_2$=8 Hz, 1H), 7.79 (d, J=8 Hz, 1H), 7.72 (dd, J$_1$=2 Hz, J$_2$=8 Hz, 1H), 6.93 (d, J=8 Hz, 1H), 3.65 (m, 4H), 3.26 (m, 4H); melting point: 216-219° C.

4-(2,5-Dichlorophenylthio)-3-(4-(pyrrolidin-1-yl)piperidin-1-ylsulfonyl)benzonitrile 84. HPLC purity: 100%; $^1$H NMR (500 MHz, DMSO-d$_6$): δ 8.26 (d, J=2 Hz, 1H), 7.89 (m, 2H), 7.79 (d, J=8 Hz, 1H), 7.70 (dd, J$_1$=2 Hz, J$_2$=8 Hz, 1H), 6.92 (d, J=8 Hz, 1H), 3.67 (m, 2H), 2.96 (m, 2H), 2.43 (m, 4H), 2.12 (m, 1H), 1.85 (m, 2H), 1.64 (m, 4H), 1.47 (m, 2H); MS (ESI, EI$^+$): m/z=496 (MH$^+$); melting point: 177-180° C.

4-(2,5-Dichlorophenylthio)-3-(4-(pyrrolidin-1-yl)piperidin-1-ylsulfonyl)benzonitrile, hydrochloride 84. HPLC purity: 100%; $^1$H NMR (500 MHz, DMSO-d$_6$): 10.88 (s, 1H), 8.29 (d, J=2 Hz, 1H), 7.97 (d, J=2 Hz, 1H), 7.91 (dd, J$_1$=2 Hz, J$_2$=8 Hz, 1H), 7.79 (d, J=8 Hz, 1H), 7.71 (dd, J$_1$=2 Hz, J$_2$=8 Hz, 1H), 6.93 (d, J=8 Hz, 1H), 3.94 (d, J=13 Hz, 2H), 3.45 (m, 2H), 3.23 (m, 1H), 3.00 (m, 2H), 2.82 (t, J$_1$=J$_2$=12 Hz, 2H), 2.14 (d, J=12 Hz, 2H), 1.93 (m, 2H), 1.85 (m, 2H), 1.74 (m, 2H); MS (ESI, EI⁺): m/z=496 (MH⁺); melting point: 285-300° C.

Methyl 4-(5-cyano-2-(2,5-dichlorophenylthio)phenylsulfonyl)piperazine-2-carboxylate 138. HPLC purity: 99.3%; $^1$H NMR (500 MHz, CDCl$_3$) δ 8.23 (d, J=2 Hz, 1H), 7.70 (d, J=2 Hz, 1H), 7.55 (dd, J$_1$=8 Hz, J$_2$=2 Hz, 1H), 7.54 (d, J=9 Hz, 1H), 7.47 (dd, J$_1$=9 Hz, J$_2$=2 Hz, 1H), 6.83 (d, J=8 Hz, 1H), 4.04 (m, 2H), 3.73 (m, 1H), 3.61 (m, 3H), 3.18 (m, 1H), 1.13 (d, J=6 Hz, 3H); MS (ESI, EI⁺): m/z=486 (MH⁺); melting point: 124-136° C.

Example 4

Preparation of 4-(2,5-dimethylphenoxy)-3-(piperazin-1-ylsulfonyl)benzonitrile

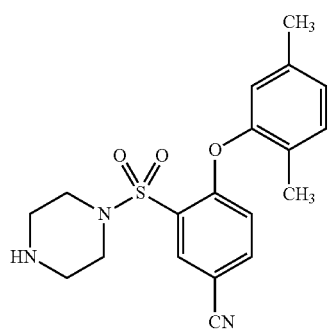

51

Compound 51 was synthesized as shown in Scheme 6.

4-(2,5-Dimethylphenoxy)-3-nitrobenzonitrile 30. 2,5-Dimethylphenol (6.99 g, 57.20 mmol) and 4-chloro-3-nitrobenzonitrile (8.00 g, 43.96 mmol) were combined with K$_2$CO$_3$ (30.40 g, 220.00 mmol) in THF (100 mL). The reaction mixture was heated to reflux for 48 hrs and then the solid was filtered through a bed of Celite. After rinsing the residue with copious amounts of EtOAc, the filtrate was washed sequentially with NaHCO$_3$, water, and brine, dried over anhydrous MgSO$_4$, and filtrated. The filtrate was concentrated in vacuo to produce compound 30 as a white powder (10.00 g, 85.0% yield, 99.1% pure). $^1$H NMR (500 MHz, DMSO-d$_6$): δ 8.65 (d, J=2 Hz, 1H), 8.03 (dd, J$_1$=9 Hz, J$_2$=2 Hz, 1H), 7.28 (d, J=8 Hz, 1H), 7.09 (d, J=8 Hz, 1H), 6.98 (s, 1H), 6.91 (d, J=9 Hz, 1H), 2.28 (s, 3H), 2.07 (s, 3H).

3-Amino-4-(2,5-dimethylphenoxy)benzonitrile 31. The coupled product 30 (12.00 g, 44.73 mmol) was reduced with sodium hydrosulfite (30.47 g, 175.00 mmol) in a mixture of THF (75 mL), water (100 mL), and dioxane (45 mL). After the reaction is complete, volatile organic solvents were removed in vacuo and the precipitate in the remaining water was collected via vacuum filtration to afford compound 31 as a white solid (9.50 g, 89.0% yield, 99.5% pure). $^1$H NMR (500 MHz, DMSO-d$_6$): δ 7.19 (d, J=8 Hz, 1H), 7.07 (d, J=2 Hz, 1H), 6.94 (d, J=8 Hz, 1H), 6.86 (dd, J$_1$=8 Hz, J$_2$=2 Hz, 1H), 6.74 (s, 1H), 6.45 (d, J=8 Hz, 1H), 5.52 (s, 2H), 2.23 (s, 3H), 2.08 (s, 3H).

Scheme 6

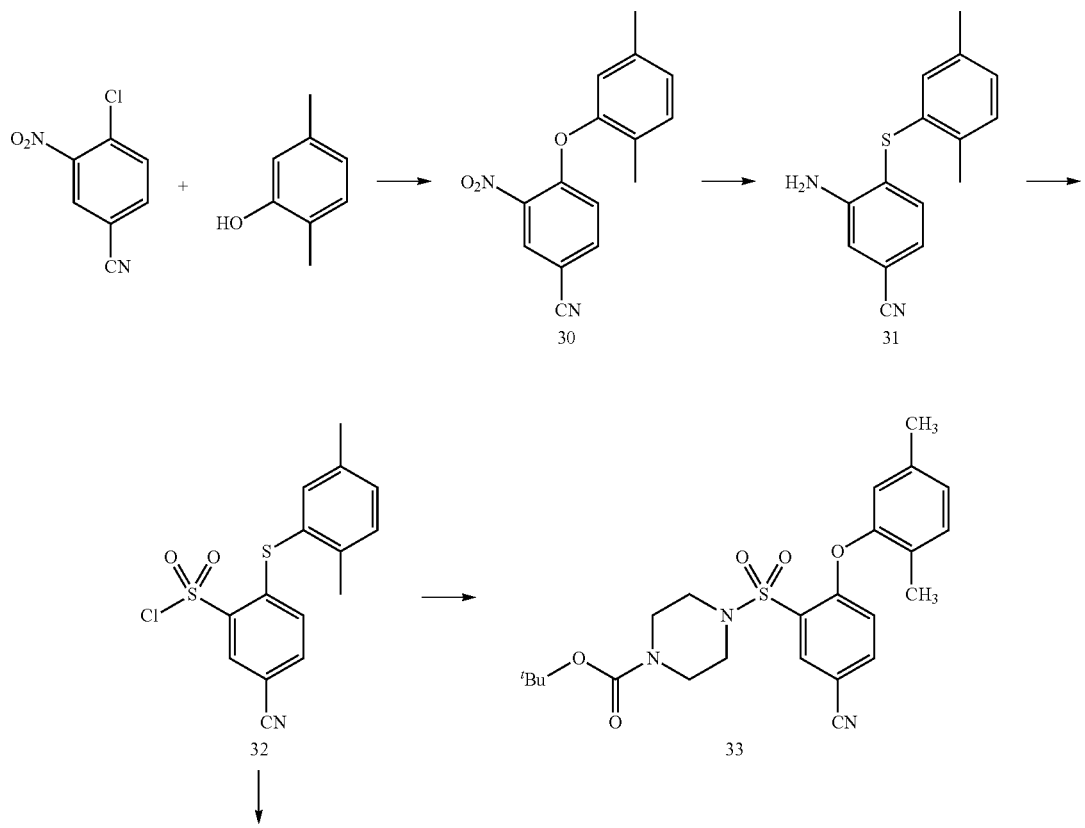

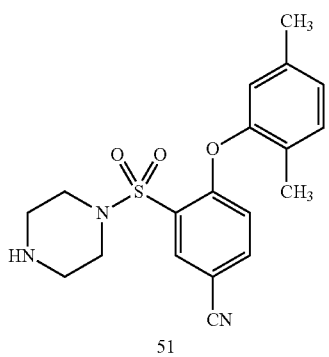

51

5-Cyano-2-(2,5-dimethylphenoxy)benzene-1-sulfonyl chloride 32. For conversion from aniline 31 to sulfonyl chloride 32, the Sandmeyer reaction is utilized. Aniline 31 (9.00 g) was dissolved in acetic acid (100 mL). HCl (80 mL) (12 M) was added. Separately, sodium nitrite (5.33 g, 77.20 mmol) was dissolved in minimal water and slowly infused into the HCl salt solution. The resulting reaction mixture was stirred for 2 hrs in an ice bath.

In another reaction vessel, 100 mL of acetic acid is saturated with $SO_2$ gas. Copper (II) chloride (1.91 g, 19.30 mmol) was added. After the aqua color changes to olive green, the $CuCl_2$ solution was cooled with an ice bath and the sodium nitrite solution was slowly added to the $CuCl_2$ solution. After stirring for another 45 min, the mixture was poured into ice water and stirred for 1 hr. The resulting precipitate was collected via filtration to afford compound 32 as an orange solid (9.50 g, 76.0% yield).

Tert-butyl 4-(5-cyano-2-(2,5-dimethylphenoxy)phenyl-sulfonyl)piperazine-1-carboxylate 33. A solution of sulfonyl chloride 32 (0.160 g, 0.50 mmol), tert-butyl piperazine-1-carboxylate (0.121 g, 0.65 mmol), and TEA (0.066 g, 0.65 mmol) in DCM (5 mL) was stirred overnight at room temperature. The reaction was monitored with TLC (25% EtOAc in hexanes). The reaction mixture was concentrated in vacuo and the residual was redissolved with a minimal amount of DCM and chromatographed on normal-phase silica to produce compound 33 as a white powder (0.099 g, 42.0% yield, 100.0% pure). $^1$H NMR (500 MHz, DMSO-$d_6$): δ 8.24 (d, J=2 Hz, 1H), 8.00 (dd, $J_1$=2 Hz, $J_2$=8 Hz, 1H), 7.29 (d, J=8 Hz, 1H), 7.09 (d, J=8 Hz, 1H), 6.98 (s, 1H), 6.78 (d, J=8 Hz, 1H), 3.39 (m, 4H), 3.22 (m, 4H), 2.29 (s, 3H), 2.07 (s, 3H), 1.37 (s, 9H); MS (ESI, EI$^+$): m/z=372 (MH$^+$).

4-(2,5-Dimethylphenoxy)-3-(piperazin-1-ylsulfonyl)benzonitrile 51. A solution of sulfonyl chloride 32 (1.0 g, 3.1 mmol) in 20 mL dichloromethane was infused into a stirring solution of piperazine (5.9 g, 62.2 mmol) in 20 mL of dichloromethane at a rate of 0.2 mL/min. The reaction mixture was stirred for 16 hrs. The completion of the reaction was confirmed by TLC (25% EtOAc in hexanes). Water was then added and the aqueous layer was extracted twice with dichloromethane. The combined organic layers were washed sequentially with water and brine, dried over anhydrous $MgSO_4$, filtered, and concentrated in vacuo to produce a brown solid. The product was chromatographed on normal-phase silica using a gradient of 0-25% MeOH in dichloromethane. Desired fractions were collected and concentrated to produce compound 51 as a pink solid (0.5 g, 1.3 mmol). HPLC purity: 99%; $^1$H NMR (500 MHz, DMSO-$d_6$): δ 8.22 (d, J=2 Hz, 1H), 7.99 (dd, $J_1$=2 Hz, $J_2$=8 Hz, 1H), 7.29 (d, J=8 Hz, 1H), 7.09 (d, J=8 Hz, 1H), 6.94 (s, 1H), 6.78 (d, J=8 Hz, 1H), 3.13 (m, 4H), 2.70 (m, 4H), 2.30 (s, 3H), 2.08 (s, 3H); MS (ESI, EI$^+$): m/z=372 (MH$^+$); melting point: 60-72° C.

4-(2,5-Dimethylphenoxy)-3-(piperazin-1-ylsulfonyl)benzonitrile, dihydrochloride 51. To a solution of neutral compound 51 (0.1 g 0.27 mmol) in 3 mL of 1,4-dioxane was added 4 N HCl in 1,4-dioxane (0.270 mL). The reaction mixture was stirred at room temperature overnight and diethyl ether (3 mL) was added and stirred for 30 min. Another 2 mL of diethyl ether was added. An oil began to form. The solvents were removed under vacuum. Hexanes (3 mL) were added to the resulting residue and the mixture was sonicated. Ethyl acetate (2-3 drops) was added and precipitate began to form in the oil. The resulting white-yellow powder was collected to yield compound 51 dihydrochloride. HPLC purity: 99.8%; $^1$H NMR (500 MHz, DMSO-$d_6$): δ 9.23 (s, 2H), 8.28 (d, J=2 Hz, 1H), 8.04 (dd, $J_1$=2 Hz, $J_2$=8 Hz, 1H), 7.31 (d, J=8 Hz, 1H), 7.11 (d, J=8 Hz, 1H), 7.06 (s, 1H), 6.78 (d, J=8 Hz, 1H), 3.52 (m, 4H), 3.18 (m, 4H), 2.31 (s, 3H), 2.08 (s, 3H); MS (ESI, EI$^+$): m/z=372 (MH$^+$); melting point: 120-195° C.

Example 5

Preparation of 4-(2,5-dichlorophenoxy)-3-(4-methylpiperidin-1-ylsulfonyl)benzonitrile

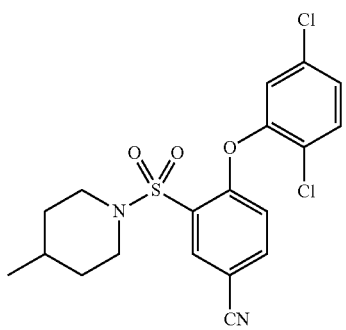

87

Compound 87 was synthesized as shown in Scheme 7.

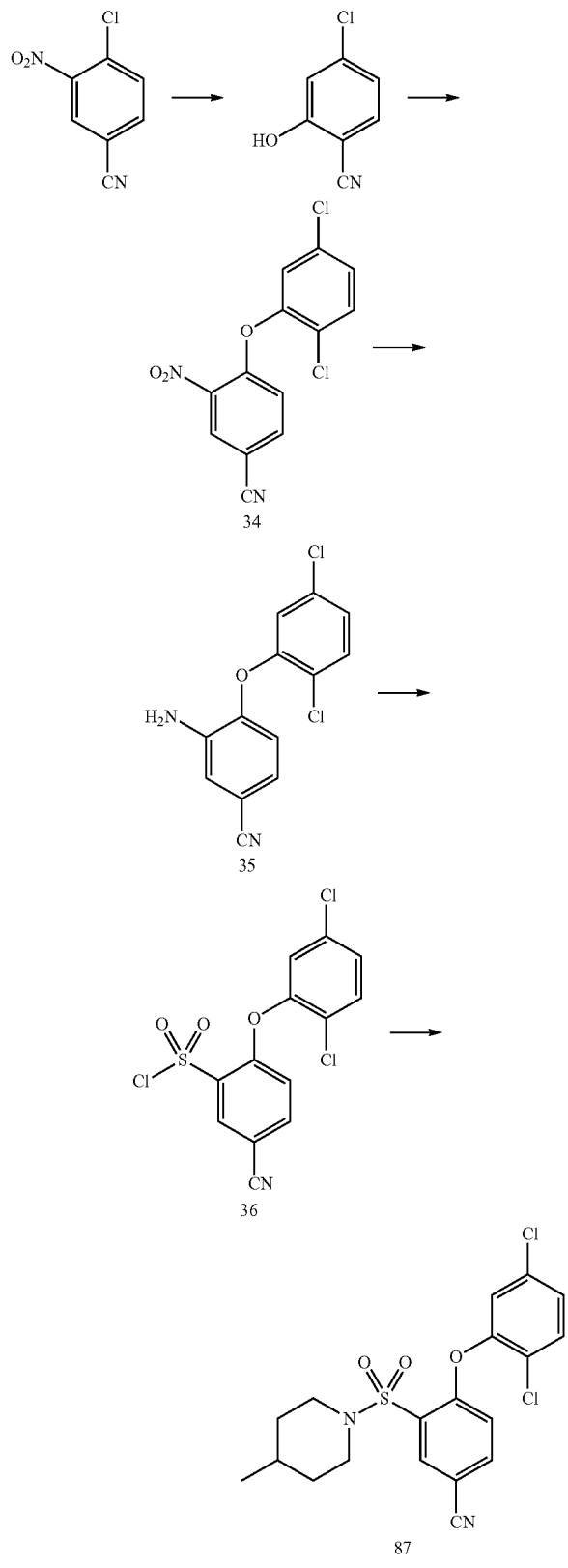

Scheme 7

4-(2,5-Dichlorophenoxy)-3-nitrobenzonitrile 34. 2,5-Dichlorophenol (17.86 g, 109.54 mmol) and 4-chloro-3-nitrobenzonitrile (10.00 g, 54.77 mmol) were combined with $K_2CO_3$ (37.85 g, 273.85 mmol) in THF (300 mL). The reaction mixture was refluxed for 48 hrs and then the solid was filtered over a bed of Celite. After rinsing the residue with copious amounts of DCM, the filtrate was concentrated to produce a yellow solid. The solid was triturated with minimal DCM and collected via vacuum filtration to yield compound 34 (13.84 g, 81.7% yield, 100.0% pure). $^1$H NMR (500 MHz, DMSO-$d_6$): δ 8.73 (s, 1H), 8.12 (dd, $J_1$=9 Hz, $J_2$=2 Hz, 1H), 7.73 (d, J=9 Hz, 1H), 7.65 (d, J=2 Hz, 1H), 7.48 (dd, $J_1$=9 Hz, $J_2$=2 Hz, 1H), 7.21 (d, J=9 Hz, 1H).

3-Amino-4-(2,5-dichlorophenoxy)benzonitrile 35. The coupled product 34 was reduced with sodium hydrosulfite ((49.76 g, 268.56 mmol) in a mixture of THF (200 mL) and water (100 mL). After the reaction was complete, THF was removed in vacuo. The product was precipitated out from the remaining reaction mixture, and was collected via vacuum filtration to yield compound 35 (12.961 g, 103.7% yield, 97.3% pure). $^1$H NMR (500 MHz, DMSO-$d_6$): δ 7.64 (d, J=9 Hz, 1H), 7.31 (dd, $J_1$=9 Hz, $J_2$=2 Hz, 1H), 7.13 (d, J=2 Hz, 1H), 7.08 (d, J=2 Hz, 1H), 6.93 (dd, $J_1$=8 Hz, $J_2$=2 Hz, 1H), 6.74 (d, J=8 Hz, 1H), 5.63 (s, 2H).

5-Cyano-2-(2,5-dichlorophenoxy)benzene-1-sulfonyl chloride 36. For conversion from aniline 35 to sulfonyl chloride 36, the Sandmeyer reaction was utilized. Aniline 35 (5.00 g, 17.91 mmol) was suspended in a mixture of water (20 mL) and conc. HCl (20 mL). The mixture was chilled to 0° C. in an ice bath and an aqueous solution of sodium nitrite (1.85 g, 26.87 mmol) was slowly added, resulting in an orange-white suspension. After addition of sodium nitrite, the mixture was stirred at 0° C. for 1 hr. Separately, 100 mL of acetic acid was saturated with $SO_2$ gas. After 45 minutes of bubbling, copper (II) chloride dihydrate (1.53 g, 8.96 mmol) was added, and the acetic acid solution was stirred until the bright aqua green of the copper turned into a brownish olive green color. The $CuCl_2$ solution was chilled to 0° C., and then the sodium nitrite solution was slowly added to it and left to stir for another hour. An Erlenmeyer flask was filled with crushed ice and enough water to cover the ice. It was agitated on a shaker and the combined solutions were carefully added. The solid product was precipitated out into the ice water and the suspension was agitated until the ice melted. The product 36 as a light pink powder was collected via vacuum filtration (2.363 g, 36.4% yield). $^1$H NMR (500 MHz, DMSO-$d_6$): δ 8.11 (d, J=2 Hz, 1H), 7.80 (dd, $J_1$=8 Hz, $J_2$=2 Hz, 1H), 7.64 (d, J=9 Hz, 1H), 7.30 (dd, $J_1$=9 Hz, $J_2$=2 Hz, 1H), 6.99 (d, J=2 Hz, 1H), 6.95 (d, J=8 Hz, 1H).

4-(2,5-Dichlorophenoxy)-3-(4-methylpiperidin-1-ylsulfonyl)benzonitrile 87. Sulfonyl chloride 36 (0.20 g, 0.55 mmol) was combined with 4-methylpiperidine (0.16 g, 1.65 mmol) and TEA (0.17 g, 1.65 mmol) in DCM (5 mL). The solution was stirred overnight at room temperature. Upon consumption of starting material, as determined via TLC (75% EtOAc in hexanes), the reaction mixture was partitioned between DCM and water. After 3 extractions, the combined organic extracts were washed sequentially with saturated aqueous $NaHCO_3$, water, and brine. The crude product was chromatographed on normal-phase silica to yield the desired product 87 (0.167 g, 71.4% yield, 97.1% pure). $^1$H NMR (500 MHz, DMSO-$d_6$): δ 8.28 (d, J=2 Hz, 1H), 8.07 (dd, $J_1$=9 Hz, $J_2$=2 Hz, 1H), 7.72 (d, J=8 Hz, 1H), 7.46 (dd, $J_1$=5 Hz, $J_2$=2 Hz, 1H), 7.44 (d, J=2 Hz, 1H), 7.10 (d, J=9 Hz, 1H), 3.70 (d, J=12 Hz, 2H), 2.74 (ddd, $J_1$=$J_2$=12 Hz, J3=2 Hz, 2H), 1.65 (dd, $J_1$=13 Hz, $J_2$=2 Hz, 2H), 1.44 (m, 1H), 1.09 (ddd, $J_1$=28 Hz, $J_2$=13 Hz, $J_3$=4 Hz, 2H), 0.87 (d, J=7 Hz, 3H); MS (ESI, EI$^+$): m/z=425.11 (MH$^+$); melting point: 127-130° C.

The following compounds were made according to the procedures as described in this example.

4-(2,5-Dichlorophenoxy)-3-(4-isopropylpiperazin-1-ylsulfonyl)benzonitrile 88. HPLC purity: 100%; $^1$H NMR (500 MHz, DMSO-$d_6$): δ 8.28 (d, J=2 Hz, 1H), 8.09 (dd, $J_1$=9 Hz, $J_2$=2 Hz, 1H), 7.72 (d, J=9 Hz, 1H), 7.48 (d, J=2 Hz, 1H), 7.45 (dd, $J_1$=7 Hz, $J_2$=2 Hz, 1H), 7.13 (d, J=9 Hz, 1H), 3.02 (m, 4H), 2.66 (quintuplet, J=7 Hz, 1H), 2.45 (m, 4H), 0.92 (d, J=7 Hz, 6H); MS (ESI, EI$^+$): m/z=454.14 (MH$^+$); melting point: 186-192° C.

4-(2,5-Dichlorophenoxy)-3-(4-(pentan-3-yl)piperazin-1-ylsulfonyl)-benzonitrile 89. HPLC purity: 98.4%; $^1$H NMR (500 MHz, DMSO-$d_6$): δ 8.28 (d, J=2 Hz, 1H), 8.09 (dd, J=9 Hz, $J_2$=2 Hz, 1H), 7.73 (dd, $J_1$=5 Hz, $J_2$=4 Hz, 1H), 7.45 (m, 2H), 7.14 (d, J=9 Hz, 1H), 3.18 (m, 4H), 2.47 (m, 4H), 2.15 (quintuplet, J=7 Hz, 1H), 1.36 (m, 2H), 1.21 (m, 2H), 0.81 (t, 6H); MS (ESI, EI$^+$): m/z=482.12 (MH$^+$); melting point: 138-141° C.

4-(2,5-Dichlorophenoxy)-3-(4-(pentan-2-yl)piperazin-1-ylsulfonyl)-benzonitrile 90. HPLC purity: 98.5%; $^1$H NMR (500 MHz, DMSO-$d_6$): δ 8.28 (d, J=2 Hz, 1H), 8.09 (dd, $J_1$=9 Hz, $J_2$=2 Hz, 1H), 7.73 (d, J=8 Hz, 1H), 7.46 (dd, $J_1$=4 Hz, $J_2$=2 Hz, 1H), 7.44 (d, J=2 Hz, 1H), 7.14 (d, J=9 Hz, 1H), 3.19 (m, 4H), 2.53 (m, 1H), 2.40 (m, 2H), 1.38 (m, 1H), 1.24 (m, 2H), 1.16 (m, 1H), 0.85 (d, J=6 Hz, 3H), 0.82 (d, J=7 Hz, 3H); MS (ESI, EI$^+$): m/z=482.1 (MH$^+$); melting point: 140-145° C.

3-(4-Cycloheptylpiperazin-1-ylsulfonyl)-4-(2,5-dichlorophenoxy)benzonitrile 91. HPLC purity: 100%; $^1$H NMR (500 MHz, DMSO-$d_6$): δ 8.27 (d, J=2 Hz, 1H), 8.09 (dd, $J_1$=9 Hz, $J_2$=2 Hz, 1H), 7.72 (d, J=9 Hz, 1H), 7.47 (d, J=2 Hz, 1H), 7.44 (dd, $J_1$=9 Hz, $J_2$=2 Hz, 1H), 7.14 (d, J=9 Hz, 1H), 3.18 (m, 4H), 2.47 (m, 4H), 1.42 (m, 13H); MS (ESI, EI$^+$): m/z=508.15 (MH$^+$); melting point: 179-183° C.

4-(2,5-Dichlorophenoxy)-3-(4-methyl-1,4-diazepan-1-ylsulfonyl)benzonitrile 92. HPLC purity: 100%; $^1$H NMR (500 MHz, DMSO-$d_6$): δ 8.28 (d, J=2 Hz, 1H), 8.09 (dd, $J_1$=9 Hz, $J_2$=2 Hz, 1H), 7.72 (d, J=9 Hz, 1H), 7.50 (d, J=2 Hz, 1H), 7.45 (dd, $J_1$=9 Hz, $J_2$=2 Hz, 1H), 7.12 (d, J=9 Hz, 1H), 3.23 (m, 5H), 2.33 (m, 5H), 2.16 (s, 3H); MS (ESI, EI$^+$): m/z=426.15 (MH$^+$); melting point: 169-173° C.

3-(4-(5-Butyl-7-chloro-3-oxo-1H-imidazo[1,5-c]imidazol-2(3H)-yl)piperidin-1-ylsulfonyl)-4-(2,5-dichlorophenoxy)benzonitrile 93. HPLC purity: 99.8%; $^1$H NMR (500 MHz, DMSO-$d_6$): δ 8.30 (d, J=2 Hz, 1H), 8.08 (dd, $J_1$=9 Hz, $J_2$=2 Hz, 1H), 7.74 (d, J=9 Hz, 1H), 7.61 (d, J=2 Hz, 1H), 7.47 (dd, $J_1$=9 Hz, $J_2$=2 Hz, 1H), 7.09 (d, J=9 Hz, 1H), 4.43 (s, 2H), 3.91 (m, 1H), 3.84 (d, J=12 Hz, 2H), 2.95 (dd, $J_1$=12 Hz, $J_2$=11 Hz, 2H), 2.81 (t, J=8 Hz, 2H), 1.85 (d, J=10 Hz, 2H), 1.78 (ddd, $J_1$=25 Hz, $J_2$=12 Hz, $J_3$=4 Hz, 2H), 1.62 (quintuplet, J=7 Hz, 2H), 1.31 (quintuplet, J=7 Hz, 2H), 0.87 (t, J=7 Hz, 3H); MS (ESI, EI$^+$): m/z=624.08 (MH$^+$); melting point: 213-218° C.

4-(2,5-Dichlorophenoxy)-3-(piperazin-1-ylsulfonyl)benzonitrile, dihydrochloride 94. $^1$H NMR (500 MHz, DMSO-$d_6$): δ 9.39 (s, 2H), 8.61 (d, J=2 Hz, 1H), 8.45 (dd, $J_1$=3 Hz, $J_2$=9 Hz, 1H), 7.78 (d, J=9 Hz, 1H), 7.73 (d, J=2 Hz, 1H), 7.53 (dd, $J_1$=2 Hz, $J_2$=8 Hz, 1H), 7.12 (d, J=8 Hz, 1H), 3.57 (m, 4H), 3.16 (m, 4H).

5-Cyano-2-(2,5-dichlorophenoxy)-N-(2-morpholinoethyl)benzenesulfonamide 95. HPLC purity: 98.3%; $^1$H NMR (500 MHz, DMSO-$d_6$): δ 8.26 (d, J=2 Hz, 1H), 8.02 (dd, $J_1$=9 Hz, $J_2$=2 Hz, 1H), 7.87 (t, J=6 Hz, 1H), 7.74 (d, J=8 Hz, 1H), 7.49 (dd, $J_1$=12 Hz, $J_2$=2 Hz, 1H), 7.47 (s, 1H), 6.99 (d, J=9 Hz, 1H), 3.46 (t, J=4 Hz, 4H), 3.09 (quadruplet, J=6 Hz, 2H), 2.36 (t, J=6 Hz, 2H), 2.28 (s, 4H); MS (ESI, EI$^+$): m/z=456 (MH$^+$); melting point: 164-167° C.

4-(2,5-Dichlorophenoxy)-3-(4-methylpiperazin-1-ylsulfonyl)benzonitrile 96. HPLC purity: 99.8%; $^1$H NMR (500 MHz, DMSO-$d_6$): δ 8.28 (d, J=2 Hz, 1H), 8.09 (dd, $J_1$=9 Hz, $J_2$=2 Hz, 1H), 7.72 (d, J=9 Hz, 1H), 7.50 (d, J=2 Hz, 1H), 7.45 (dd, $J_1$=9 Hz, $J_2$=2 Hz, 1H), 7.12 (d, J=9 Hz, 1H), 3.23 (m, 4H), 2.34 (m, 4H), 2.16 (s, 3H); MS (ESI EI$^+$): m/z=467 (MH$^+$); melting point: 168-172° C.

4-(2,5-Dichlorophenoxy)-3-(4-(2-hydroxypropan-2-yl) piperidin-1-ylsulfonyl)benzonitrile 97. HPLC purity: 99.4%; $^1$H NMR (500 MHz, DMSO-$d_6$): δ 8.28 (d, J=2 Hz, 1H), 8.07 (dd, $J_1$=9 Hz, $J_2$=2 Hz, 1H), 7.72 (d, J=9 Hz, 1H), 7.47 (d, J=2 Hz, 1H), 7.45 (dd, $J_1$=8 Hz, $J_2$=2 Hz, 1H), 7.11 (d, J=9 Hz, 1H), 4.17 (s, 1H), 3.80 (d, J=12 Hz, 2H), 2.68 (t. J=12 Hz, 2H), 1.75 (d, J=12 Hz, 2H), 1.25 (m, 1H), 1.18 (m, 2H), 0.99 (s, 6H); MS (ESI, EI$^+$): m/z=451 (MH$^+$); melting point: 95-100° C.

4-(2,5-Dichlorophenoxy)-3-(4-isopropyl-1,4-diazepan-1-ylsulfonyl)benzonitrile, hydrochloride 98. HPLC purity: 99.6%; $^1$H NMR (500 MHz, DMSO-$d_6$): δ 8.29 (d, J=2 Hz, 1H), 7.74 (dd, $J_1$=9 Hz, $J_2$=2 Hz, 1H), 7.47 (d, J=9 Hz, 1H), 7.30 (dd, J1=9 Hz, J2=2 Hz, 1H), 7.25 (d, J=2 Hz, 1H), 6.74 (d, J=9 Hz, 1H), 4.02 (m, 2H), 3.77 (m, 1H), 3.55 (m, 1H), 3.45 (m, 1H), 3.38 (m, 2H), 3.16 (m, 2H), 2.95 (m, 1H), 2.21 (m, 1H), 1.44 (dd, $J_1$=22 Hz, $J_2$=7 Hz, 6H); MS (ESI, EI$^+$): m/z=469 (MH$^+$); melting point: 221-225° C.

Example 6

Preparation of 1-(2-(2,5-dichlorophenoxy)-5-nitrophenylsulfonyl)piperazine

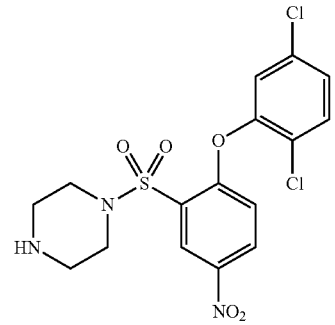

147

Compound 147 was synthesized as shown in Scheme 8.

2-Chloro-5-nitrobenzene-1-sulfonyl chloride 37. To an ice-bath chilled solution of conc. HCl (100 mL) was added 2-chloro-5-nitroaniline (10 g) portion-wise. When complete dissolution was achieved, an aqueous solution of sodium nitrite (6.0 g in 50 mL water) was added dropwise and the resulting reaction mixture was stirred at 0° C. for 1 hr. The above obtained diazonium ion solution was then carefully added to an ice-bath chilled mixture of cupric chloride dihydrate (5 g) in acetic acid (500 mL) pre-saturated with sulfur dioxide gas. After stirring the resulting reaction mixture at 0° C. for 1 hr, it was carefully added portion-wise to an ice-water slurry with vigorous stirring. The separated solids were collected by suction, rinsed with water, and dried under vacuum to furnish the desired product 37 as a cream colored powder (8.2 g, 55%). $^1$H NMR (500 MHz, DMSO-$d_o$): δ 8.61 (d, J=3 Hz, 1H), 8.16 (dd, $J_1$=9 Hz, $J_2$=3 Hz, 1H), 7.70 (d, J=9 Hz, 1H).

Scheme 8

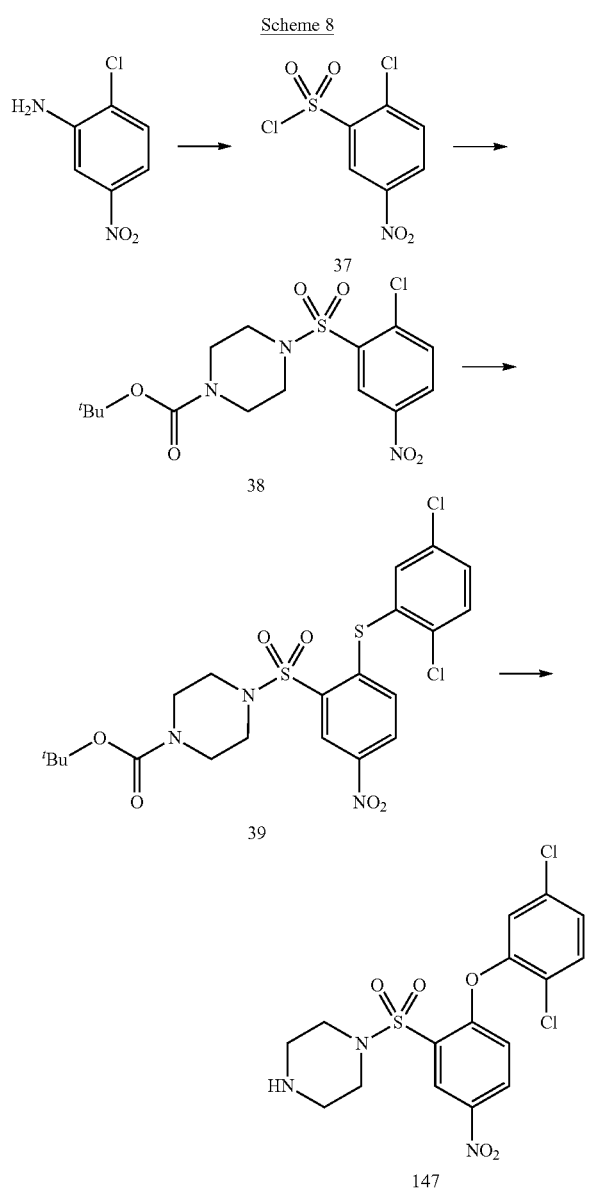

Tert-butyl 4-(2-chloro-5-nitrophenylsulfonyl)piperazine-1-carboxylate 38. A solution of compound 37 (0.600 g, 2.34 mmol) in DCM (20.00 mL) was added tort-butyl 1-piperazinecarboxylate (0.566 g, 3.04 mmol) and TEA (0.422 mL, 3.04 mmol). The reaction was monitored with TLC (25% EtOAc in hexanes, $R_f$=0.53). The reaction mixture was complete after stirring at room temperature for 1 hr, as indicated by the absence of the starting material (TLC). Water was added and aqueous layer was extracted twice with DCM. Combined extracts were sequentially washed with water and brine, dried over MgSO$_4$, filtered, and evaporated in vacuo to afford a yellow solid. The solid was triturated with DCM and hexanes, and then filtered to yield compound 38 as a yellow solid (0.789 g, 100% HPLC purity, 83% yield). $^1$H NMR (500 MHz, DMSO-d$_6$): δ 8.60 (d, J=3 Hz, 1H), 8.47 (dd, J$_1$=3 Hz, J$_2$=8 Hz, 1H), 8.01 (d, J=8 Hz, 1H), 3.37 (m, 4H), 3.23 (m, 4H), 1.37 (s, 9H).

Tert-butyl 4-(2-(2,5-dichlorophenoxy)-5-nitrophenylsulfonyl)piperazine-1-carboxylate 39. To a solution of 2,5-dichlorophenol (0.414 g, 2.54 mmol) in THF (20.00 mL) stirred in an ice bath was added NaH (0.101 g, 2.54 mmol) slowly. After addition, the mixture was stirred for 5 min. Compound 38 (0.790 g, 1.95 mmol) was then added and the resulting reaction mixture was heated to 75° C. overnight. The reaction was monitored by HPLC. However, the reaction was not complete after 16 hrs (HPLC), so THF was evaporated and 18-crown-6 (1.057 g, 4.00 mmol), DMF (15 mL), and K$_2$CO$_3$ (0.553 g, 4.00 mmol) were added. The reaction mixture was heated to 100° C. for another 16 hrs, at which time HPLC indicated that the reaction was complete by absence of starting material. The reaction mixture was cooled to room temperature, and water (0.250 mL) was added. The reaction mixture was extracted thrice with EtOAc. Combined extracts were washed sequentially with 1N NaOH, water, and brine, dried over MgSO$_4$, filtered, and evaporated in vacuo. The residual was dissolved in a minimal amount of DCM and purified with chromatography using a gradient of 5 to 30% EtOAc in hexanes. Pure fractions were combined and evaporated in vacuo. The resulting solid was triturated with DCM and hexanes, and then filtered to afford compound 39 as a white/yellow powder (0.120 g, 100% HPLC purity, 10.0% yield). $^1$H NMR (500 MHz, DMSO-d$_6$): δ 8.59 (d, J=2 Hz, 1H), 8.42 (dd, J$_1$=2 Hz, J$_2$=8 Hz, 1H), 7.76 (d, J=8 Hz, 1H), 7.66 (d, J=3 Hz, 1H), 7.50 (dd, J$_1$=2 Hz, J$_2$=8 Hz, 1H), 7.10 (d, J=8 Hz, 1H), 3.40 (m, 4H), 3.25 (m, 4H), 1.37 (s, 9H).

1-(2-(2,5-Dichlorophenoxy)-5-nitrophenylsulfonyl)piperazine 147. To a solution of compound 39 (0.100 g, 0.19 mmol) in DCM (6.00 mL) was added 1N HCl in 1,4-dioxane (0.570 mL). The reaction was monitored with TLC (25% EtOAc in hexanes, R$_f$=0.0). The reaction was complete after stirring at room temperature for 16 hrs, as indicated by the absence of the starting material). The reaction mixture was concentrated and the residual was redissolved in MeOH (2.00 mL). Et$_2$O (4.00 mL) was then added and the mixture was stirred until precipitate formed (10 min). The solid was collected by filtration to yield compound 147 as a white solid (0.080 g, 100% HPLC purity, 83% yield). $^1$H NMR (500 MHz, DMSO-d$_6$): δ 9.39 (s, 2H), 8.61 (d, J=2 Hz, 1H), 8.45 (dd, J$_1$=3 Hz, J$_2$=9 Hz, 1H), 7.78 (d, J=9 Hz, 1H), 7.73 (d, J=2 Hz, 1H), 7.53 (dd, J$_1$=2 Hz, J$_2$=8 Hz, 1H), 7.12 (d, J=8 Hz, 1H), 3.57 (m, 4H), 3.16 (m, 4H).

1-(2-(2,5-Chlorophenoxy)-5-nitrophenylsulfonyl)piperazine, hydrochloride 147. HPLC purity: 100%; $^1$H NMR (500 MHz, DMSO-d$_6$): δ 8.95 (s, 1H), 8.61 (d, J=2 Hz, 1H), 8.46 (dd, J$_1$=2 Hz, J$_2$=8 Hz, 1H), 7.78 (d, J=8 Hz, 1H), 7.62 (d, J=2 Hz, 1H), 7.53 (dd, J$_1$=2 Hz, J$_2$=8 Hz, 1H), 7.14 (d, J=8 Hz, 1H), 3.52 (m, 4H), 3.20 (m, 4H); melting point: 224-227° C.

1-(2-(2,5-Chlorophenoxy)-5-nitrophenylsulfonyl)piperazine, dihydrochloride 147. HPLC purity: 100%; $^1$H NMR (500 MHz, DMSO-d$_6$): δ 9.39 (s, 2H), 8.61 (d, J=2 Hz, 1H), 8.45 (dd, J$_1$=3 Hz, J$_2$=9 Hz, 1H), 7.78 (d, J=9 Hz, 1H), 7.73 (d, J=2 Hz, 1H), 7.53 (dd, J$_1$=2 Hz, J$_2$=8 Hz, 1H), 7.12 (d, J=8 Hz, 1H), 3.57 (m, 4H), 3.16 (m, 4H).

The following compounds were made according to the procedures as described in this example.

1-(2-(2,5-Dimethylphenylthio)-5-nitrophenylsulfonyl)-4-(pyrrolidin-1-yl)piperidine 75. HPLC purity: 100%; $^1$H NMR (500 MHz, CDCl$_3$) δ 8.77 (d, J=3 Hz, 1H), 8.02 (dd, J$_1$=9 Hz, J$_2$=3 Hz, 1H), 7.39 (s, 1H), 7.30 (d, J=8 Hz, 1H), 7.27 (m, 1H), 6.78 (d, J=9 Hz, 1H), 3.87 (m, 2H), 3.00 (m, 2H), 2.55 (s, 4H), 2.36 (s, 3H), 2.29 (s, 3H), 2.16 (m, 1H), 1.97 (m, 2H), 1.78 (m, 4H), 1.68 (m, 2H); MS (ESI, EI$^+$): m/z=476 (MH$^+$); melting point: 184-188° C.

1-(2-(2,5-Dichlorophenoxy)-5-nitrophenylsulfonyl)-4-ethylpiperazine 100. HPLC purity: 100%; $^1$H NMR (500 MHz, DMSO-d$_6$): δ 8.58 (d, J=2 Hz, 1H), 8.43 (dd, J$_1$=2 Hz, J$_2$=8 Hz, 1H), 7.75 (d, J=8 Hz, 1H), 7.59 (d, J=2 Hz, 1H), 7.49

(dd, J$_1$=2 Hz, J$_2$=8 Hz, 1H), 7.14 (d, J=8 Hz, 1H), 3.26 (m, 4H), 2.40 (m, 4H), 2.33 (m, 2H), 0.95 (t, J$_1$=J$_2$=7 Hz, 3H); melting point: 152-155° C.

1-(2-(2,5-Dimethylphenylthio)-5-nitrophenylsulfonyl)-4-ethylpiperazine 101. HPLC purity: 100%; $^1$H NMR (500 MHz, DMSO-d$_6$): δ 8.50 (d, J=2 Hz, 1H), 8.25 (dd, J$_1$=2 Hz, J$_2$=8 Hz, 1H), 7.46 (s, 1H), 7.41 (d, J=8 Hz, 1H), 7.35 (d, J=8 Hz, 1H), 6.81 (d, J=8 Hz, 1H), 3.28 (s, 4H), 2.45 (s, 4H), 2.35 (m, 2H), 2.32 (s, 3H), 2.24 (s, 3H), 0.97 (t, J$_1$=J$_2$=7 Hz, 3H); melting point: 120-123° C.

1-(2-(2,5-Dimethylphenoxy)-5-nitrophenylsulfonyl)-4-ethylpiperazine 102. HPLC purity: 100%; $^1$H NMR (500 MHz, DMSO-d$_6$): δ 8.58 (d, J=2 Hz, 1H), 8.40 (dd, J$_1$=2 Hz, J$_2$=8 Hz, 1H), 7.31 (d, J=8 Hz, 1H), 7.11 (d, J=8 Hz, 1H), 7.00 (s, 1H), 6.85 (d, J=8 Hz, 1H), 3.27 (s, 4H), 2.41 (s, 4H), 2.36 (m, 2H), 2.30 (s, 3H), 2.09 (s, 3H), 0.96 (t, J$_1$=J$_2$=7 Hz, 3H); melting point: 105-111° C.

1-(2-(2,5-Dichlorophenylthio)-5-nitrophenylsulfonyl)-3,5-dimethylpiperazine 103. HPLC purity: 95%; $^1$H NMR (500 MHz, DMSO-d$_6$): δ 8.49 (d, J=2 Hz, 1H), 8.26 (dd, J$_1$=2 Hz, J$_2$=8 Hz, 1H), 7.94 (d, J=2 Hz, 1H), 7.80 (d, J=8 Hz, 1H), 7.73 (dd, J$_1$=2 Hz, J$_2$=8 Hz, 1H), 7.00 (d, J=8 Hz, 1H), 3.63 (m, 2H), 2.74 (m, 2H), 2.25 (t, J$_1$=J$_2$=7 Hz, 3H), 0.94 (d, J=8 Hz, 6H); melting point: 169-171° C.

1-(2-(2,5-Dichlorophenoxy)-5-nitrophenylsulfonyl)-3,5-dimethylpiperazine 104. HPLC purity: 100%; $^1$H NMR (500 MHz, DMSO-d$_6$): δ 8.58 (d, J=2 Hz, 1H), 8.44 (dd, J$_1$=2 Hz, J$_2$=8 Hz, 1H), 7.76 (d, J=8 Hz, 1H), 7.48 (m, 2H), 7.18 (d, J=8 Hz, 1H), 3.57 (m, 2H), 2.70 (m, 2H), 2.25 (m, 3H), 0.92 (d, J=8 Hz, 6H); melting point: 161-163° C.

1-(2-(2,5-Dimethylphenylthio)-5-nitrophenylsulfonyl)-3,5-dimethylpiperazine 105. HPLC purity: 99.7%; $^1$H NMR (500 MHz, DMSO-d$_6$): δ 8.49 (d, J=2 Hz, 1H), 8.24 (dd, J$_1$=2 Hz, J$_2$=8 Hz, 1H), 7.42 (m, 2H), 7.35 (d, J=8 Hz, 1H), 6.80 (d, J=8 Hz, 1H), 3.63 (m, 2H), 2.75 (m, 2H), 2.33 (s, 3H), 2.27 (m, 2H), 2.23 (s, 3H), 0.95 (d, J=8 Hz, 6H); melting point: 156-159° C.

1-(2-(2,5-Dimethylphenoxy)-5-nitrophenylsulfonyl)-3,5-dimethylpiperazine 106. HPLC purity: 100%; $^1$H NMR (500 MHz, DMSO-d$_6$): δ 8.57 (d, J=2 Hz, 1H), 8.40 (dd, J$_1$=2 Hz, J$_2$=8 Hz, 1H), 7.31 (d, J=8 Hz, 1H), 7.10 (d, J=8 Hz, 1H), 6.94 (s, 1H), 6.84 (d, J=8 Hz, 1H), 3.58 (m, 2H), 2.72 (m, 2H), 2.30 (s, 3H), 2.26 (m, 2H), 2.10 (s, 3H), 0.92 (d, J=8 Hz, 6H); melting point: 148-151° C.

1-(2-(2,5-Dichlorophenoxy)-5-nitrophenylsulfonyl)-4-isopropylpiperazine 107. HPLC purity: 98.8%; $^1$H NMR (500 MHz, DMSO-d$_6$): δ 8.58 (d, J=3 Hz, 1H), 8.43 (dd, J$_1$=9 Hz, J$_2$=3 Hz, 1H), 7.76 (d, J=9 Hz, 1H), 7.57 (d, J=2 Hz, 1H), 7.49 (dd, J$_1$=9 Hz, J$_2$=2 Hz, 1H), 7.16 (d, J=9 Hz, 1H), 3.23 (t, J=4 Hz, 4H), 2.67 (m, 1H), 2.47 (t, J=5 Hz, 4H), 0.92 (d, J=7 Hz, 6H); MS (ESI, EI$^+$): m/z=474 (MH$^+$); melting point: 160-166° C.

1-(2-(2,5-Dichlorophenylthio)-5-nitrophenylsulfonyl)-4-isopropylpiperazine 108. HPLC purity: 99.3%; $^1$H NMR (500 MHz, DMSO-d$_6$): δ 8.75 (d, J=2 Hz, 1H), 8.11 (dd, J$_1$=9 Hz, J$_2$=3 Hz, 1H), 7.71 (d, J=2 Hz, 1H), 7.55 (d, J=9 Hz, 1H), 7.48 (dd, J$_1$=9 Hz, J$_2$=2 Hz, 1H), 6.85 (d, J=9 Hz, 1H), 3.39 (m, 4H), 2.73 (m, 1H), 2.63 (m, 4H), 1.03 (d, J=7 Hz, 6H); MS (ESI, EI$^+$): m/z=490 (MH$^+$); melting point: 129-134° C.

1-(2-(2,5-Dimethylphenoxy)-5-nitrophenylsulfonyl)-4-isopropylpiperazine 109. HPLC purity: 99.7%; $^1$H NMR (500 MHz, DMSO-d$_6$): δ 8.86 (d, J=3 Hz, 1H), 8.23 (dd, J$_1$=9 Hz, J$_2$=3 Hz, 1H), 7.21 (d, J=8 Hz, 1H), 7.05 (d, J=7 Hz, 1H), 6.85 (s, 1H), 6.72 (d, J=9 Hz, 1H), 3.41 (t, J=5 Hz, 4H), 2.73 (m, 1H), 2.60 (t, J=5 Hz, 4H), 2.34 (s, 3H), 2.15 (s, 3H), 1.03 (d, J=7 Hz, 6H); MS (ESI, EI$^+$): m/z=434 (MH$^+$); melting point: 128-131° C.

4-(2-(2,5-Dichlorophenylthio)-5-nitrophenylsulfonyl)morpholine 110. HPLC purity: 99%; $^1$H NMR (500 MHz, DMSO-d$_6$): δ 8.51 (d, J=2 Hz, 1H), 8.29 (dd, J$_1$=2 Hz, J$_2$=8 Hz, 1H), 8.00 (d, J=2 Hz, 1H), 7.82 (d, J=8 Hz, 1H), 7.74 (dd, J$_1$=2 Hz, J$_2$=8 Hz, 1H), 7.02 (d, J=8 Hz, 1H), 3.67 (m, 4H), 3.28 (m, 4H); melting point: 182-186° C.

4-(2-(2,5-Dichlorophenoxy)-5-nitrophenylsulfonyl)morpholine 111. HPLC purity: 100%; $^1$H NMR (500 MHz, DMSO-d$_6$): δ 8.59 (d, J=2 Hz, 1H), 8.44 (dd, J$_1$=2 Hz, J$_2$=8 Hz, 1H), 7.76 (d, J=2 Hz, 1H), 7.65 (d, J=8 Hz, 1H), 7.50 (dd, J$_1$=2 Hz, J$_2$=8 Hz, 1H), 7.14 (d, J=8 Hz, 1H), 3.673 (m, 4H), 3.26 (m, 4H); melting point: 168-170° C.

4-(2-(2,5-Dimethylphenylthio)-5-nitrophenylsulfonyl)morpholine 112. HPLC purity: 100%; $^1$H NMR (500 MHz, DMSO-d$_6$): δ 8.50 (d, J=2 Hz, 1H), 8.27 (dd, J$_1$=2 Hz, J$_2$=8 Hz, 1H), 7.48 (s, 1H), 7.42 (d, J=8 Hz, 1H), 7.36 (d, J=7 Hz, 1H), 6.82 (d, J=8 Hz, 1H), 3.67 (m, 4H), 3.28 (m, 4H), 2.33 (s, 3H), 2.25 (s, 3H); melting point: 141-143° C.

4-(2-(2,5-Dimethylphenoxy)-5-nitrophenylsulfonyl)morpholine 113. HPLC purity: 100%; $^1$H NMR (500 MHz. DMSO-d$_6$): δ 8.59 (d, J=2 Hz, 1H), 8.41 (dd, J$_1$=2 Hz, J$_2$=8 Hz, 1H), 7.31 (d, J=8 Hz, 1H), 7.11 (d, J=7 Hz, 1H), 7.05 (s, 1H), 6.85 (d, J=8 Hz, 1H), 3.64 (m, 4H), 3.27 (m, 4H), 2.31 (s, 3H), 2.10 (s, 3H); melting point: 124-127° C.

4-(2-(2,5-Dichlorophenylthio)-5-nitrophenylsulfonyl)thiomorpholine 114. HPLC purity: 99%; $^1$H NMR (500 MHz, DMSO-d$_6$): δ 8.55 (d, J=2 Hz, 1H), 8.27 (dd, J$_1$=2 Hz, J$_2$=8 Hz, 1H), 7.98 (d, J=2 Hz, 1H), 7.80 (d, J=8 Hz, 1H), 7.73 (dd, J$_1$=2 Hz, J$_2$=8 Hz, 1H), 7.03 (d, J=8 Hz, 1H), 3.59 (m, 4H), 2.70 (m, 4H); melting point: 189-191° C.

4-(2-(2,5-Dichlorophenoxy)-5-nitrophenylsulfonyl)thiomorpholine 115. HPLC purity: 100%; $^1$H NMR (500 MHz, DMSO-d$_6$): δ 8.60 (d, J=2 Hz, 1H), 8.42 (dd, J$_1$=2 Hz, J$_2$=8 Hz, 1H), 7.77 (d, J=8 Hz, 1H), 7.66 (d, J=2 Hz, 1H), 7.51 (dd, J$_1$=2 Hz, J$_2$=8 Hz, 1H), 7.09 (d, J=8 Hz, 1H), 3.54 (m, 4H), 2.67 (m, 4H); melting point: 191-194° C.

4-(2-(2,5-Dimethylphenylthio)-5-nitrophenylsulfonyl)thiomorpholine 116. HPLC purity: 99.5%; $^1$H NMR (500 MHz, DMSO-d$_6$): δ 8.59 (d, J=2 Hz, 1H), 8.40 (dd, J$_1$=2 Hz, J$_2$=8 Hz, 1H), 7.32 (d, J=8 Hz, 1H), 7.12 (d, J=7 Hz, 1H), 7.04 (s, 1H), 6.83 (d, J=8 Hz, 1H), 3.54 (m, 4H), 2.67 (m, 4H), 2.32 (s, 3H), 2.09 (s, 3H); melting point: 130-137° C.

4-(2-(2,5-Dimethylphenoxy)-5-nitrophenylsulfonyl)thiomorpholine 117. HPLC purity: 100%; $^1$H NMR (500 MHz, DMSO-d$_6$): δ 8.53 (d, J=2 Hz, 1H), 8.25 (dd, J$_1$=2 Hz, J$_2$=8 Hz, 1H), 7.47 (s, 1H), 7.41 (d, J=7 Hz, 1H), 7.36 (d, J=7 Hz, 1H), 6.82 (d, J=8 Hz, 1H), 3.59 (m, 4H), 2.71 (m, 4H), 2.33 (s, 3H), 2.24 (s, 3H); melting point: 144-147° C.

1-Cyclohexyl-4-(2-(2,5-dichlorophenylthio)-5-nitrophenylsulfonyl)piperazine 118. HPLC purity: 100%; $^1$H NMR (500 MHz, DMSO-d$_6$): δ 8.50 (d, J=2 Hz, 1H), 8.27 (dd, J$_1$=2 Hz, J$_2$=8 Hz, 1H), 7.93 (d, J=2 Hz, 1H), 7.80 (d, J=8 Hz, 1H), 7.72 (dd, J$_1$=2 Hz, J$_2$=8 Hz, 1H), 7.02 (d, J=8 Hz, 1H), 3.26 (m, 4H), 2.56 (m, 4H), 2.25 (m, 1H), 1.68 (m, 4H), 1.53 (m, 1H), 1.13 (m, 4H), 1.02 (m, 1H); melting point: 153-155° C.

1-Cyclohexyl-4-(2-(2,5-dichlorophenoxy)-5-nitrophenylsulfonyl)piperazine 119. HPLC purity: 100%; $^1$H NMR (500 MHz, DMSO-d$_6$): δ 8.49 (d, J=2 Hz, 1H), 8.25 (dd, J$_1$=2 Hz, J$_2$=8 Hz, 1H), 7.45 (s, 1H), 7.41 (d, J=7 Hz, 1H), 7.35 (d, J=7 Hz, 1H), 6.81 (d, J=8 Hz, 1H), 3.25 (m, 4H), 2.57 (m, 4H), 2.32 (s, 3H), 2.26 (m, 1H), 2.25 (s, 3H), 1.69 (m, 4H), 1.54 (m, 1H), 1.16 (m, 4H), 1.05 (m, 1H); melting point: 170-172° C.

1-Cyclohexyl-4-(2-(2,5-dimethylphenylthio)-5-nitrophenylsulfonyl)piperazine 120. HPLC purity: 100%; $^1$H NMR (500 MHz, DMSO-d$_6$): δ 8.57 (d, J=2 Hz, 1H), 8.43 (dd, J$_1$=2 Hz, J$_2$=8 Hz, 1H), 7.75 (d, J=8 Hz, 1H), 7.56 (d, J=2 Hz, 1H), 7.48 (dd, J$_1$=2 Hz, J$_2$=8 Hz, 1H), 7.15 (d, J=8 Hz, 1H), 3.22

(m, 4H), 2.52 (m, 4H), 2.23 (m, 1H), 1.69 (m, 4H), 1.54 (m, 1H), 1.14 (m, 4H), 1.04 (m, 1H); melting point: 161-163° C.

1-Cyclohexyl-4-(2-(2,5-dimethylphenoxy)-5-nitrophenylsulfonyl)piperazine 121. HPLC purity: 100%; $^1$H NMR (500 MHz, DMSO-d$_6$): δ 8.57 (d, J=2 Hz, 1H), 8.40 (dd, $J_1$=2 Hz, $J_2$=8 Hz, 1H), 7.31 (d, J=8 Hz, 1H), 7.10 (d, J=8 Hz, 1H), 6.99 (s, 1H), 6.85 (d, J=8 Hz, 1H), 3.23 (m, 4H), 2.52 (m, 4H), 2.30 (s, 3H), 2.26 (m, 1H), 2.09 (s, 3H), 1.68 (m, 4H), 1.54 (m, 1H), 1.13 (m, 4H), 1.03 (m, 1H); melting point: 140-142° C.

1-(2-(2,5-Dimethylphenylthio)-5-nitrophenylsulfonyl)piperazine 122. HPLC purity: 100%; $^1$H NMR (500 MHz, DMSO-d$_6$): δ 8.49 (d, J=2 Hz, 1H), 8.25 (dd, $J_1$=2 Hz, $J_2$=8 Hz, 1H), 7.45 (s, 1H), 7.42 (d, J=8 Hz, 1H), 7.35 (d, J=8 Hz, 1H), 6.81 (d, J=8 Hz, 1H), 3.18 (m, 4H), 2.76 (m, 4H), 2.33 (s, 3H), 2.24 (s, 3H); melting point: 142-145° C.

1-(2-(2,5-Dichlorophenylthio)-5-nitrophenylsulfonyl)piperazine 123. HPLC purity: 100%; $^1$H NMR (500 MHz, DMSO-d$_6$): δ 8.49 (d, J=2 Hz, 1H), 8.27 (dd, $J_1$=2 Hz, $J_2$=8 Hz, 1H), 7.96 (d, J=2 Hz, 1H), 7.81 (d, J=8 Hz, 1H), 7.74 (dd, $J_1$=2 Hz, $J_2$=8 Hz, 1H), 7.01 (d, J=8 Hz, 1H), 3.18 (m, 4H), 2.74 (m, 4H); melting point: 150-153° C.

4-(2-(2,5-Dichlorophenylthio)-5-nitrophenylsulfonyl)piperazin-2-one 124. HPLC purity: 99%; $^1$H NMR (500 MHz, DMSO-d$_6$): δ 8.57 (d, J=2 Hz, 1H), 8.29 (dd, $J_1$=2 Hz, $J_2$=8 Hz, 1H), 8.16 (s, 1H), 7.98 (d, J=2 Hz, 1H), 7.81 (d, J=8 Hz, 1H), 7.73 (dd, $J_1$=2 Hz, $J_2$=8 Hz, 1H), 7.03 (d, J=8 Hz, 1H), 3.89 (s, 2H), 3.59 (m, 2H), 3.24 (m, 2H); melting point: 252-255° C.

4-(2-(2,5-Dimethylphenylthio)-5-nitrophenylsulfonyl)piperazin-2-one 125. HPLC purity: 99%; $^1$H NMR (500 MHz, DMSO-d$_6$): δ 8.56 (d, J=2 Hz, 1H), 8.27 (dd, $J_1$=2 Hz, $J_2$=8 Hz, 1H), 8.17 (s, 1H), 7.45 (s, 1H), 7.42 (d, J=8 Hz, 1H), 7.35 (d, J=8 Hz, 1H), 6.82 (d, J=8 Hz, 1H), 3.90 (s, 2H), 3.59 (m, 2H), 3.23 (m, 2H), 2.32 (s, 3H), 2.23 (s, 3H); melting point: 196-202° C.

4-(2-(2,5-Dichlorophenoxy)-5-nitrophenylsulfonyl)piperazin-2-one 126. HPLC purity: 99%; $^1$H NMR (500 MHz, DMSO-d$_6$): δ 8.63 (d, J=2 Hz, 1H), 8.43 (dd, $J_1$=2 Hz, $J_2$=8 Hz, 1H), 8.15 (s, 1H), 7.77 (d, J=8 Hz, 1H), 7.68 (d, J=2 Hz, 1H), 7.52 (dd, $J_1$=2 Hz, $J_2$=8 Hz, 1H), 7.08 (d, J=8 Hz, 1H), 3.84 (s, 2H), 3.56 (m, 2H), 3.19 (m, 2H); melting point: 249-251° C.

1-(2-(2,5-Dichlorophenylthio)-5-nitrophenyl sulfonyl)-1,4-diazepane 127. HPLC purity: 99.5%; $^1$H NMR (500 MHz, DMSO-d$_6$): δ 8.56 (d, J=2 Hz, 1H), 8.24 (dd, $J_1$=2 Hz, $J_2$=8 Hz, 1H), 7.92 (d, J=2 Hz, 1H), 7.78 (d, J=8 Hz, 1H), 7.71 (dd, $J_1$=2 Hz, $J_2$=8 Hz, 1H), 7.03 (d, J=8 Hz, 1H), 3.50 (m, 2H), 3.43 (m, 2H), 2.81 (m, 5H), 1.73 (m, 2H); melting point: 190-193° C.

1-(2-(2,5-Dimethylphenylthio)-5-nitrophenylsulfonyl)-1,4-diazepane 128. HPLC purity: 100%; $^1$H NMR (500 MHz, DMSO-d$_6$): δ 8.55 (d, J=2 Hz, 1H), 8.22 (dd, $J_1$=2 Hz, $J_2$=8 Hz, 1H), 7.45 (s, 1H), 7.39 (d, J=8 Hz, 1H), 7.34 (d, J=8 Hz, 1H), 6.81 (d, J=8 Hz, 1H), 3.50 (m, 2H), 3.48 (m, 2H), 2.83 (m, 4H), 2.32 (s, 3H), 2.21 (s, 3H), 1.75 (s, 2H); melting point: 80-90° C.

1-(2-(2,5-Dichlorophenylthio)-5-nitrophenylsulfonyl)-4-(pyrrolidin-1-yl)piperidine 129. HPLC purity: 100%; $^1$H NMR (500 MHz, CDCl$_3$) δ 8.78 (d, J=3 Hz, 1H), 8.10 (dd, $J_1$=9 Hz, $J_2$=3 Hz, 1H), 7.72 (d, J=3 Hz, 1H), 7.54 (d, J=9 Hz, 1H), 7.48 (dd, $J_1$=9 Hz, $J_2$=2 Hz, 1H), 6.86 (d, J=9 Hz, 1H), 3.86 (m, 2H), 3.00 (m, 2H), 2.54 (s, 4H), 2.18 (m, 1H), 1.96 (m, 2H), 1.78 (s, 4H), 1.68 (m, 2H); MS (ESI, EI$^+$): m/z=516 (MH$^+$); melting point: 184-188° C.

1-(2-(2,5-Dimethylphenoxy)-5-nitrophenylsulfonyl)-4-(pyrrolidin-1-yl)piperidine 130. HPLC purity: 100%; $^1$H NMR (500 MHz, CDCl$_3$) δ 8.87 (d, J=3 Hz, 1H), 8.22 (dd, $J_1$=9 Hz, $J_2$=3 Hz, 1H), 7.21 (d, J=8 Hz, 1H), 7.05 (d, J=7 Hz, 1H), 6.85 (s, 1H), 6.70 (d, J=10 Hz, 1H), 3.87 (m, 2H), 2.99 (m, 2H), 2.53 (m, 4H), 2.34 (s, 3H), 2.15 (s, 3H), 1.93 (m, 2H), 1.77 (m, 4H), 1.65 (m, 3H); MS (ESI, EI$^+$): m/z=460 (MH$^+$); melting point: 95-102° C.

1-(2-(2,5-Dimethylphenylthio)-5-nitrophenylsulfonyl)-4-isopropylpiperazine 131. HPLC purity: 99.6%; $^1$H NMR (500 MHz, CDCl$_3$) δ 8.73 (d, J=2 Hz, 1H), 8.02 (dd, $J_1$=9 Hz, $J_2$=2 Hz, 1H), 7.37 (s, 1H), 7.30 (d, J=8 Hz, 1H), 7.27 (d, J=6 Hz, 1H), 6.76 (d, J=9 Hz, 1H), 3.40 (t, J=4 Hz, 4H), 2.74 (quintuplet, J=7 Hz, 1H), 2.64 (t, J=5.4H), 2.35 (s, 3H), 2.30 (s, 3H), 1.04 (d, J=7 Hz, 6H); MS (ESI, EI$^+$): m/z=450 (MH$^+$); melting point: 120-124° C.

1-(2-(2,5-Dimethylphenylthio)-5-nitrophenylsulfonyl)-4-methylpiperazine 132. HPLC purity: 100%; $^1$H NMR (500 MHz, CDCl$_3$) δ 8.75 (d, J=2 Hz, 1H), 8.03 (dd, $J_1$=9 Hz, $J_2$=2 Hz, 1H), 7.37 (s, 1H), 7.30 (d, J=8 Hz, 1H), 7.27 (d, J=1 Hz, 1H), 6.77 (d, J=9 Hz, 1H), 3.43 (t, J=4 Hz, 4H), 2.53 (t, J=5 Hz, 4H), 2.36 (s, 3H), 2.33 (s, 3H), 2.29 (s, 3H); MS (ESI, EI$^+$): m/z=422 (MH$^+$); melting point: 136-144° C.

1-(2-(2,5-Dichlorophenylthio)-5-nitrophenylsulfonyl)-4-methylpiperazine 133. HPLC purity: 100%; $^1$H NMR (500 MHz, CDCl$_3$) δ 8.76 (d, J=2 Hz, 1H), 8.11 (dd, $J_1$=9 Hz, $J_2$=2 Hz, 1H), 7.71 (d, J=2 Hz, 1H), 7.55 (d, J=9 Hz, 1H), 7.48 (dd, $J_1$=9 Hz, $J_2$=2 Hz, 1H), 6.86 (d, J=9 Hz, 1H), 3.42 (m, 4H), 2.51 (m, 4H), 2.31 (s, 3H); MS (ESI, EI$^+$): m/z=461 (MH$^+$); melting point: 105-115° C.

1-(2-(2,5-Dichlorophenylthio)-5-nitrophenylsulfonyl)-4-methyl-1,4-diazepane 134. HPLC purity: 100%; $^1$H NMR (500 MHz, CDCl$_3$) δ 8.82 (d, J=3 Hz, 1H), 8.10 (dd, $J_1$=9 Hz, $J_2$=2 Hz, 1H), 7.71 (d, J=2 Hz, 1H), 7.53 (d, J=9 Hz, 1H), 7.47 (dd, $J_1$=9 Hz, $J_2$=2 Hz, 1H), 6.88 (d, J=9 Hz, 1H), 3.66 (m, 2H), 3.57 (t, J=6 Hz, 2H), 2.72 (m, 4H), 2.39 (s, 3H), 1.96 (quintuplet, J=6 Hz, 2H); MS (ESI, EI$^+$): m/z=476 (MH$^+$); melting point: 116-119° C.

1-(2-(2,5-Dichlorophenoxy)-5-nitrophenylsulfonyl)-4-methylpiperazine 135. HPLC purity: 100%; $^1$H NMR (500 MHz, DMSO-d$_6$): δ 8.59 (d, J=3 Hz, 1H), 8.43 (dd, $J_1$=9 Hz, $J_2$=3 Hz, 1H), 7.76 (d, J=9 Hz, 1H), 7.59 (d, J=2 Hz, 1H), 7.50 (dd, $J_1$=9 Hz, $J_2$=2 Hz, 1H), 7.14 (d, J=9 Hz, 1H), 3.26 (t. J=5 Hz, 4H), 2.35 (t, J=5 Hz, 4H), 2.16 (s, 3H); MS (ESI, EI$^+$): m/z=446 (MH$^+$); melting point: 172-176° C.

1-(2-(2,5-Dimethylphenoxy)-5-nitrophenylsulfonyl)-4-methyl-1,4-diazepane, hydrochloride 136. HPLC purity: 96.4%; $^1$H NMR (500 MHz, CDCl$_3$) δ 12.50 (s, 1H), 8.86 (d, J=3 Hz, 1H), 8.28 (dd, $J_1$=9 Hz, $J_2$=3 Hz, 1H), 7.22 (d, J=8 Hz, 1H), 7.09 (d, J=8 Hz, 1H), 6.86 (s, 1H), 6.73 (d, J=9 Hz, 1H), 4.12 (m, 1H), 3.84 (m, 2H), 3.52 (m, 2H), 3.40 (m, 1H), 3.32 (m, 1H), 3.16 (m, 1H), 2.92 (m, 1H), 2.88 (d, J=5 Hz, 3H), 2.36 (s, 3H), 2.24 (m, 1H), 2.11 (s, 3H); MS (ESI, EI$^+$): m/z=420 (MH$^+$): melting point: 268-275° C.

1-(2-(2,5-Dimethylphenylthio)-5-nitrophenylsulfonyl)-4-methyl-1,4-diazepane, hydrochloride 137. HPLC purity: 95.5%; $^1$H NMR (500 MHz, DMSO-d$_6$): δ 12.50 (s, 1H), 8.80 (d, J=2 Hz, 1H), 8.07 (dd, $J_1$=9 Hz, $J_2$=2 Hz, 1H), 7.36 (s, 1H), 7.29 (m, 2H), 6.81 (d, J=9 Hz, 1H), 4.27 (d, J=17 Hz, 1H), 3.98 (dd, $J_1$=16 Hz, $J_2$=11 Hz, 1H), 3.81 (m, 1H), 3.60 (d, J=13 Hz, 1H), 3.48 (m, 1H), 3.43 (m, 1H), 3.37 (m, 1H), 3.22 (m, 1H), 2.93 (m, 1H), 2.91 (d, J=5 Hz, 3H), 2.37 (s, 3H), 2.27 (s, 3H), 2.24 (m, 1H); MS (ESI, EI$^+$): m/z=436 (MH$^+$); melting point: 247-261° C.

Methyl 4-(2-(2,5-dichlorophenylthio)-5-nitrophenylsulfonyl)piperazine-2-carboxylate 139. HPLC purity: 97.5%; $^1$H NMR (500 MHz, CDCl$_3$) δ 8.79 (d, J=2, 1H), 8.13 (dd, $J_1$=9 Hz, $J_2$=3 Hz, 1H), 7.72 (d, J=2 Hz, 1H), 7.55 (d, J=9 Hz, 1H), 7.49 (dd, $J_1$=9 Hz, $J_2$=2 Hz, 1H), 6.86 (d, J=9 Hz, 1H), 3.95

(dd, J$_1$=12 Hz, J$_2$=2 Hz, 1H), 3.72 (s, 3H), 3.64 (m, 2H), 3.17 (m, 3H), 2.95 (m, 1H): MS (ESI, EI$^+$): m/z=506 (MH$^+$); melting point: 157-159° C.

1-(2-(2,5-Dimethylphenoxy)-5-nitrophenylsulfonyl)-4-methylpiperazine, hydrochloride 146. HPLC purity: 98.5%; $^1$H NMR (500 MHz, CDCl$_3$) δ 13.50 (s, 1H), 8.84 (d, J=3 Hz, 1H), 8.28 (dd, J$_1$=9 Hz, J$_2$=3 Hz, 1H), 7.21 (d, J=8 Hz, 1H), 7.10 (s, 1H), 7.07 (d, J=8 Hz, 1H), 6.74 (d, J=9 Hz, 1H), 4.06 (m, 2H), 3.86 (m, 2H), 3.48 (m, 2H), 2.83 (s, 3H), 2.38 (s, 3H), 2.13 (s, 3H); MS (ESI, EI$^+$): m/z=406 (MH$^+$); melting point: 296-305° C.

1-(2-(2,5-Dimethylphenoxy)-5-nitrophenylsulfonyl)piperazine, hydrochloride 148. HPLC purity: 100%; $^1$H NMR (500 MHz, DMSO-d$_6$): δ 9.01 (s, 1H), 8.60 (d, J=2 Hz, 1H), 8.43 (dd, J$_1$=2 Hz, J$_2$=8 Hz, 1H), 7.33 (d, J=8 Hz, 1H), 7.14 (d, J=8 Hz, 1H), 7.02 (s, 1H), 6.85 (d, J=8 Hz, 1H), 3.52 (m, 4H), 3.20 (m, 4H), 2.31 (s, 3H), 2.09 (s, 3H); melting point: 80-84° C.

1-(2-(2,5-Dimethylphenoxy)-5-nitrophenylsulfonyl)piperazine, dihydrochloride 148. HPLC purity: 98.4%; $^1$H NMR (500 MHz, DMSO-d$_6$): δ 9.45 (s, 2H), 8.60 (d, J=2 Hz, 1H), 8.43 (dd, J$_1$=2 Hz, J$_2$=8 Hz, 1H), 7.33 (d, J=8 Hz, 1H), 7.13 (d, J=9 Hz, 2H), 6.84 (d, J=8 Hz, 1H), 3.58 (m, 4H), 3.18 (m, 4H), 2.32 (s, 3H), 2.09 (s, 3H); MS (ESI, EI$^+$): m/z=392 (MH$^+$); melting point: 165° C.

Example 7

CCR3 Receptor Binding Assay

Cells were washed once with PBS and resuspended in a binding buffer (25 mM HEPES pH 7.6, 5 mM MgCl$_2$, 1 mM CaCl$_2$, 0.5% BSA, 0.1% NaN$_3$), 100 mL of cell suspension (2×10$^5$ cells/well) and 0.1 nM [$^{125}$I]-labeled human eotaxin/CCL11 (2000 Ci/mmol specific activity) were mixed in a 96-well U-bottom polypropylene plate, and incubated for 60 min at room temperature for the binding reaction. The cell suspension was then transferred to a filtration plate (#MAFB, Millipore), and washed 3 times with the binding buffer containing 0.5 M NaCl, scintillant added, and the radioactivity was counted on a TopCount (Packard). For the determination of non-specific binding, the cell suspension and [$^{125}$I]-labeled human eotaxin/CCL11 were incubated in the presence of 500 nM of unlabeled human eotaxin/CCL11. See, Iino et al., "Molecular cloning and functional characterization of cynomolgus monkey (*Macaca fascicularis*) CC chemokine receptor, CCR3," *Cytokine* 2002, 19, 276-286.

The biological results are summarized in Tables 1 and 2, wherein A represents a value no greater than 10 nM; B represents a value greater than 10 nM but no greater than 25 nM; C represents a value greater than 25 nM but no greater than 100 nM; D represents a value greater than 100 nM but no greater than 500 nM; and E represents a value greater than 5 nM.

TABLE 1

| Cmpd # | K$_i$ Free | K$_i$ HCl$^a$ | Cmpd # | K$_i$ Free | K$_i$ HCl$^a$ |
|---|---|---|---|---|---|
| 51 | D | C | 52 | | |
| 53 | C | | 54 | D | C |
| 55 | E | | 56 | C | C |
| 57 | | E | 58 | E | |
| 59 | E | E | 60 | E | E |
| 61 | B | | 62 | | E |
| 63 | E | E | 64 | E | E |
| 65 | E | | 66 | A | |
| 67 | C | D | 68 | C | C |
| 69 | C | D | 70 | D | |
| 71 | E | | 72 | E | C |
| 73 | | C | 74 | B | A |
| 75 | | A | 76 | A | A |
| 77 | A | A | 78 | C | C |
| 79 | A | A | 80 | A | A |
| 81 | A | B | 82 | D | |
| 83 | C | A | 84 | A | A |
| 85 | E | | 86 | E | |
| 87 | E | | 88 | A | |
| 89 | B | | 90 | B | |
| 91 | B | | 92 | C | |
| 93 | E | | 94 | | |
| 95 | D | | 96 | C | |
| 97 | D | | 98 | | C |
| 99 | B | | 100 | A | |
| 101 | E | | 102 | E | |
| 103 | E | | 104 | B | |
| 105 | E | | 106 | E | |
| 107 | A | | 108 | A | |
| 109 | E | | 110 | E | |
| 111 | E | | 112 | E | |
| 113 | E | | 114 | E | |
| 115 | E | | 116 | E | |
| 117 | E | | 118 | B | |
| 119 | A | | 120 | E | |
| 121 | A | | 122 | D | |
| 123 | B | | 124 | A | |
| 125 | E | | 126 | B | |
| 127 | E | | 133 | E | |
| 140 | E | | 141 | E | |
| 142 | E | | 143 | E | |
| 147 | E | C | 148 | | E |

$^a$HCl: A hydrochloric acid salt of the corresponding compound.

TABLE 2

| Cmpd # | K$_i$ Free | HCl | H$_2$SO$_4$ | MeSO$_3$H | EtSO$_3$H | HNO$_3$ | (CO$_2$H)$_2$ |
|---|---|---|---|---|---|---|---|
| 80 | A | A | A | A | A | C | C |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method for the treatment, or amelioration of one or more symptoms of asthma, allergic asthma, exercise induced asthma, allergic rhinitis, perennial allergic rhinitis, seasonal allergic rhinitis, atopic dermatitis, conjunctivitis, allergic conjunctivitis, eosinophilic bronchitis, eosinophilic gastroenteritis, allograft rejection, chronic obstructive pulmonary disease, COPD (chronic obstructive pulmonary disorder), arthritis, rheumatoid arthritis, psoriatic arthritis, or osteoarthritis in a subject, which comprises administering to the subject a compound of Formula I:

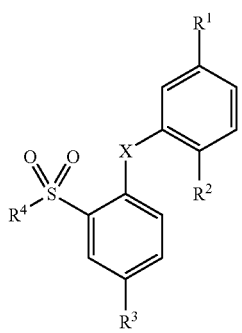

(I)

or an enantiomer, a mixture of enantiomers, a mixture of two or more diastereomers, a tautomer, or a mixture of two or more tautomers thereof; or a pharmaceutically acceptable salt or prodrug thereof;

wherein:

$R^1$ and $R^2$ are each independently (a) halo, cyano, nitro, hydroxyl, or guanidine; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, phenyl, benzyl, phenoxy, benzoxy, or heterocyclyl; or (d) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;

$R^3$ is (a) hydrogen, halo, cyano, nitro, or hydroxyl; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, or tetrazolyl; or (d) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)$R^{1d}$, —N$R^{1a}$S(O)$_2R^{1d}$, —S(O)$R^{1a}$, —S(O)$_2R^{1a}$, —S(O)N$R^{1b}R^{1c}$, or —S(O)$_2$N$R^{1b}R^{1c}$;

$R^4$ is

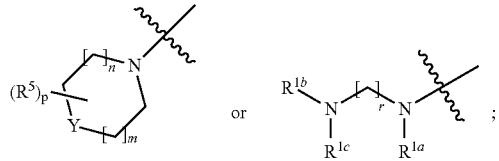

$R^5$ is (a) halo, cyano, nitro, hydroxyl, oxo, or guanidine; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, phenyl, benzyl, phenoxy, benzoxy, or heterocyclyl; or (d) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)$R^{1d}$, —N$R^{1a}$S(O)$_2R^{1d}$, —S(O)$R^{1a}$, —S(O)$_2R^{1a}$, —S(O)N$R^{1b}R^{1c}$, or —S(O)$_2$N$R^{1b}R^{1c}$;

X is O or S;

Y is —O—, —S—, —S(O)—, —S(O)$_2$—, —N($R^{1a}$)—, —C($R^{1a}$)($R^{1d}$)—, or —C($R^{1a}$)(N$R^{1b}R^{1c}$)—;

m is an integer from 0 to 3;

n is an integer from 1 to 3;

p is an integer from 0 to 4;

r is an integer from 1 to 6; and each $R^{1a}$, $R^{1b}$, $R^{1c}$, and $R^{1d}$ is independently (a) hydrogen, phenyl, or benzyl; (b) $C_{3-7}$ cycloalkyl, heteroaryl, or heterocyclyl, each optionally substituted; or (c) $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; or each pair of $R^{1b}$ and $R^{1c}$ together with the N atom to which they are attached independently form heteroaryl or heterocyclyl;

with the proviso that when X is O; Y is —N($R^{1a}$)—; m and n are 1; $R^1$ and $R^2$ are each independently chloro, nitro, methyl, or isopropyl; $R^3$ is nitro; and p is 0; then $R^{1a}$ is not hydrogen.

2. The method of claim 1, wherein the compound has the structure of Formula II:

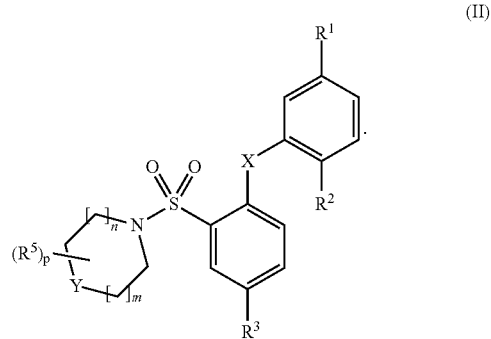

(II)

3. The method of claim 1, wherein $R^5$ is oxo; $C_{1-6}$ alkyl, optionally substituted with one, two, or three halo; or —C(O)OR$^{1a}$.

4. The method of claim 3, wherein $R^5$ is oxo, methyl, or methoxycarbonyl.

5. The method of claim 1, wherein p is 0, 1, or 2.

6. The method of claim 1, wherein m is 1.

7. The method of claim 1, wherein n is 1 or 2.

8. The method of claim 1, wherein Y is —O—, —S—, —S(O)—, or —S(O)$_2$—.

9. The method of claim 1, wherein Y is —NR$^{1a}$—.

10. The method of claim 9, wherein $R^{1a}$ is hydrogen, $C_{1-6}$ alkyl, $C_{3-7}$ cycloalkyl, heteroaryl, or heterocyclyl.

11. The method of claim 9, wherein $R^{1a}$ is hydrogen, methyl, ethyl, propyl, pentyl, cyclopentyl, cyclohexyl, or 3-oxo-1H-imidazo[1,5-c]imidazol-2(3H)-yl.

12. The method of claim 1, wherein Y is —C(R$^{1a}$)(R$^{1d}$)—.

13. The method of claim 12, wherein $R^{1a}$ is hydrogen, $C_{1-6}$ alkyl, $C_{3-7}$ cycloalkyl, heteroaryl, or heterocyclyl.

14. The method of claim 12, wherein $R^{1a}$ is hydrogen, methyl, ethyl, propyl, pentyl, cyclopentyl, cyclohexyl, or 3-oxo-1H-imidazo[1,5-c]imidazol-2(3H)-yl.

15. The method of claim 12, wherein $R^{1d}$ is hydrogen.

16. The method of claim 1, wherein the compound has the structure of Formula III:

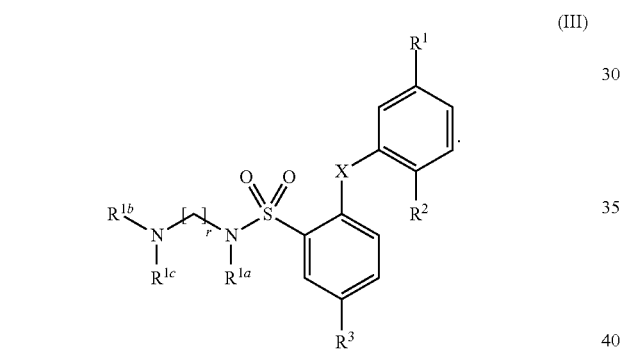

(III)

17. The method of claim 16, wherein $R^{1a}$ is hydrogen or $C_{1-6}$ alkyl.

18. The method of claim 16, wherein $R^{1b}$ is hydrogen or $C_{1-6}$ alkyl.

19. The method compound of claim 16, wherein $R^{1b}$ is ethyl.

20. The method of claim 16, wherein $R^{1c}$ is hydrogen or $C_{1-6}$ alkyl.

21. The method of claim 16, wherein $R^{1c}$ is ethyl.

22. The method of claim 16, wherein $R^{1b}$ and $R^{1c}$ together with the N atom to which they are attached form heteroaryl or heterocyclyl.

23. The method of claim 22, wherein $R^{1b}$ and $R^{1c}$ together with the N atom to which they are attached form 5- to 7-membered heterocyclyl.

24. The method of claim 23, wherein the heterocyclyl is pyrrolidinyl or piperidinyl.

25. The method of claim 1, wherein $R^1$ is halo or $C_{1-6}$ alkyl.

26. The method of claim 25, wherein $R^1$ is fluoro, chloro, or methyl.

27. The method of claim 1, wherein $R^2$ is halo or $C_{1-6}$ alkyl.

28. The method of claim 27, wherein $R^2$ is fluoro, chloro, or methyl.

29. The method of claim 1, wherein $R^1$ and $R^2$ are fluoro.

30. The method of claim 1, wherein $R^1$ and $R^2$ are chloro.

31. The method of claim 1, wherein $R^1$ and $R^2$ are methyl.

32. The method of claim 1, wherein $R^3$ is cyano or nitro.

33. The method of claim 1, wherein X is O.

34. The method of claim 1, wherein X is S.

35. The method of claim 1, wherein the compound is selected from the group consisting of:

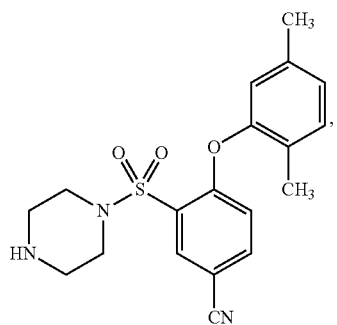

51

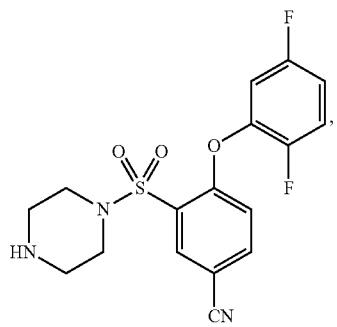

52

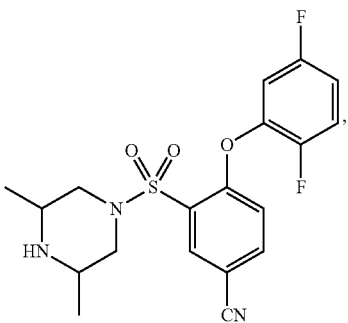

53

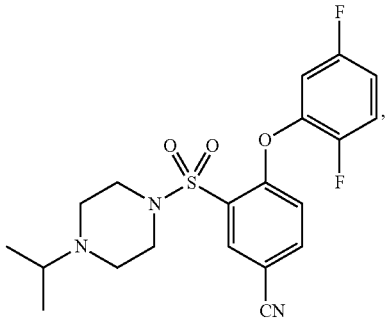

54

| 55 | | 60 |
|---|---|---|
| 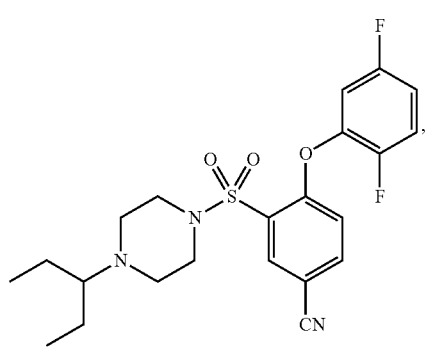 | | 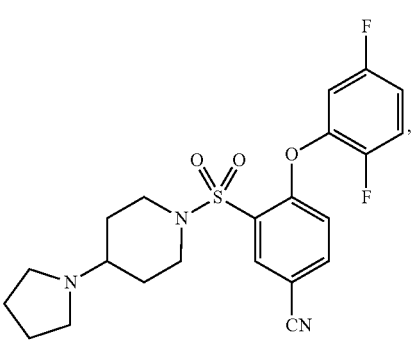 |
| 56 | | 61 |
| 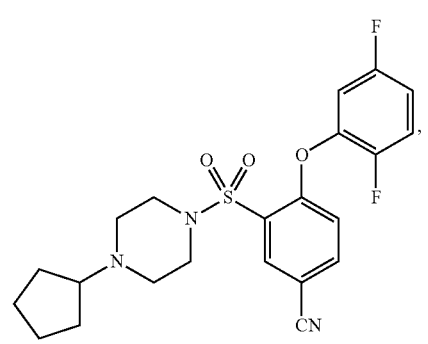 | | 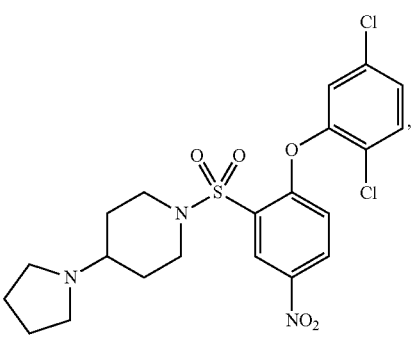 |
| 57 | | 62 |
| 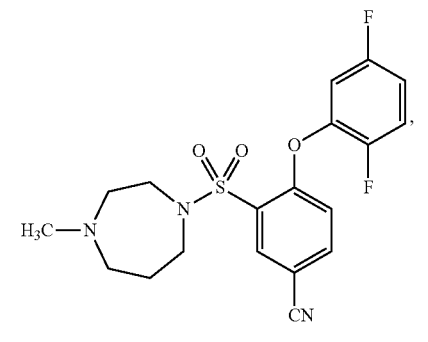 | | 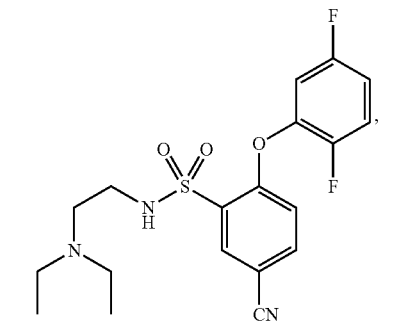 |
| 58 | | 63 |
| 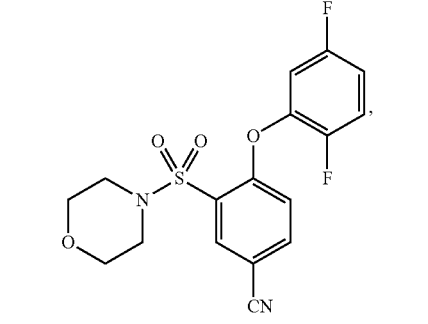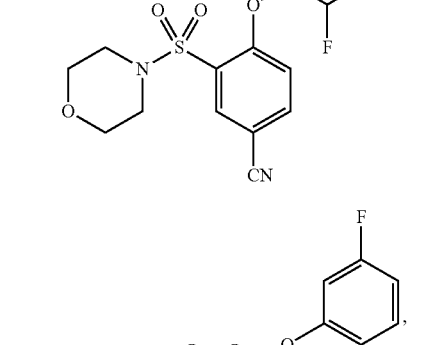 | | 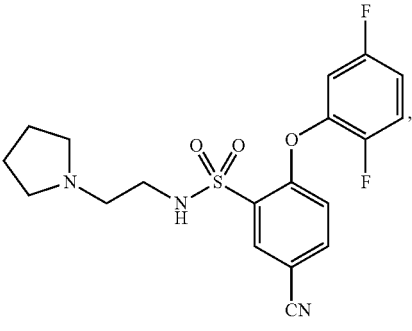 |
| 59 | | 64 |
| 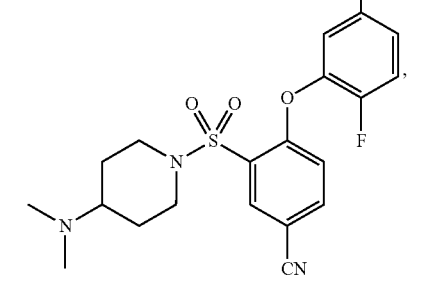 | | 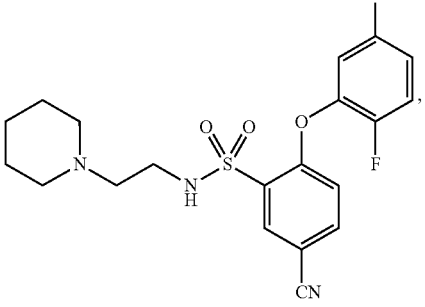 |

| 65 | 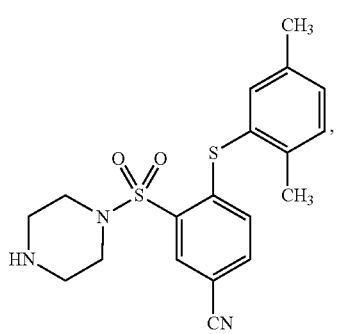 |
| --- | --- |
| 66 | 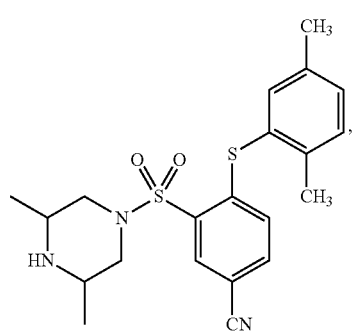 |
| 67 | 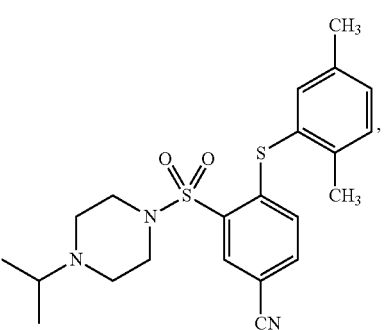 |
| 68 | 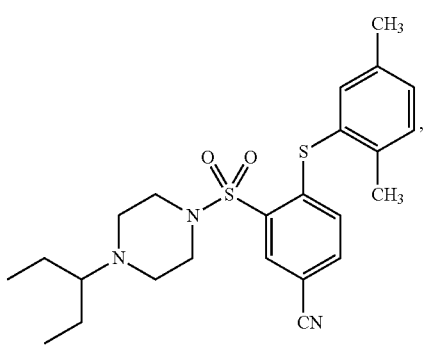 |
| 69 | 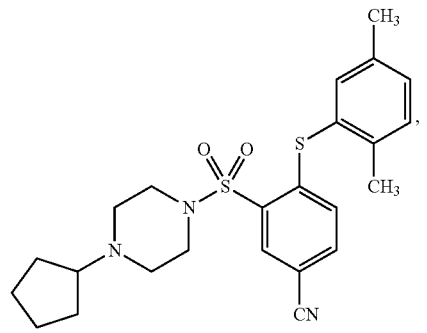 |
| 70 | 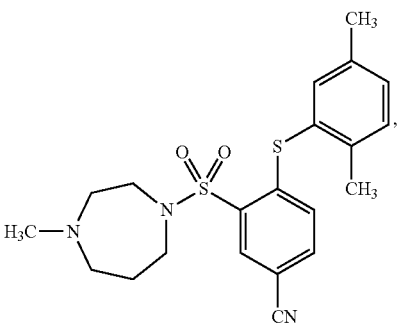 |
| 71 | 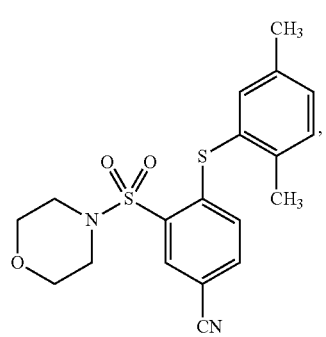 |
| 72 | 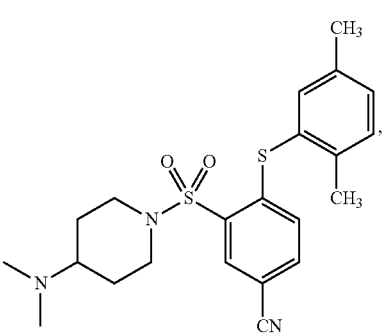 |
| 73 | 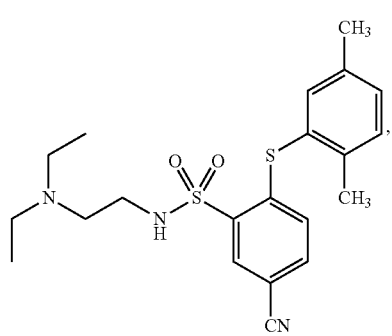 |
| 74 | 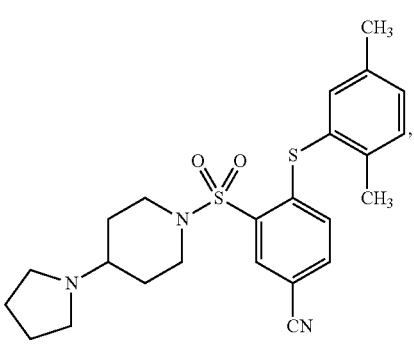 |

75 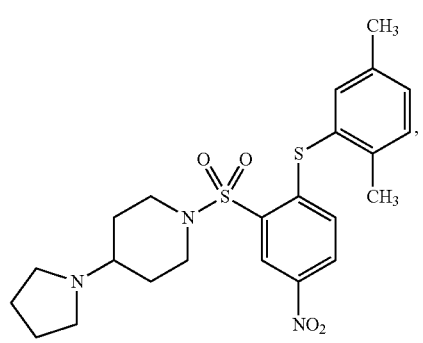
76 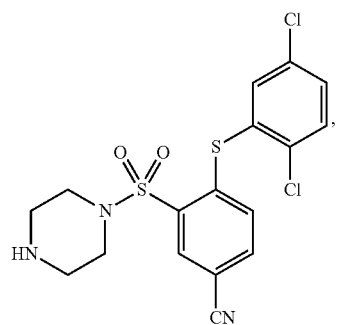
77 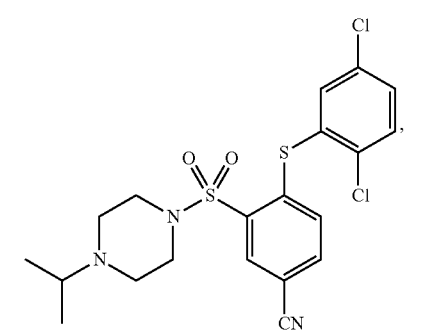
78 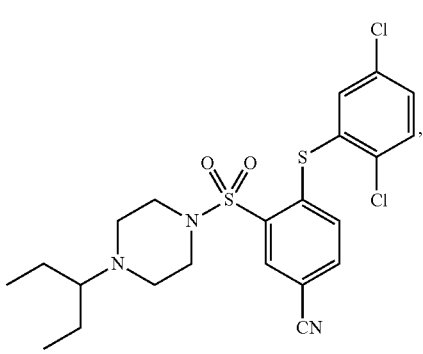
79 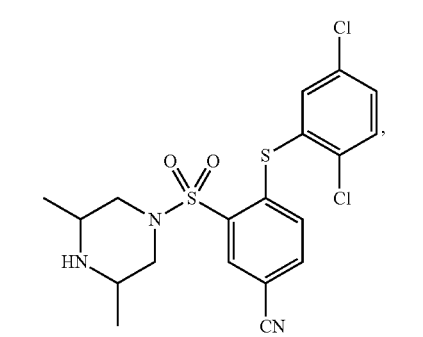
80 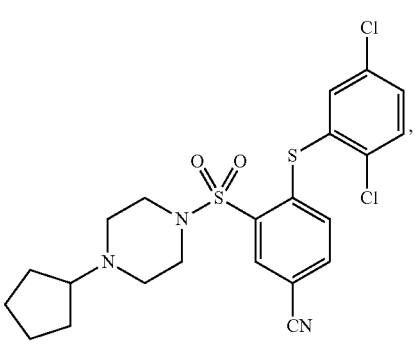
81 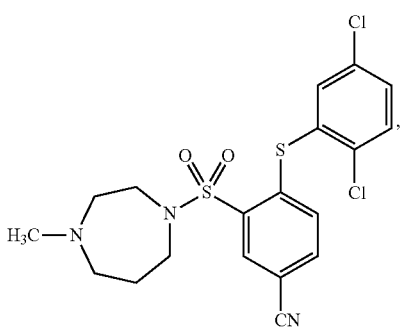
82 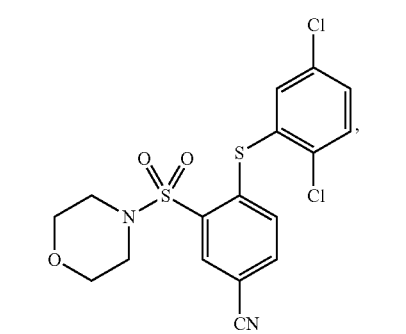
83 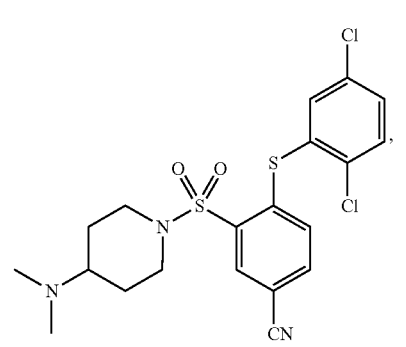
84 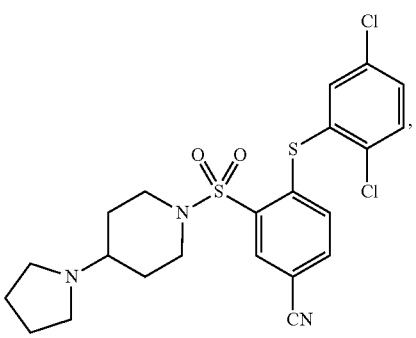

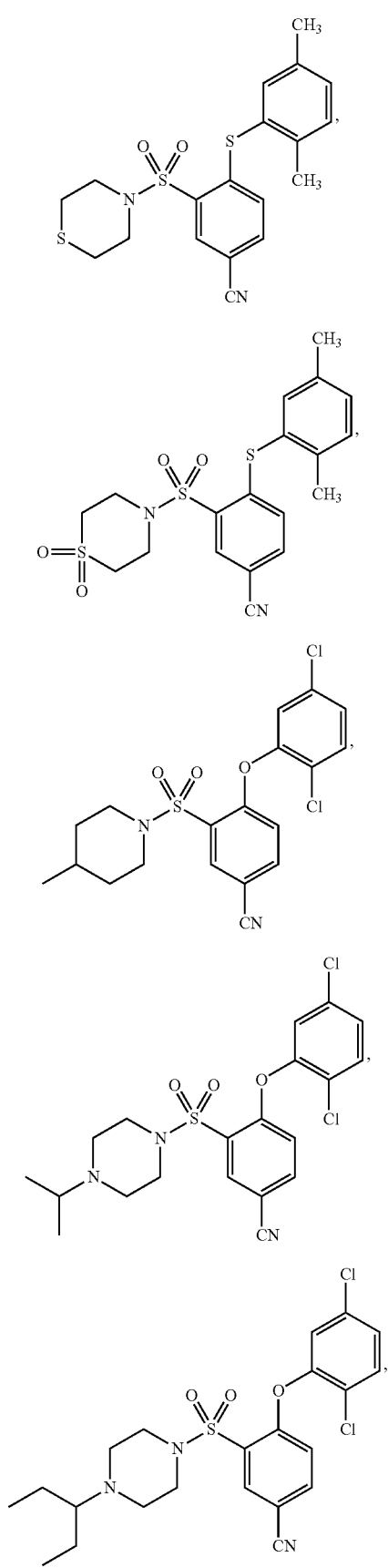
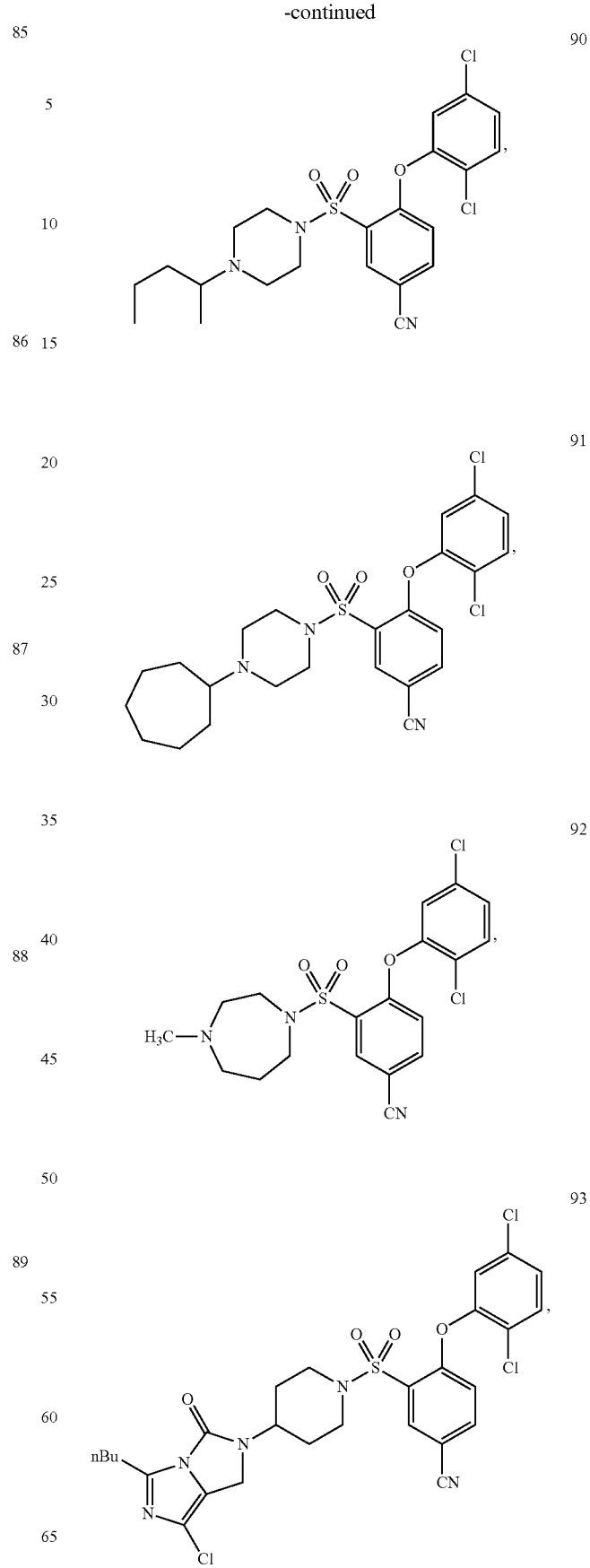

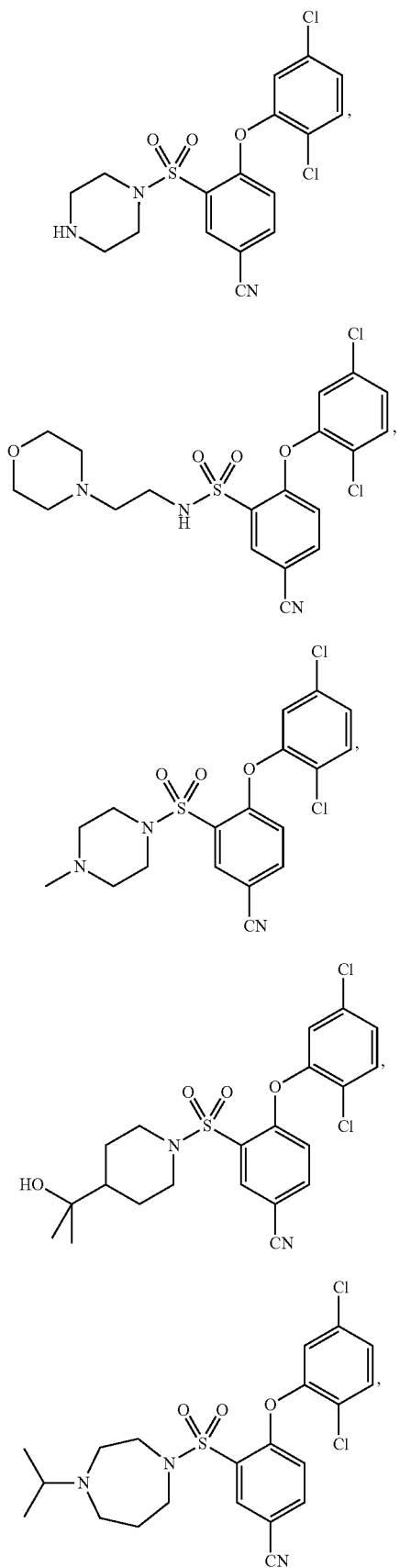
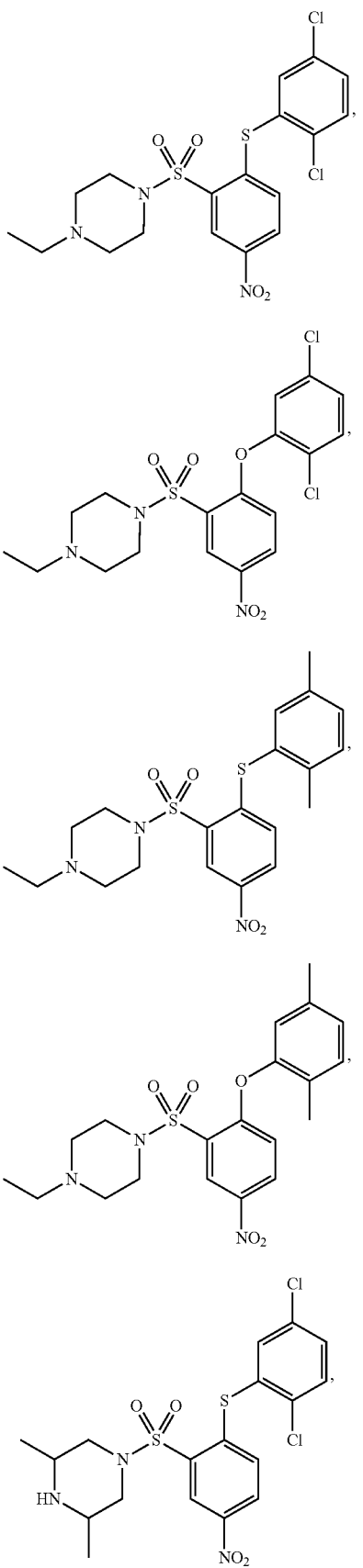

| | |
|---|---|
| 104 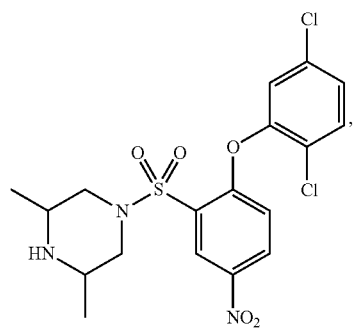 | 109 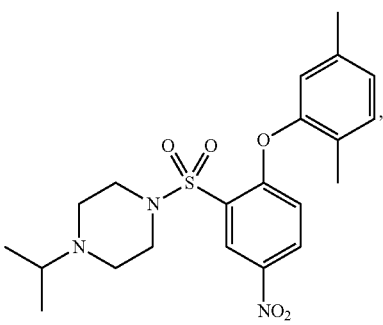 |
| 105 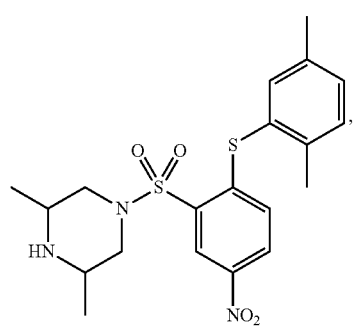 | 110 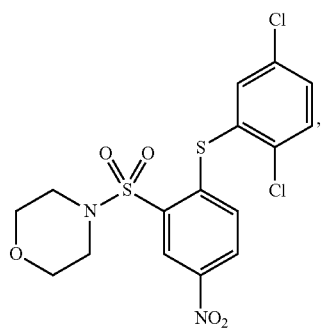 |
| 106 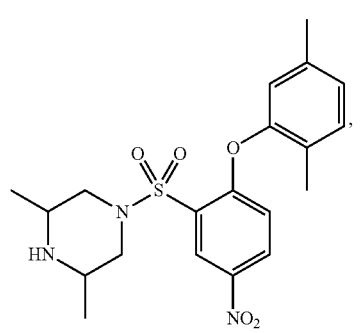 | 111 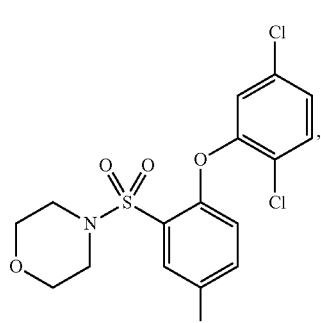 |
| 107 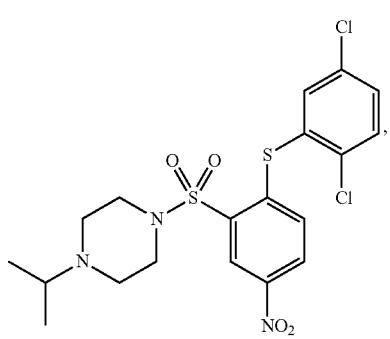 | 112 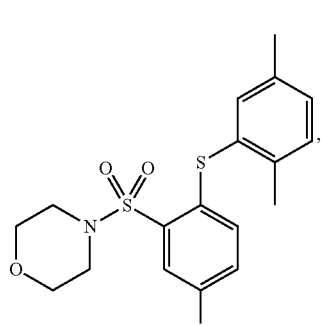 |
| 108 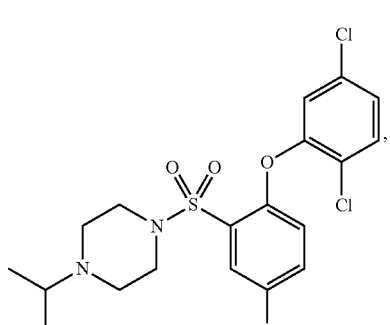 | 113 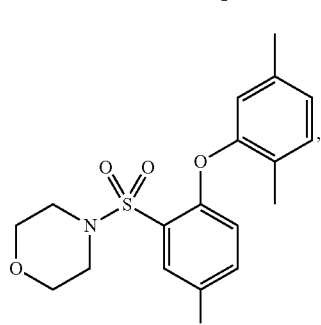 |

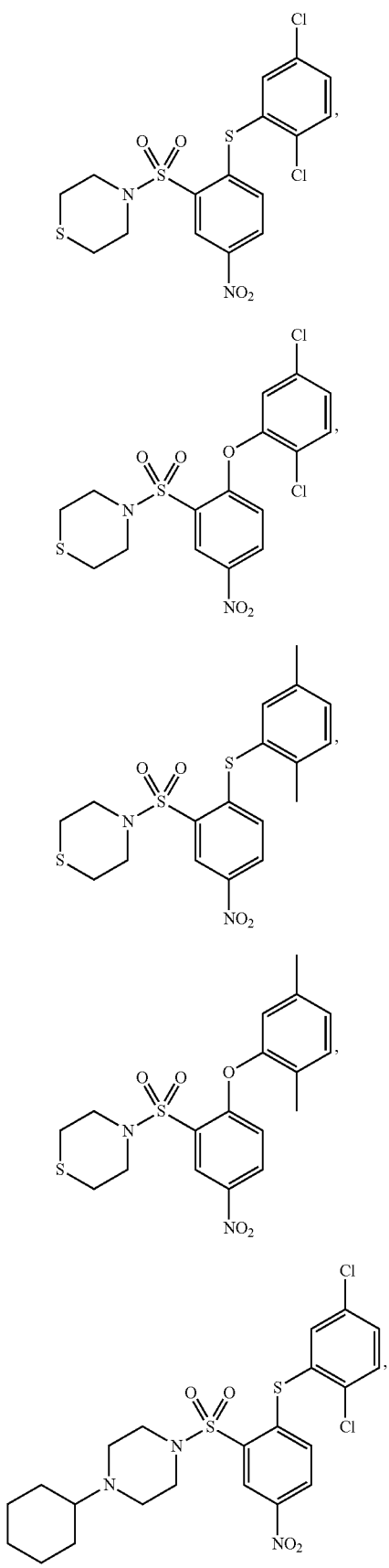
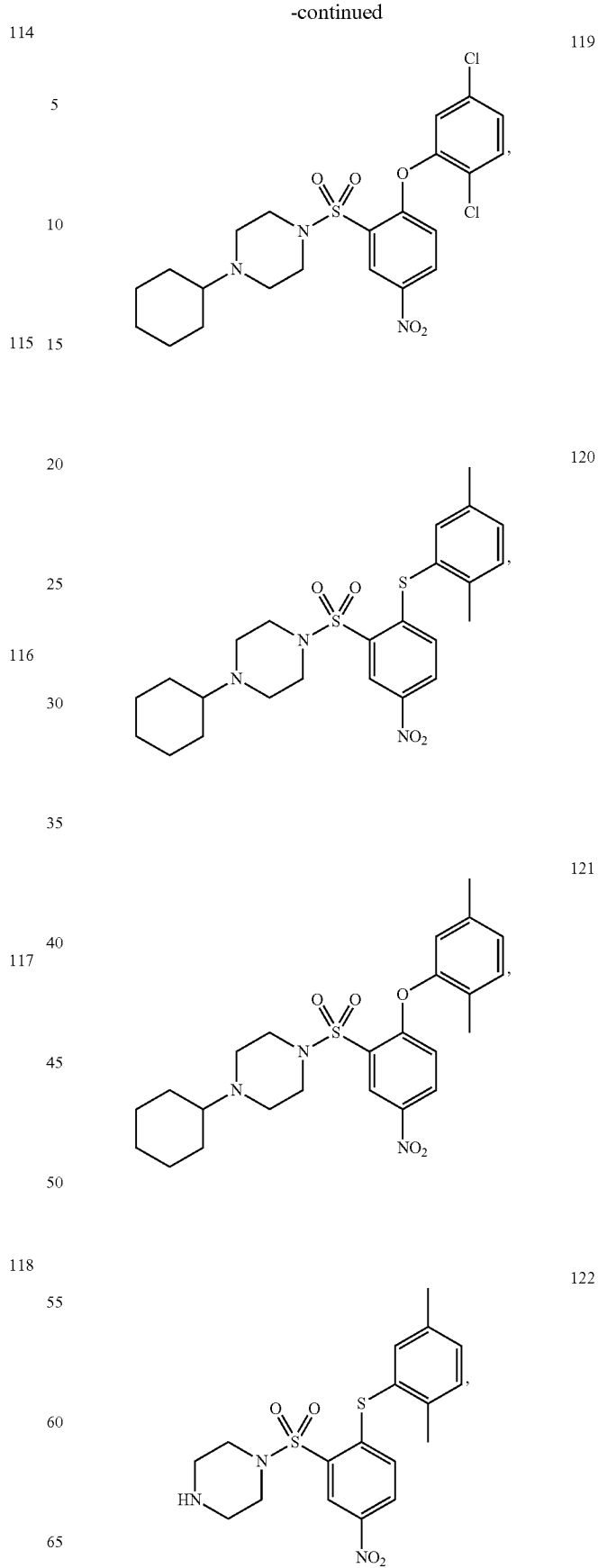

123
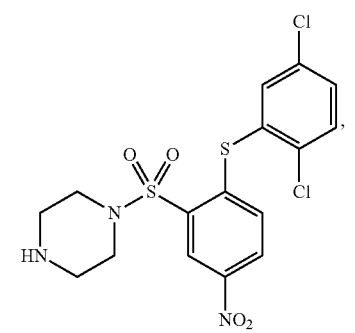
124
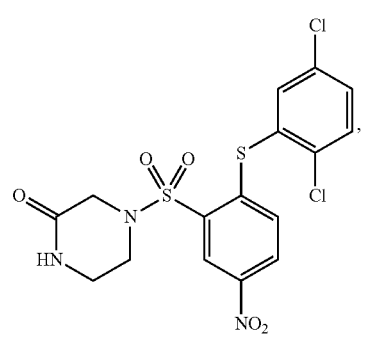
125
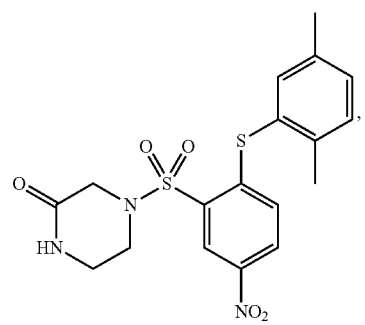
126
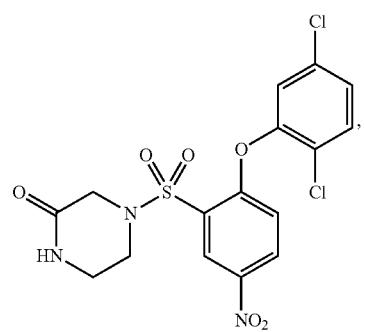
127
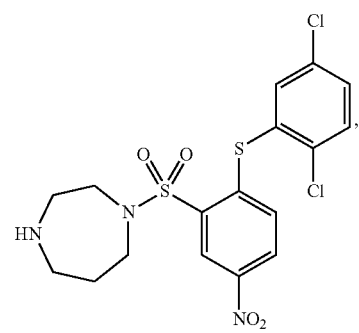
128
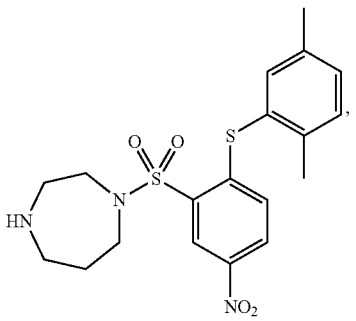
129
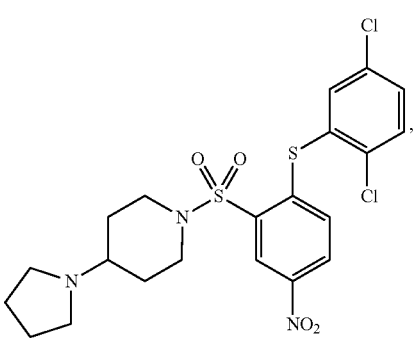
130
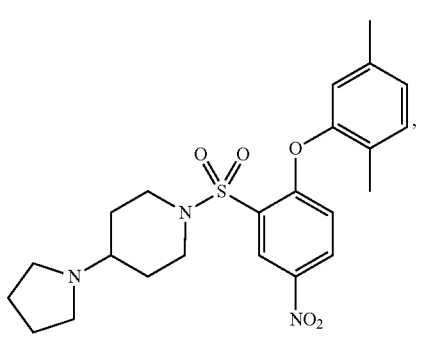
131
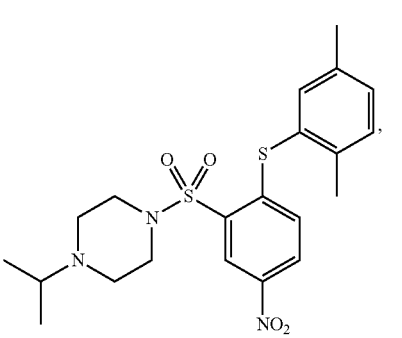
132
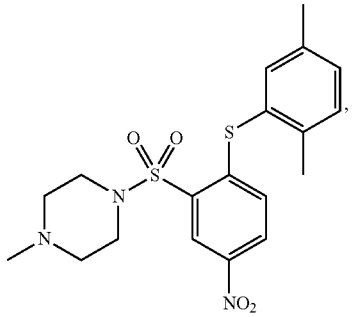

133 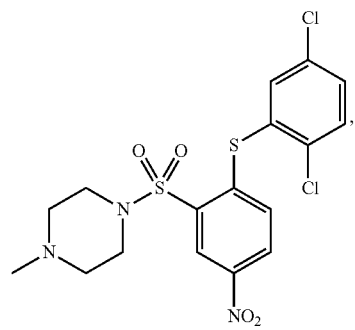
134 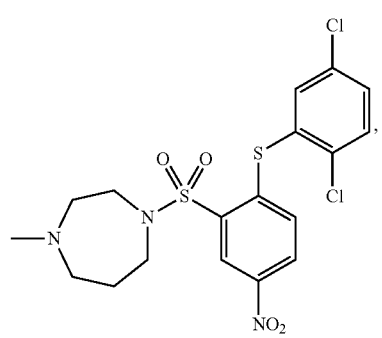
135 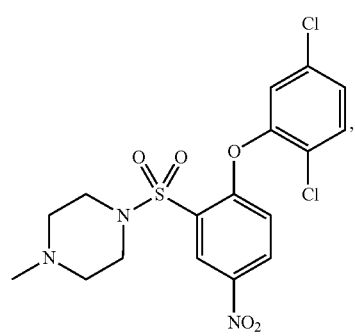
136 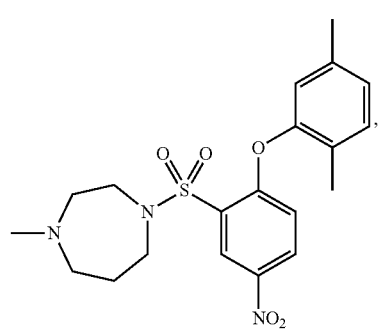
137 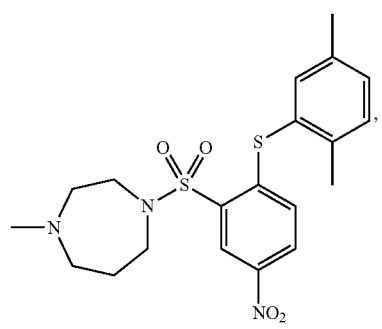
138 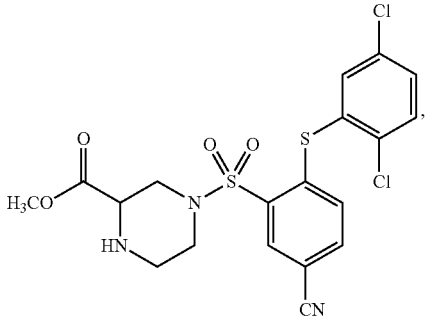
139 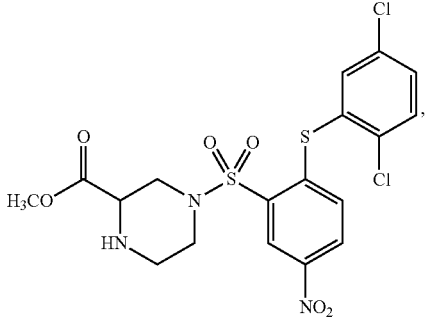
140 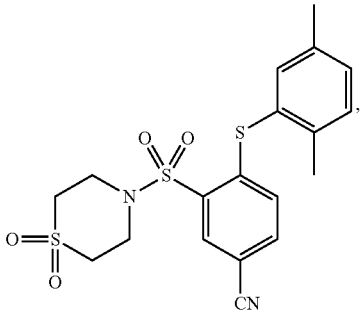
141 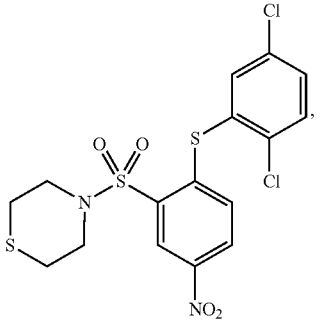
142 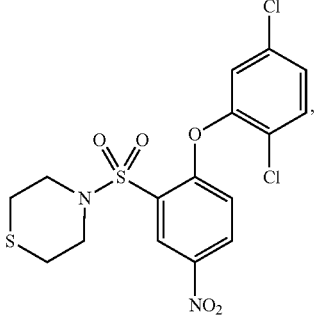

-continued

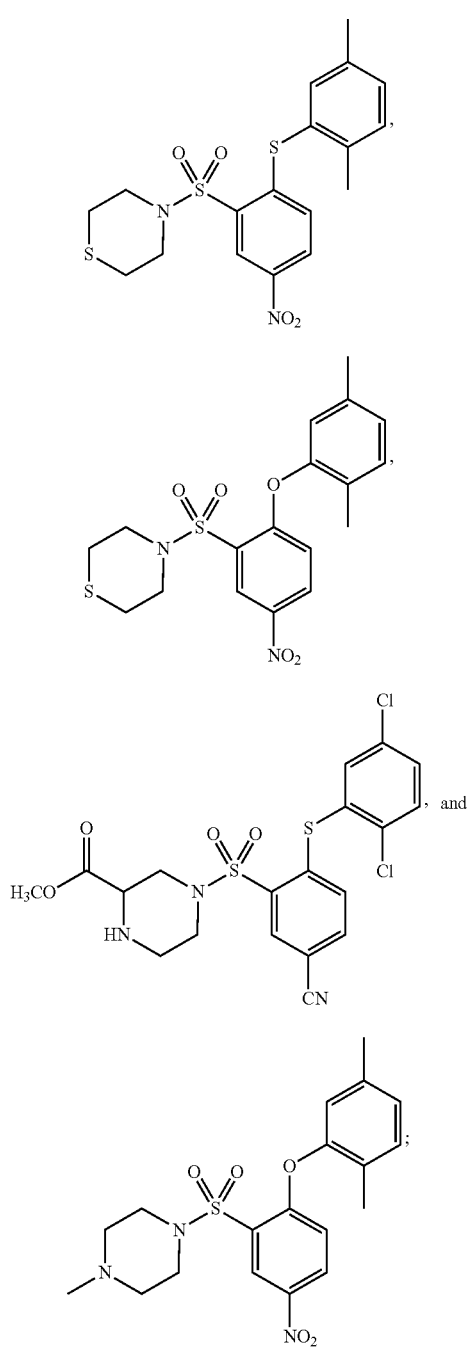

and enantiomers, mixtures of enantiomers, mixtures of two or more diastereomers, tautomers, and mixtures of two or more tautomers thereof; and pharmaceutically acceptable salts, solvates, hydrates, and prodrugs thereof.

36. The method of claim 1, wherein the compound is a hydrochloride salt.

37. The method of claim 1, wherein the disorder, disease, or condition is asthma, exercise induced asthma, allergic rhinitis, atopic dermatitis, chronic obstructive pulmonary disease, or allergic conjunctivitis.

38. The method of claim 1, wherein the compound is administered orally, parenterally, or topically.

39. The method of claim 1, wherein the compound is administered in combination with a second therapeutic agent.

40. A method for modulating CCR3 activity, comprising contacting a CCR3 receptor with a compound of Formula I:

$$\text{(I)}$$

or an enantiomer, a mixture of enantiomers, a mixture of two or more diastereomers, a tautomer, or a mixture of two or more tautomers thereof; or a pharmaceutically acceptable salt or prodrug thereof;

wherein:

$R^1$ and $R^2$ are each independently (a) halo, cyano, nitro, hydroxyl, or guanidine; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, phenyl, benzyl, phenoxy, benzoxy, or heterocyclyl; or (d) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;

$R^3$ is (a) hydrogen, halo, cyano, nitro, or hydroxyl; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c) $C_{2-6}$ alkenyl, $C_{2-6}$ alkynyl, or tetrazolyl; or (d) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)N$R^{1b}R^{1c}$, —N$R^{1a}$S(O)$_2$N$R^{1b}R^{1c}$, —S(O)$R^{1a}$, —S(O)$_2R^{1a}$, —S(O)N$R^{1b}R^{1c}$, or —S(O)$_2$N$R^{1b}R^{1c}$;

$R^4$ is

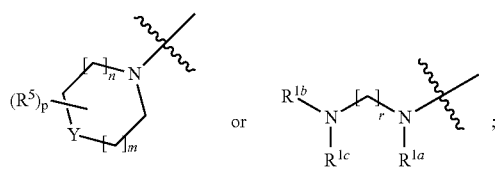

$R^5$ is (a) halo, cyano, nitro, hydroxyl, oxo, or guanidine; (b) $C_{1-6}$ alkyl, $C_{1-6}$ alkoxy, or $C_{1-6}$ alkylthio, wherein the alkyl, alkoxy, and alkylthio are each independently and optionally substituted with one, two, or three halo; (c)

$C_{2-6}$ alkenyl, $C_{2-6}$ alkynyl, phenyl, benzyl, phenoxy, benzoxy, or heterocyclyl; or (d) —C(O)$R^{1a}$, —C(O)O$R^{1a}$, —C(O)N$R^{1b}R^{1c}$, —C(N$R^{1a}$)N$R^{1b}R^{1c}$, —OC(O)$R^{1a}$, —OC(O)O$R^{1a}$, —OC(O)N$R^{1b}R^{1c}$, —OC(=N$R^{1a}$)N$R^{1b}R^{1c}$, —OS(O)$R^{1a}$, —OS(O)$_2R^{1a}$, —OS(O)N$R^{1b}R^{1c}$, —OS(O)$_2$N$R^{1b}R^{1c}$, —N$R^{1b}R^{1c}$, —N$R^{1a}$C(O)$R^{1d}$, —N$R^{1a}$C(O)O$R^{1d}$, —N$R^{1a}$C(O)N$R^{1b}R^{1c}$, —N$R^{1a}$C(=N$R^{1d}$)N$R^{1b}R^{1c}$, —N$R^{1a}$S(O)$R^{1d}$, —N$R^{1a}$S(O)$_2R^{1d}$, —N$R^{1a}$S(O)$R^{1d}$, —N$R^{1a}$S(O)$_2R^{1d}$, —S(O)$R^{1a}$, —S(O)$_2R^{1a}$, —S(O)N$R^{1b}R^{1c}$, or —S(O)$_2$N$R^{1b}R^{1c}$;

X is O or S;

Y is —O—, —S—, —S(O)—, —S(O)$_2$—, —N($R^{1a}$)—, —C($R^{1a}$)($R^{1d}$)—, or —C($R^{1a}$)(N$R^{1b}R^{1c}$)—;

m is an integer from 0 to 3;

n is an integer from 1 to 3;

p is an integer from 0 to 4;

r is an integer from 1 to 6; and each $R^{1a}$, $R^{1b}$, $R^{1c}$, and $R^{1d}$ is independently (a) hydrogen, phenyl, or benzyl; (b) $C_{3-7}$ cycloalkyl, heteroaryl, or heterocyclyl, each optionally substituted; or (c) $C_{1-6}$ alkyl, optionally substituted with one, two, or three substituents, each independently selected from halo, hydroxyl, carboxy, alkoxy, carbamoyl, $C_{6-14}$ aryl, $C_{1-6}$ alkylcarbamoyl, di($C_{1-6}$ alkyl)carbamoyl, $C_{3-7}$ cycloalkylcarbamoyl, and $C_{3-7}$ heterocyclylcarbamoyl; or each pair of $R^{1b}$ and $R^{1c}$ together with the N atom to which they are attached independently form heteroaryl or heterocyclyl;

with the proviso that when X is O; Y is —N($R^{1a}$)—; m and n are 1; $R^1$ and $R^2$ are each independently chloro, nitro, methyl, or isopropyl; $R^3$ is nitro; and p is 0; then $R^{1a}$ is not hydrogen.

* * * * *